United States Patent
Gu et al.

(10) Patent No.: US 11,213,580 B2
(45) Date of Patent: Jan. 4, 2022

(54) MUTANT OF L1 PROTEIN OF HUMAN PAPILLOMAVIRUS TYPE 16

(71) Applicants: XIAMEN UNIVERSITY, Xiamen (CN); XIAMEN INNOVAX BIOTECH CO., LTD., Xiamen (CN)

(72) Inventors: Ying Gu, Xiamen (CN); Shaowei Li, Xiamen (CN); Shuo Song, Xiamen (CN); Maozhou He, Xiamen (CN); Zhihai Li, Xiamen (CN); Ningshao Xia, Xiamen (CN)

(73) Assignees: XIAMEN UNIVERSITY, Xiamen (CN); XIAMEN INNOVAX BIOTECH CO., LTD., Xiamen (CN)

( * ) Notice: Subject to any disclaimer, the term of this patent is extended or adjusted under 35 U.S.C. 154(b) by 28 days.

(21) Appl. No.: 16/630,673

(22) PCT Filed: Jul. 13, 2018

(86) PCT No.: PCT/CN2018/095632
§ 371 (c)(1),
(2) Date: Jan. 13, 2020

(87) PCT Pub. No.: WO2019/011331
PCT Pub. Date: Jan. 17, 2019

(65) Prior Publication Data
US 2021/0000938 A1 Jan. 7, 2021

(30) Foreign Application Priority Data
Jul. 14, 2017 (CN) .......................... 201710573731.9

(51) Int. Cl.
| | |
|---|---|
| *A61K 39/00* | (2006.01) |
| *A61K 39/12* | (2006.01) |
| *C07K 14/005* | (2006.01) |
| *C07K 14/025* | (2006.01) |
| *C12N 7/00* | (2006.01) |
| *A61P 31/20* | (2006.01) |
| *A61K 39/39* | (2006.01) |

(52) U.S. Cl.
CPC .............. *A61K 39/12* (2013.01); *A61K 39/39* (2013.01); *A61P 31/20* (2018.01)

(58) Field of Classification Search
CPC ........ C07K 14/005; C12N 2710/20022; C12N 2710/20023; C12N 7/00; A61K 2039/5258
See application file for complete search history.

(56) References Cited

U.S. PATENT DOCUMENTS

| | | | |
|---|---|---|---|
| 6,562,351 | B2 | 5/2003 | Hallek et al. |
| 6,689,366 | B1 | 2/2004 | Jansen et al. |
| 2004/0081661 | A1 | 4/2004 | Hallek et al. |
| 2010/0255031 | A1 | 10/2010 | Gu et al. |

FOREIGN PATENT DOCUMENTS

| | | | |
|---|---|---|---|
| CN | 101293918 | * | 10/2008 |
| CN | 101293918 A | | 10/2008 |
| CN | 101518647 A | | 9/2009 |
| CN | 102747047 A | | 10/2012 |
| EP | 2 377 879 A1 | | 10/2011 |
| WO | WO 2008/034388 A1 | | 3/2008 |
| WO | WO 2009/055491 A2 | | 4/2009 |

OTHER PUBLICATIONS

Extended European Search Report dated Apr. 1, 2021 in European Patent Application No. 18832785.2, 8 pages.
"RecName: Full=Major capsid protein L1 {ECO:0000256|HAMAP-Rule:MF_04002, ECO:0000256|RuleBase:RU361246}:" Database UniProt [Online], XP002802430, 1996, retrieved from EBI accession No. UNIPROT:Q81017.
International Search Report dated Sep. 30, 2018 in PCT/CN2018/095632, 5 pages.
Brooke Bishop et al., "Crystal Structures of Four Types of Human Papillomavirus L1 Capsid Proteins", The Journal of Biological Chemistry, vol. 282, No. 43, Oct. 26, 2007, pp. 31803-31811 with cover page.
Neil D. Christensen, et al., "Hybrid Papillomavirus L1 Molecules Assemble into Virus-like Particles That Reconstitute Conformational Epitopes and Induce Neutralizing Antibodies to Distinct HPV Types" Virology, vol. 291, 2001, pp. 324-334.

* cited by examiner

*Primary Examiner* — Barry A Chestnut
(74) *Attorney, Agent, or Firm* — Oblon, McClelland, Maier & Neustadt, L.L.P.

(57) ABSTRACT

Provided are a mutated HPV16 L1 protein (or a variant thereof), a sequence encoding the same and a method for preparing the same, as well as a virus-like particle comprising the same. The protein (or variant thereof) and the virus-like particle are capable of inducing neutralizing antibodies against at least two types of HPV (e.g., HPV16 and HPV35, or HPV16, HPV35, and HPV31), and therefore can be used to prevent infection by said at least two HPV types, and a disease caused by said infection, such as cervical cancer and condyloma acuminatum. Also provided are a use of the above protein and virus-like particle in the manufacture of a pharmaceutical composition or vaccine for preventing infection by said at least two HPV types, and a disease caused by said infection, such as cervical cancer and condyloma acuminatum.

19 Claims, 12 Drawing Sheets
Specification includes a Sequence Listing.

MUTANT OF L1 PROTEIN OF HUMAN PAPILLOMAVIRUS TYPE 16

TECHNICAL FIELD

The invention relates to the fields of molecular virology and immunology. In particular, the present invention relates to a mutated HPV16 L1 protein (or a variant thereof), a sequence encoding the same, a method for preparing the same, as well as a virus-like particle comprising the same, in which the protein (or variant thereof) and the virus-like particle are capable of inducing a neutralizing antibody against at least two types of HPV (e.g., HPV 16 and HPV 35; or HPV 16, HPV 35 and HPV 31), and therefore can be used to prevent infection by said at least two HPV types, and a disease caused by said infection, such as cervical cancer and condyloma acuminatum. The invention further relates to a use of the above-mentioned protein and virus-like particle in the manufacture of a pharmaceutical composition or a vaccine for preventing infection by said at least two HPV types, and a disease caused by said infection, such as cervical cancer and condyloma acuminatum.

BACKGROUND ART

Human papillomavirus (HPV) mainly causes warts in skin and mucosa. According to its relationship with tumorigenesis, HPV can be divided into high-risk type and low-risk type, among which infection by high-risk HPV types is confirmed to be the main cause of genital cancers including cervical cancers in women; while infection by low-risk HPV type mainly causes condyloma acuminatum. The most effective way to prevent and control the HPV infections is to administer a HPV vaccine, especially a vaccine against high-risk HPV types capable of causing cervical cancer.

The major capsid protein L1 of HPV has the characteristics of self-assembly into hollow Virus-Like Particle (VLP). The HPV VLP has a symmetrical icosahedral structure composed of 72 pentamers of the major capsid protein L1 (Doorbar, J. and P. H. Gallimore. 1987. J Virol, 61(9): 2793-9). The structure of HPV VLP is highly similar to that of native HPV, retaining most of the neutralizing epitopes of native virus and being capable of inducing high-titer neutralizing antibodies (Kirnbauer, R., F. Booy, et al. 1992 Proc Natl Acad Sci USA 89(24): 12180-4).

However, existing studies have shown that HPV VLP mainly induces neutralizing antibodies against the same HPV type, produces protective immunity against the same HPV type, and only has low cross-protective effect among a few highly homologous types (Sara L. Bissett, Giada Mattiuzzo, et al. 2014 Vaccine. 32:6548-6555). Therefore, the scope of protection of existing HPV vaccines is very limited. In general, VLP of one HPV type can only be used to prevent infection by the same HPV type. In this case, if it needs to expand the scope of protection of HPV vaccines, the only way is to add VLPs of more HPV types in vaccines. Currently available HPV vaccines include Merck's Gardasil® (which is a quadrivalent vaccine against HPV 16, 18, 6 and 11), GSK's Cervarix® (which is a bivalent vaccine against HPV 16, 18) and Merck's Gardasil® 9 (which is a nine-valent vaccine), which are all made by mixing VLPs of multiple types of HP V. However, this approach will result in a significant cost increase in production of HPV vaccines and may lead to potential safety issues due to the increased immunization doses.

Therefore, there is a need in the art to develop HPV virus-like particles capable of inducing protective neutralizing antibodies against multiple types of HPV, so as to more economically and effectively prevent infection by multiple HPV types and the diseases caused thereby such as cervical cancer and condyloma acuminatum.

CONTENTS OF THE INVENTION

The present invention is based, at least in part, on the inventors' unexpected discovery that after replacing a specific segment of L1 protein of Human Papillomavirus (HPV) type 16 with the corresponding segment of L1 protein of a second type of HPV (such as HPV35), the obtained mutated HPV16 L1 protein can induce the generation of high-titer neutralizing antibodies against HPV16 and the second type of HPV (such as HPV35) in the body with a protective effect comparable to that of a mixture of HPV16 VLP and VLP of the second type of HPV; moreover, the protective effect thereof against HPV16 is comparable to that of the HPV 16 VLP alone, and the protective effect thereof against the second-type of HPV (e.g., HPV 35) is comparable to that of VLP of the second-type of HPV alone.

In addition, based on the above substitution, another specific segment of the HPV16 L1 protein may be further substituted with a corresponding segment of L1 protein of a third-type of HPV (e.g., HPV31), and the obtained mutated HPV16 L1 protein having double substitutions can induce the generation of high-titer neutralizing antibodies against HPV16, the second type of HPV (such as HPV35) and the third type of HPV (such as HPV31) in the body with a protective effect comparable to that of a mixture of HPV16 VLP, and VLPs of the second type and third type of HPV; moreover, the protective effect thereof against HPV16 is comparable to that of the HPV16 VLP alone, the protective effect thereof against the second-type of HPV (e.g., HPV35) is comparable to that of VLP of the second-type of HPV alone, and the protective effect thereof against the third-type of HPV (e.g., HPV31) is comparable to that of VLP of the third-type of HPV alone.

Thus, in one aspect, the invention provides a mutated HPV16 L1 protein or a variant thereof, wherein the mutated HPV16 L1 protein has the following mutations compared to a wild-type HPV16 L1 protein:

(1) a N-terminal truncation of 4-50 amino acids, such as 4, 6, 8, 10, 20, 30 or 40 amino acids; and (2) a substitution of amino acid residues at positions 292-316 of the wild-type HPV16 L1 protein with amino acid residues at the corresponding positions of a L1 protein of a second type of wild-type HPV;

optionally, the mutated HPV16 L1 protein further has the following mutation:

(3) a substitution of amino acid residues at positions 76-87 of the wild-type HPV16 L1 protein with amino acid residues at the corresponding positions of a L1 protein of a third type of wild-type HPV;

(4) a substitution of amino acid residues at positions 152-167 of the wild-type HPV16 L1 protein with amino acid residues at the corresponding positions of a L1 protein of a third type of wild-type HPV; or (5) a substitution of amino acid residues at positions 202-207 of the wild-type HPV16 L1 protein with amino acid residues at the corresponding positions of a L1 protein of a third type of wild-type HPV;

and, the variant differs from the mutated HPV16 L1 protein only by substitution (preferably conservative substitution), addition or deletion of one or several (e.g., 1, 2, 3, 4, 5, 6, 7, 8, or 9) amino acids, and maintains the function of the mutated HPV16 L1 protein, i.e., an ability of inducing neutralizing antibodies against at least two types of HPV (e.g., HPV16 and HPV35, or HPV16, HPV35 and HPV31).

In certain preferred embodiments, the mutated HPV16 L1 protein has a N-terminal truncation of 30 or 40 amino acids compared to the wild-type HPV16 L1 protein.

In certain preferred embodiments, the mutated HPV16 L1 protein has a N-terminal truncation of 30 amino acids compared to the wild-type HPV16 L1 protein.

In certain preferred embodiments, the second type of wild-type HPV is HPV35. In certain preferred embodiments, the amino acid residues at the corresponding positions described in (2) are the amino acid residues at positions 266-288 of the wild-type HPV35 L1 protein.

In certain preferred embodiments, the third-type of wild-type HPV is HPV31. In certain preferred embodiments, the amino acid residues at the corresponding positions described in (3) are the amino acid residues at positions 50-62 of the wild-type HPV31 L1 protein. In certain preferred embodiments, the amino acid residues at the corresponding positions described in (4) are the amino acid residues at positions 127-142 of the wild-type HPV31 L1 protein. In certain preferred embodiments, the amino acid residues at the corresponding positions described in (5) are the amino acid residues at positions 177-182 of the wild-type HPV31 L1 protein.

In certain preferred embodiments, the wild-type HPV 16 L1 protein has an amino acid sequence set forth in SEQ ID NO: 1.

In certain preferred embodiments, the wild-type HPV35 L1 protein has an amino acid sequence set forth in SEQ ID NO: 2.

In certain preferred embodiments, the wild-type HPV31 L1 protein has an amino acid sequence set forth in SEQ ID NO: 3.

In certain preferred embodiments, the sequence of the amino acid residues at positions 266-288 of the wild-type HPV35 L1 protein is set forth in SEQ ID NO: 25.

In certain preferred embodiments, the sequence of amino acid residues at positions 50-62 of the wild-type HPV31 L1 protein is set forth in SEQ ID NO:26.

In certain preferred embodiments, the sequence of amino acid residues at positions 127-142 of the wild-type HPV31 L1 protein is set forth in SEQ ID NO:27.

In certain preferred embodiments, the sequence of amino acid residues at positions 177-182 of the wild-type HPV31 L1 protein is set forth in SEQ ID NO: 28.

In certain preferred embodiments, the mutated HPV16 L1 protein has an amino acid sequence selected from the group consisting of SEQ ID NOs: 7, 9, 10, 11.

In another aspect, the invention provides an isolated nucleic acid encoding the mutated HPV16 L1 protein or variant thereof as described above. In another aspect, the invention provides a vector comprising the isolated nucleic acid. In certain preferred embodiments, the isolated nucleic acid of the invention has a nucleotide sequence selected from the group consisting of SEQ ID NOs: 19, 21, 22, 23.

Vectors useful for insertion of a polynucleotide of interest are well known in the art and include, but are not limited to, cloning vectors and expression vectors. In one embodiment, the vector is, for example, a plasmid, a cosmid, a phage, and the like.

In another aspect, the invention also relates to a host cell comprising the isolated nucleic acid or the vector as described above. Such host cells include, but are not limited to, prokaryotic cells such as *E. coli* cells, and eukaryotic cells such as yeast cells, insect cells, plant cells, and animal cells (e.g., mammalian cells, such as mouse cells, human cells, etc.). The host cell of the invention may also be a cell line, such as a 293T cell.

In another aspect, the present invention relates to an HPV virus-like particle, in which the virus-like particle comprises the mutated HPV16 L1 protein or a variant thereof of the present invention, or consists of or is formed by the mutated HPV16 L1 protein or a variant thereof of the present invention.

In certain preferred embodiments, the HPV virus-like particle of the invention comprises a mutated HPV16 L1 protein, which has a N-terminal truncation of 4-50 amino acids, such as 4, 6, 8, 10, 20, 30 or 40 amino acids, compared to the wild-type HPV16 L1 protein, and has a substitution of amino acid residues at positions 292-316 of the wild-type HPV16 L1 protein with the amino acid residues at positions 266-288 of the wild-type HPV35 L1 protein.

In certain preferred embodiments, the HPV virus-like particle of the invention comprises a mutated HPV16 L1 protein, which has a N-terminal truncation of 4-50 amino acids, such as 4, 6, 8, 10, 20, 30 or 40 amino acids, compared to the wild-type HPV16 protein, and has a substitution of amino acid residues at positions 292-316 of the wild-type HPV16 L1 protein with the amino acid residues at positions 266-288 of the wild-type HPV35 L1 protein, and a substitution of amino acid residues at positions 76-87 of the wild-type HPV16 L1 protein with the amino acid residues at positions 50-62 of the wild-type HPV31 L1 protein.

In certain preferred embodiments, the HPV virus-like particle of the invention comprises a mutated HPV16 L1 protein, which has a N-terminal truncation of 4-50 amino acids, such as 4, 6, 8, 10, 20, 30 or 40 amino acids, compared to the wild-type HPV16 L1 protein, and has a substitution of amino acid residues at positions 292-316 of the wild-type HPV16 L1 protein with the amino acid residues at positions 266-288 of the wild-type HPV35 L1 protein, and a substitution of amino acid residues at positions 152-167 of the wild-type HPV16 L1 protein with the amino acid residues at positions 127-142 of the wild-type HPV31 L1 protein.

In certain preferred embodiments, the HPV virus-like particle of the invention comprises a mutated HPV16 L1 protein, which has a N-terminal truncation of 4-50 amino acids, such as 4, 6, 8, 10, 20, 30 or 40 amino acids, compared to the wild-type HPV16 L1 protein, and has a substitution of amino acid residues at positions 292-316 of the wild-type HPV16 L1 protein with the amino acid residues at positions 266-288 of the wild-type HPV35 L1 protein, and a substitution of amino acid residues at positions 202-207 of the wild-type HPV16 L1 protein with the amino acid residues at positions 177-182 of the wild-type HPV31 L1 protein.

In a particularly preferred embodiment, the HPV virus-like particle of the invention comprises a mutated HPV16 L1 protein having the sequence set forth in SEQ ID NOs: 7, 9, 10 or 11.

In another aspect, the invention also relates to a composition comprising the mutated HPV16 L1 protein or a variant thereof, or the isolated nucleic acid or the vector or the host cell or the HPV virus-like particle. In certain preferred embodiments, the composition comprises the mutated HPV16 L1 protein or a variant thereof of the invention. In certain preferred embodiments, the composition comprises the HPV virus-like particle of the invention.

In another aspect, the invention also relates to a pharmaceutical composition or vaccine comprising the HPV virus-like particle of the invention, optionally further comprising a pharmaceutically acceptable carrier and/or excipient. The pharmaceutical composition or vaccine of the present invention can be used for preventing an HPV infection or a disease caused by an HPV infection such as cervical cancer and condyloma acuminatum.

In certain preferred embodiments, the HPV virus-like particle is present in an amount effective for preventing HPV infection or a disease caused by HPV infection. In certain preferred embodiments, the HPV infection is infection by one or more HPV types (e.g., HPV 16 infection, HPV 35 infection, and/or HPV 31 infection). In certain preferred embodiments, the disease caused by HPV infection is selected from the group consisting of cervical cancer and condyloma acuminatum.

The pharmaceutical composition or vaccine of the invention may be administered by a method well known in the art, for example, but not limited to, administration by oral or injection. In the present invention, a particularly preferred mode of administration is injection.

In certain preferred embodiments, the pharmaceutical composition or vaccine of the invention is administered in a form of a unit dosage. For example, but not intended to limit the invention, the amount of HPV virus-like particle contained in each unit dose is from 5 μg to 80 μg, preferably from 20 μg to 40 μg.

In another aspect, the present invention relates to a method for preparing the mutated HPV16 L1 protein or variant thereof as described above, which comprises expressing the mutated HPV16 L1 protein or variant thereof in a host cell, and then recovering the mutated HPV16 L1 protein or variant thereof from a culture of the host cell.

In certain preferred embodiments, the host cell is *E. coli*.

In certain preferred embodiments, the method comprises the steps of: expressing the mutated HPV16 L1 protein or variant thereof in *E. coli*, and then obtaining the mutated HPV16 L1 protein or a variant thereof by purifying a lysate supernatant of the *E. coli*. In certain preferred embodiments, the mutated HPV16 L1 protein or variant thereof is recovered from the lysate supernatant of the *E. coli* by chromatography (e.g., cation exchange chromatography, hydroxyapatite chromatography, and/or hydrophobic interaction chromatography).

In another aspect, the invention relates to a method for preparing a vaccine, comprising combining the HPV virus-like particle of the invention with a pharmaceutically acceptable carrier and/or excipient.

In another aspect, the present invention relates to a method for preventing HPV infection or a disease caused by HPV infection, comprising administering to a subject a prophylactically effective amount of the HPV virus-like particle or pharmaceutical composition or vaccine according to the present invention. In a preferred embodiment, the HPV infection is infection by one or more HPV types (e.g., HPV 16 infection, HPV 35 infection, and/or HPV 31 infection). In another preferred embodiment, the disease caused by HPV infection includes, but is not limited to, cervical cancer and condyloma acuminatum. In another preferred embodiment, the subject is a mammal, such as a human.

In another aspect, the invention relates to a use of the mutated HPV16 L1 protein or variant thereof or the HPV virus-like particle according to the present invention in the manufacture of a pharmaceutical composition or a vaccine for the prevention of HPV infection or a disease caused by HPV infection. In a preferred embodiment, the HPV infection is infection by one or more HPV types (e.g., HPV 16 infection, HPV 35 infection, and/or HPV 31 infection). In another preferred embodiment, the disease caused by HPV infection includes, but is not limited to, cervical cancer and condyloma acuminatum.

DESCRIPTION AND EXPLANATION OF RELATED TERMS IN THE PRESENT INVENTION

In the present invention, the scientific and technical terms used herein have the meanings commonly understood by those skilled in the art, unless otherwise stated. Moreover, the laboratory procedures of cell culture, molecular genetics, nucleic acid chemistry, and immunology used herein are all routine steps widely used in the corresponding fields. Also, for a better understanding of the present invention, definitions and explanations of related terms are provided below.

According to the invention, the term "a second type of wild-type HPV" means another type of wild-type HPV that is different from HPV16. In the present invention, the second-type of wild-type HPV is preferably wild-type HPV35. According to the invention, the term "a third-type of wild-type HPV" refers to another type of wild-type HPV that is different from HPV 16 and the second-type of wild-type HPV. In the present invention, the third-type of wild-type HPV is preferably wild-type HPV31.

According to the invention, the expression "corresponding position" refers to an equivalent position of the sequences being compared when the sequences are optimally aligned, i.e. the sequences are aligned to obtain a highest percentage of identity.

According to the invention, the term "wild-type HPV16 L1 protein" refers to the major capsid protein L1 naturally present in human papillomavirus type 16 (HPV16). The sequence of the wild-type HPV16 L1 protein is well known in the art and can be found in various public databases (e.g., NCBI database accession numbers ANA05496.1, ANA05539.1, AGC65525.1, AAV91659.1 and AAD33259.1).

In the present invention, when referring to the amino acid sequence of the wild-type HPV16 L1 protein, it is described with reference to the sequence shown in SEQ ID NO: 1. For example, the expression "amino acid residues at positions 292 to 316 of the wild-type HPV16 L1 protein" refers to the amino acid residues at positions 292 to 316 of the polypeptide as set forth in SEQ ID NO: 1. However, it will be understood by those skilled in the art that the wild-type HPV 16 may include a plurality of isolates, and the various isolates may have differences in the amino acid sequences of their L1 proteins. Further, those skilled in the art would understand that although there might be differences in sequence, the L1 proteins of different isolates of HPV 16 have a very high amino acid sequence identity (usually above 95%, such as above 96%, above 97%, above 98%, or above 99%), and have substantially the same biological function. Therefore, in the present invention, the term "wild-type HPV16 L1 protein" includes not only the protein represented by SEQ ID NO: 1, but also the L1 proteins of various HPV16 isolates (for example, HPV16 L1 proteins as shown in ANA05496.1, ANA05539.1, AGC65525.1, AAV91659.1 and AAD33259.1). Also, when a sequence fragment of the wild-type HPV16 L1 protein is described, it includes not only a sequence fragment of SEQ ID NO: 1, but also a corresponding sequence fragment in the L1 proteins of various HPV16 isolates. For example, the expression "amino acid residues at positions 292 to 316 of the wild-type HPV16 L1 protein" includes the amino acid residues at positions 292 to 316 of SEQ ID NO: 1, and the corresponding fragments of the L1 proteins of various HPV16 isolates.

According to the invention, the term "wild-type HPV35 L1 protein" refers to the major capsid protein L1 naturally present in human papillomavirus type 35 (HPV35). The sequence of the wild-type HPV35 L1 protein is well known in the art and can be found in various public databases (e.g., NCBI database accession numbers P27232.2, ACV84022.1, AEI61365.1 AEI61429.1, and ACV84029.1).

In the present invention, when referring to an amino acid sequence of the wild-type HPV35 L1 protein, it is described with reference to the sequence as shown in SEQ ID NO: 2. For example, the expression "amino acid residue at positions 266 to 288 of the wild-type HPV35 L1 protein" refers to the amino acid residues at positions 266 to 288 of the polypeptide represented by SEQ ID NO: 2. However, it will be understood by those skilled in the art that the wild-type HPV35 can include a variety of isolates, and the various isolates may have differences in the amino acid sequences of their L1 proteins. Further, those skilled in the art would understand that although there might be differences in sequence, the L1 proteins of different isolates of HPV35 have a very high amino acid sequence identity (usually above 95%, such as above 96%, above 97%, above 98%, or above 99%), and have substantially the same biological function. Therefore, in the present invention, the term "wild-type HPV35 L1 protein" includes not only the protein represented by SEQ ID NO: 2, but also the L1 proteins of various HPV35 isolates (for example, HPV35 L1 proteins as shown in P27232.2, ACV84022.1, AEI61365.1, AEI61429.1 and ACV84029.1). Also, when a sequence fragment of the wild-type HPV35 L1 protein is described, it includes not only a sequence fragment of SEQ ID NO: 2 but also a corresponding sequence fragment of the L1 proteins of various HPV35 isolates. For example, the expression "amino acid residues at positions 266-288 of the wild-type HPV35 L1 protein" includes the amino acid residues at positions 266-288 of SEQ ID NO: 2, and the corresponding fragments of the L1 proteins of various HPV35 isolates.

According to the invention, the term "wild-type HPV31 L1 protein" refers to the major capsid protein L1 naturally present in human papillomavirus type 31 (HPV31). The sequence of the wild-type HPV31 L1 protein is well known in the art and can be found in various public databases (e.g., NCBI database accession numbers P17388.1, AEI60965.1, ANB49655.1, and AEI61021.1).

In the present invention, when referring to the amino acid sequence of the wild-type HPV31 L1 protein, it is described with reference to the sequence shown in SEQ ID NO: 3. For example, the expression "amino acid residue at positions 177 to 182 of the wild-type HPV31 L1 protein" refers to the amino acid residues at positions 177 to 182 of the polypeptide represented by SEQ ID NO: 3. However, it is understood by those skilled in the art that the wild-type HPV31 may include a plurality of isolates, and the various isolates may have differences in the amino acid sequences of their L1 proteins. Further, those skilled in the art would understand that although there might be differences in sequence, the L1 proteins of different isolates of HPV31 have a very high amino acid sequence identity (usually above 95%, such as above 96%, above 97%, above 98%, or above 99%), and have substantially the same biological function. Therefore, in the present invention, the term "wild-type HPV31 L1 protein" includes not only the protein represented by SEQ ID NO: 3, but also the L1 proteins of various HPV31 isolates (for example, HPV31 L1 proteins as shown in P17388.1, AEI60965.1, ANB49655.1 and AEI61021.1). Also, when a sequence fragment of the wild-type HPV31 L1 protein is described, it includes not only the sequence fragment of SEQ ID NO: 3, but also a corresponding sequence fragment of the L1 proteins of various HPV31 isolates. For example, the expression "amino acid residues at positions 177 to 182 of the wild-type HPV31 L1 protein" includes the amino acid residues at positions 177 to 182 of SEQ ID NO: 3, and the corresponding fragments of the L1 proteins of various HPV31 isolates.

According to the invention, the expression "corresponding sequence fragment" or "corresponding fragment" refers to a fragment that are located at an equivalent position of the sequences being compared when the sequences are optimally aligned, i.e. the sequences are aligned to obtain a highest percentage of identity.

According to the invention, the expression "N-terminal truncation of X amino acids" refers to that the amino acid residues at positions 1 to X of the N-terminus of a protein are substituted with methionine residue encoded by an initiation codon (for initiation of protein translation). For example, a HPV16 L1 protein having a N-terminal truncation of 30 amino acids refers to a protein obtained by substituting the amino acid residues at positions 1 to 30 of the N-terminus of the wild-type HPV16 L1 protein with a methionine residue encoded by an initiation codon.

According to the invention, the term "variant" refers to a protein whose amino acid sequence has substitution (preferably conservative substitution), addition or deletion of one or several (e.g. 1, 2, 3, 4, 5, 6, 7, 8 or 9) amino acids, or has an identity of at least 90%, 95%, 96%, 97%, 98%, or 99%, as compared with the mutated HPV16 L1 protein according to the invention (for example, the protein as set forth in SEQ ID NO: 7, 9, 10 and 11), and which retains the function of the mutated HPV16 L1 protein. In the present invention, the term "function of the mutated HPV16 L1 protein" refers to a capability of inducing generation of neutralizing antibodies against at least two HPV types (e.g. HPV16 and HPV35, or HPV16, HPV35 and HPV31) in the body. The term "identity" is a measure of similarity between nucleotide sequences or amino acid sequences. Generally, sequences are aligned to get the maximum match. "Identity" itself has a meaning that is well known in the art and can be calculated using published algorithms such as BLAST.

According to the invention, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by for example using a computer program such as Align program (DNAstar, Inc.) which is based on the method of Needleman, et al. (J. Mol. Biol. 48:443-453, 1970). The percentage of identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, and with a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and with a gap weight of 16, 14, 12, 10, 8, 6, or 4 and a length weight of 1, 2, 3, 4, 5, or 6.

As used herein, the term "conservative substitution" refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having basic side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, generally a conservative substitution refers to a substitution of a corresponding amino acid residue with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

According to the invention, the term "E. coli expression system" refers to an expression system consisting of E. coli (strain) and a vector, wherein the E. coli (strain) is derived from the commercially available strains, including, but not limited to: ER2566, BL21 (DE3), B834 (DE3), and BLR (DE3).

According to the invention, the term "vector" refers to a nucleic acid carrier tool which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, etc.

According to the invention, the term "a pharmaceutically acceptable carrier and/or excipient" refers to a carrier and/or excipient that is pharmacologically and/or physiologically compatible to a subject and active ingredients, which is well known in the art (see, for example, Remington's Pharmaceutical Sciences. Edited by Gennaro A R, 19th ed. Pennsylvania: Mack Publishing Company, 1995), including, but not limited to: pH regulators, surfactants, adjuvants, and ionic strength enhancers. For example, pH regulators include, but are not limited to, phosphate buffers; surfactants include, but are not limited to: cation surfactants, anion surfactants, or non-ionic surfactants, e.g., Tween-80; adjuvants include, but are not limited to, aluminium adjuvant (e.g., aluminium hydroxide), and Freund's adjuvant (e.g., Freund's complete adjuvant); and ionic strength enhancers include, but are not limited to, NaCl.

According to the invention, the term "an effective amount" refers to an amount that can effectively achieve the intended purpose. For example, an amount effective for preventing a disease (such as HPV infection) refers to an amount effective for preventing, suppressing, or delaying the occurrence of a disease (such as HPV infection). The determination of such an effective amount is within the ability of a person skilled in the art.

According to the invention, the term "chromatography" includes, but is not limited to: ion exchange chromatography (such as cation-exchange chromatography), hydrophobic interaction chromatography, absorbent chromatography (such as hydroxyapatite chromatography), gel filtration chromatography (gel exclusion chromatography), and affinity chromatography.

According to the invention, the term "lysate supernatant" refers to a solution produced by the following steps: host cells (such as E. coli) are disrupted in a lysis buffer, and the insoluble substances are then removed from the lysed solution containing the disrupted host cells. Various lysis buffers are well known in the art, including, but not limited to Tris buffers, phosphate buffers, HEPES buffers, MOPS buffers, etc. In addition, the disrupting of a host cell can be accomplished by methods well known by a person skilled in the art, including, but not limited to homogenizer disrupting, ultrasonic treatment, grinding, high pressure extrusion, lysozyme treatment, etc. Methods for removing insoluble substances are also well known by a person skilled in the art, including, but not limited to filtration and centrifugation.

Beneficial Effects of the Invention

Studies have shown that although there is a certain cross-protection between HPV16 and other types of HPV (such as HPV35 and HPV31), such cross-protection has poor potency, which is usually less than one hundredth, even one thousandth of the protection level of VLP of its own type. Therefore, a subject vaccinated with HPV16 vaccine still has a high risk of being infected with other types of HPV (such as HPV35 and HPV31).

The present invention provides a mutated HPV16 L1 protein and a HPV virus-like particle formed thereby. The HPV virus-like particle of the present invention is capable of providing a significant cross-protection between HPV 16 and other types of HPV (e.g., HPV 35 and HPV 31). In particular, at the same immunizing dose, the HPV virus-like particle of the invention is capable of inducing the generation of high-titer neutralizing antibodies against at least two types of HPV (e.g., HPV 16 and HPV 35, or HPV 16, HPV 35 and HPV 31) in the body, and its effect is comparable to a mixture of VLPs of multiple types of HPV (e.g., a mixture of HPV16 VLP and HPV35 VLP, or a mixture of HPV16 VLP, HPV35 VLP, and HPV31 VLP). Therefore, the HPV virus-like particle of the present invention can be used to simultaneously prevent infections by at least two types of HPV (for example, HPV16 and HPV35, or HPV16, HPV35, and HPV31) and a disease associated therewith, and has significant advantageous technical effects. This has a particularly significant advantage in expanding the scope of protection of HPV vaccines and reducing the cost of production of HPV vaccines.

The embodiments of the present invention will be described in detail below with reference to the accompanying drawings and embodiments. However, those skilled in the art will understand that the following drawings and examples are merely illustrative of the invention and are not intended to limit the scope of the invention. According to following detailed description of the drawings and preferred embodiments, the various objects and advantageous aspects of the invention will be apparent to those skilled in the art.

DESCRIPTION OF THE DRAWINGS

FIG. 3A: HPV16N30; FIG. 3B: HPV35 L1; FIG. 3C: HPV31 L1; FIG. 3D: H16N30-35T1; FIG. 3E: H16N30-35T2; FIG. 3F: H16N30-35T3; FIG. 3G: H16N30-35T4; FIG. 3H: H16N30-35T5; FIG. I: H16N30-35T4-31S1; FIG. 3J: H16N30-35T4-31S2; FIG. 3K: H16N30-35T4-31S3; FIG. 3L: H16N30-35T4-31S5. The results showed that the first protein peaks of each sample appeared at around 12 min, which were comparable to that of the VLP assembled from HPV16N30 protein (HPV16N30 VLP), the VLP assembled from HPV35 L1 protein (HPV35 VLP), and the VLP assembled from HPV31 L1 protein (HPV31 VLP). This indicates that all of the above mutated proteins can be assembled into VLPs.

FIG. 4A, HPV16N30 VLP; FIG. 4B, HPV35 VLP; FIG. 4C, HPV31 VLP; FIG. 4D, H16N30-35T1 VLP; FIG. 4E, H16N30-35T2 VLP; FIG. 4F, H16N30-35T3 VLP; FIG. 4G, H16N30-35T4 VLP; FIG. 4H, H16N30-35T5 VLP; FIG. 4I, H16N30-35T4-31S1 VLP; FIG. 4J, H16N30-35T4-31S2 VLP; FIG. 4K, H16N30-35T4-31S3 VLP; FIG. 4L, H16N30-35T4-31S5 VLP. The results showed that the sedimentation coefficients of the H16N30-35T1 VLP, H16N30-35T2 VLP, H16N30-35T3 VLP, H16N30-35T4 VLP, H16N30-35T5 VLP, H16N30-35T4-31S1 VLP, H16N30-35T4-31S2 VLP, H16N30-35T4-31S3 VLP, H16N30-35T4-31S5 VLP are similar to those of the HPV16N30 VLP, HPV35 VLP, and HPV31 VLP. This indicates that the H16N30-35T1, H16N30-35T2, H16N30-35T3, H16N30-35T4, H16N30-35T5, H16N30-35T4-31S1, H16N30-35T4-31 S2, H16N30-35T4-31S3, H16N30-35T4-31 S5 are assembled into virus-like particles similar to wild-type VLP in terms of size and morphology.

FIG. 5A, VLP assembled by HPV16N30; FIG. 5B, VLP assembled by HPV35 L1; FIG. 5C, VLP assembled by HPV31 L1; FIG. 5D, VLP assembled by H16N30-35T1; FIG. 5E, VLP assembled by H16N30-35T2; FIG. 5F, VLP assembled by H16N30-35T3; FIG. 5G, VLP assembled by H16N30-35T4; FIG. 5H, VLP assembled by H16N30-35T5; FIG. 5I, VLP assembled by H16N30-35T4-31S1; FIG. 5J, VLP assembled from H16N30-35T4-31S2; FIG. 5K, VLP assembled from H16N30-35T4-31S3; FIG. 5L, VLP assembled from H16N30-35T4-31S5. The results showed that the H16N30-35T1, H16N30-35T2, H16N30-35T3, H16N30-35T4, H16N30-35T5, H16N30-35T4-31S1, H16N30-35T4-31S2, H16N30-35T4-31S3 and H16N30-35T4-31S5 are similar to HPV16N30, HPV35 L1 and HPV31 L1 proteins, and can be assembled into VLPs with a radius of about 30 nm.

FIG. 6A, HPV16N30 VLP; FIG. 6B, HPV35 VLP; FIG. 6C, HPV31 VLP; FIG. 6D, H16N30-35T1 VLP; FIG. 6E, H16N30-35T2 VLP; FIG. 6F, H16N30-35T3 VLP; FIG. 6G, H16N30-35T4 VLP; FIG. 6H, H16N30-35T5 VLP; FIG. 6I, H16N30-35T4-31S1 VLP; FIG. 6J, H16N30-35T4-31S2 VLP; FIG. 6K, H16N30-35T4-31S3 VLP; FIG. 6L, H16N30-35T4-31S5 VLP. The results indicate that the VLP formed by each protein has extremely high thermal stability.

FIG. 8A: 10 μg dose group (immunization dose was 10 μg, using aluminum adjuvant); FIG. 8B: 1 μg dose group (immunization dose was 1 μg, using aluminum adjuvant); FIG. 8C: 0.1 μg dose group (immunization dose was 0.1 μg, using aluminum adjuvant). The results showed that the H16N30-35T4 VLP induced high titers of neutralizing antibodies against HPV16 in mice, and its protective effect was comparable to those of the HPV16N30 VLP alone and the mixed HPV16/HPV35 VLP at the same dose, and was significantly better than that of the HPV35 VLP alone at the same dose; and it also induced high titers of neutralizing antibodies against HPV35 in mice, and its protective effect was comparable to those of the HPV35 VLP alone and the mixed HPV16/HPV35 VLP at the same dose, and was significantly better than that of the HPV16N30 VLP alone at the same dose. This indicates that the H16N30-35T4 VLP has good cross-immunogenicity and cross-protection against HPV16 and HPV35.

FIG. 8D: 10 μg dose group (immunization dose was 10 μg, using aluminum adjuvant); FIG. 8E: 1 μg dose group (immunization dose was 1 μg, using aluminum adjuvant); FIG. 8F: 0.1 μg dose group (immunization dose was 0.1 μg, using aluminum adjuvant). The results showed that the H16N30-35T4-31S3 VLP induced high titers of neutralizing antibodies against HPV16 in mice, and its protective effect was comparable to those of the HPV16N30 VLP alone and the mixed HPV16/HPV35/HPV31 VLP at the same dose, and was significantly better than that of the HPV35 VLP alone or the HPV31 VLP alone at the same dose; and it also induced high titers of neutralizing antibodies against HPV35 in mice, and its protective effect was comparable to those of the HPV35 VLP alone and the mixed HPV16/HPV35/HPV31 VLP at the same dose, and was significantly better than that of the HPV16N30 VLP alone or the HPV31 VLP alone at the same dose, and also it induced high titers of neutralizing antibodies against HPV31 in mice, and its protective effect was comparable to those of the HPV31 VLP alone and the mixed HPV16/HPV35/HPV31 VLP, and was significantly better than that of the HPV16N30 VLP alone or the HPV35 VLP alone at the same dose. This indicates that the H16N30-35T4-S3 VLP has good cross-immunogenicity and cross-protection against HPV16, HPV35 and HPV31.

SEQUENCE INFORMATION

Figure 1:
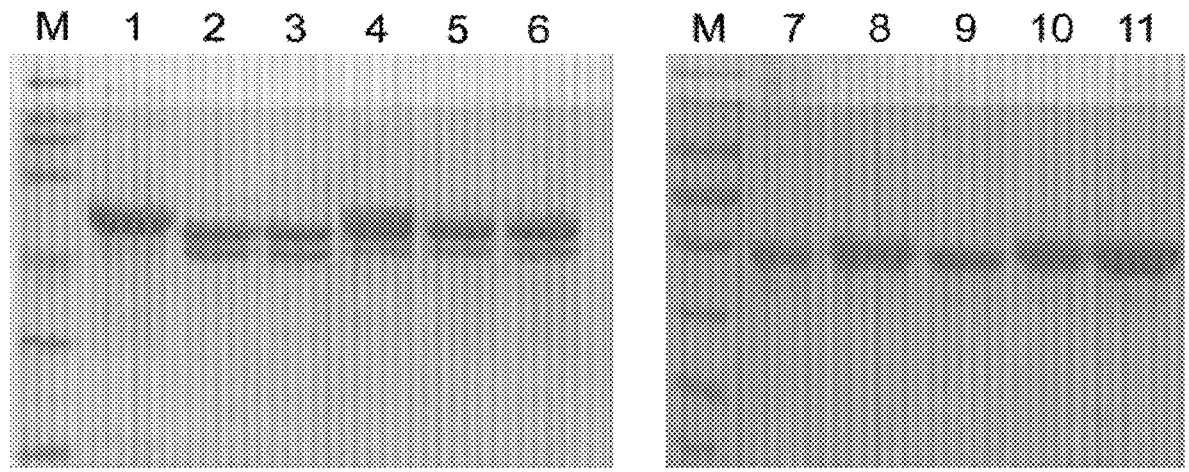
FIG. 1 shows the results of SDS polyacrylamide gel electrophoresis of the purified mutated protein in Example 1. Lane M: protein molecular weight marker; Lane 1: HPV16N30 (HPV16 L1 protein with N-terminal truncation of 30 amino acids); Lane 2: H16N30-35T1; Lane 3: H16N30-35T2; Lane 4: H16N30-35T3; Lane 5: H16N30-35T4; Lane 6: H16N30-35T5; Lane 7: HPV16N30; Lane 8: H16N30-35T4-31S1; Lane 9: H16N30-35T4-31S2; Lane 10: H16N30-35T4-31S3; Lane 11: H16N30-35T4-31S5. The results showed that after purification by chromatography, the proteins H16N30-35T1, H16N30-35T2, H16N30-35T3, H16N30-35T4, H16N30-35T5, H16N30-35T4-31S1, H16N30-35T4-31S2, H16N30-35T4-31S3, H16N30-35T4-31S5 have a purity of not less than 95%.

Some of the sequences involved in the present invention are provided in Table 1 below.

TABLE 1

Description of sequences

| SEQ ID NO: | Description |
| --- | --- |
| 1 | wild-type HPV16 L1 protein |
| 2 | wild-type HPV35 L1 protein |
| 3 | wild-type HPV31 L1 protein |
| 4 | The mutated HPV16 L1 protein containing Segment 1 of HPV35 L1 protein, H16N30-35T1 |
| 5 | The mutated HPV16 L1 protein containing Segment 2 of HPV35 L1 protein, H16N30-35T2 |
| 6 | The mutated HPV16 L1 protein containing Segment 3 of HPV35 L1 protein, H16N30-35T3 |
| 7 | The mutated HPV16 L1 protein containing Segment 4 of HPV35 L1 protein, H16N30-35T4 |
| 8 | The mutated HPV16 L1 protein containing Segment 5 of HPV35 L1 protein, H16N30-35T5 |
| 9 | The mutated HPV16 L1 protein containing Segment 4 of HPV35 L1 protein and Segment 1 of HPV31 L1 protein, H16N30-35T4-31S1 |
| 10 | The mutated HPV16 L1 protein containing Segment 4 of HPV35 L1 protein and Segment 2 of HPV31 L1 protein, H16N30-35T4-31S2 |
| 11 | The mutated HPV16 L1 protein containing Segment 4 of HPV35 L1 protein and Segment 3 of HPV31 L1 protein, H16N30-35T4-31S3 |
| 12 | The mutated HPV16 L1 protein containing Segment 4 of HPV35 L1 protein and Segment 5 of HPV31 L1 protein, H16N30-35T4-31S5 |
| 13 | DNA sequence encoding SEQ ID NO: 1 |
| 14 | DNA sequence encoding SEQ ID NO: 2 |
| 15 | DNA sequence encoding SEQ ID NO: 3 |
| 16 | DNA sequence encoding SEQ ID NO: 4 |
| 17 | DNA sequence encoding SEQ ID NO: 5 |
| 18 | DNA sequence encoding SEQ ID NO: 6 |
| 19 | DNA sequence encoding SEQ ID NO: 7 |
| 20 | DNA sequence encoding SEQ ID NO: 8 |
| 21 | DNA sequence encoding SEQ ID NO: 9 |
| 22 | DNA sequence encoding SEQ ID NO: 10 |
| 23 | DNA sequence encoding SEQ ID NO: 11 |
| 24 | DNA sequence encoding SEQ ID NO: 12 |
| 25 | Sequence of amino acid residues at positions 266-288 of wild-type HPV35 L1 protein |
| 26 | Sequence of amino acid residues at positions 50-62 of wild-type HPV31 L1 protein |
| 27 | Sequence of amino acid residues at positions 127-142 of wild-type HPV31 L1 protein |
| 28 | Sequence of amino acid residues at positions 177-182 of wild-type HPV31 L1 protein |

```
Sequence 1 (SEQ ID NO: 1):
MQVTFIYILVITCYENDVNVYHIFFQMSLWLPSEATVYLPPVPVSKVV

STDEYVARTNIYYHAGTSRLLAVGHPYFPIKKPNNNKILVPKVSGLQY

RVFRIFILPDPNKFGFPDTSFYNPDTQRLVWACVGVEVGRGQPLGVGI

SGHPLLNKLDDTENASAYAANAGVDNRECISMDYKQTQLCLIGCKPPI

GEHWGKGSPCTNVAVNPGDCPPLELINTVIQDGDMVDTGFGAMDFTTL
```

-continued
QANKSEVPLDICTSICKYPDYIKMVSEPYGDSLFFYLRREQMFVRHLE

NRAGAVGDNVPDDLYIKGSGSTANLASSNYFPTPSGSMVTSDAQIFNK

PYWLQRAQGHNNGICWGNQLFVTVVDTTRSTNIVISLCAAISTSETTY

KNTNFKEYLRHGEEYDLQFIFQLCKITLTADIVITYIHSMNSTILEDW

NFGLQPPPGGTLEDTYRFVTSQAIACQKHTPPAPKEDPLKKYTFWEVN

LKEKFSADLDQFPLGRKFLLQAGLEAKPKFTLGKRKATPTTSSTSTTA

KRKKRKL

Sequence 2 (SEQ ID NO: 2):
MSLWRSNEATVYLPPVSVSKVVSTDEYVTRTNIYYHAGSSRLLAVGHP

YYAIKKQDSNKIAVPKVSGLQYRVFRVKLPDPNKFGFPDTSFYDPASQ

RLVWACTGVEVGRGQPLGVGISGHPLLNKLDDTENSNKYVGNSGTDNR

ECISMDYKQTQLCLIGCRPPIGEHWGKGTPCNANQVKAGECPPLELLN

TVLQDGDMVDTGFGAMDFTTLQANKSDVPLDICSSICKYPDYLKMVSE

PYGDMLFFYLRREQMFVRITLFNRAGTVGETVPADLYIKGTTGTLPST

SYFPTPSGSMVTSDAQIFNKPYWLQRAQGHNNGICWSNQLFVTVVDTT

RSTNMSVCSAVSSSDSTYKNDNFICEYLRHGEEYDLQFIFQLCKITLT

PADVMTYIHSMNPSILEDWNFGLTPPSGTLEDTYRYVISQAVTCQKPS

APKPKDDPLKNYTFWEVDLKEKFSADLDQFPLGRKFLLQAGLKARPNF

RLGKRAAPASTSKKSSTKRRKVKS

Sequence 3 (SEQ ID NO: 3):
MSLWRPSEATVYLPPVSVSKVVSTDEYVTRTNIYYHAGSARLLTVGHP

YYSIPKSDNPKKIVVPKVSGLQYRVFRVRLPDPNKFGFPDTSFYNPET

QRLVWACVGLEVGRGQPLGVGISGHPLLNKFDDTENSNRYAGGPGTDN

RECISMDYKQTQLCLLGCKPPIGEHWGKGSPCSNNAITPGDCPPLELK

NSVIQDGDIVIVDTGFGAMDFTALQDTKSNVPLDICNSICKYPDYLKM

VAEPYGDTLFFYLRREQMFVRHFFNRSGTVGESVPTDLYIKOSGSTAT

LANSTYFPTPSGSMVTSDAQTFNKPYWMQRAQGHNNGICWGNQLFVTV

VDTTRSTNMSVCAAIANSDTTFKSSNFKEYLRHGEEFDLQFIFQLCKI

TLSADIMTYIHSMNPAILEDWNFGLTTPPSGSLEDTYRFVTSQAITCQ

KTAPQKPKEDPFKDYVFWEVNLKEKFSADLDQFPLGRKFLLQAGYRAR

PKFKAGKRSAPSASTTTPAKRKKTKK

Sequence 4 (SEQ ID NO: 4):
MLPSEATVYLPPVPVSKVVSTDEYVARTNIYYHAGTSRLLAVGHPYYA

IKKQDSNKIAVPKVSGLQYRVFRIHLPDPNKFGFPDTSFYNPDTQRLV

WACVGVEVGRGQPLGVGISGHPLLNKLDDTENASAVAANAGVDNRECI

SMDYKQTQLCLIGCKPPIGEHWGKGSPCTNVAVNPGDCPPLELINTVI

QDGDMVDTGFGAMDFTTLQANKSEVPLDICTSICKYPDYIKMVSEPYG

DSLFFYLRREQMYVRIELFNRAGAVGDNVPDDLYIKGSGSTANLASSN

YFPTPSGSMVTSDAWNICPYWLQRAQGHNNGICWGNQLFVTVVDTTRS

TNIVISLCAAISTSETTYKNTNFKEYLRHGEEYDLQFIFQLCKITLTA

DIMTYIHSMNSTILEDWNFGLQPPPGGTLEDTYRFVTSQAIACQKHTP

PAPKEDPLKKYTFWEVNLKEKFSADLDQFPLGRKFLLQAGLEAKPKFT

LGKRKATPTTSSTSTTAKRKKRKL

Sequence 5 (SEQ ID NO: 5):
MLPSEATVYLPPVPVSKVVSTDEYVARTNIYYHAGTSRLLAVGHIPYF

PIKKPNNNKILVPKVSGLQYRVFRITILPDPNKFGFPDTSFYNPDTQR

LVWACGVGVEVGRGQPLGVGISGHPLLNKLDDTENSNKYVGNSGTDNRE

CISMDYKQTQLCLIGCKPPIGEHVVGKGSPCTNVAVNPGDCPPLELIN

TVIQDGDMVDTGFGAMDFTTLQANKSEVPLDICTSICKYPDYIKMVSE

PYGDSLFFYLRREQMFVRHLFNRAGAVGDNVPDDLYIKGSGSTANLAS

SNYFPTPSGSMVTSDAQIFNKPYWLQRAQGHNNGICWGNQLFVTVVDT

TRSTNIVISLCAAISTSETTYKNTNFKEYLRHGEEYDLQFIFQLCKIT

LTADIMTYIHSMNSTILEDWNFGLQPPPGGTLEDTYRFVTSQAIACQK

HTPPAPKEDPLKKYTFWEVNLKEKFSADLDQFPLGRKFLLQAGLEAKP

KFTLGKRKATPTTSSTSTTAKRKKRKL

Sequence 6 (SEQ ID NO: 6):
MLPSEATVYLPPVPVSKVVSTDEYVARTNIYYHAGTSRLLAVGHPYFP

IKKPNNNKILVPKVSGLQYRVFRIHLPDPNKFGFPDTSFYNPDTQRLV

WACVGVEVGRGQPLGVGISGHPLLNKLDDTENASAVAANAGVDNRECI

SMDYKQTQLCLIGCKPPIGEHWGKGTPCNANQVKAGECPPLELINTVI

QDGDMVDTGFGAMDFTTLQANKSEVPLDICTSICKYPDYIKMVSEPYG

DSLFFYLRREQMFVRHLFNRAGAVGDNVPDDLY1KGSGSTANLASSNY

FPTPSGSMVTSDAQIFNKPYWLQRAQGHNNGICWGNQLFVTVVDTTRS

TNIVISLCAAISTSETTYKNTNFKEYLRHGEEYDLQFIFQLCKITLTA

DIMTYIHSMNSTILEDWNFGLQPPPGGTLEDTYRFVTSQAIACQKHTP

PAPKEDPLKKYTFWEVNLKEKFSADLDQFPLGRKFLLQAGLEAKPKFT

LGKRKATPTTSSTSTTAKRKKRKL

Sequence 7 (SEQ ID NO: 7):
MLPSEATVYLPPVPVSKVVSTDEYVARTNIYYHAGTSRLLAVGHPYFP

IKKPNNNKILVPKVSGLQYRVFRIHLPDPNKFGFPDTSFYNPDTQRLV

WACVGVEVGRGQPLGVGISGHPLLNKLDDTENASAVAANAGVDNRECI

SMDYKQTQLCLIGCKPPIGEHWGKGSPCTNVAVNPGDCPPLELINTVI

QDGDMVDTGFGAMDFTTLQANKSEVPLDICTSICKYPDYIKMVSEPYG

DSLFFYLRREQMFVRHLENRAGTVGETVPADLYIKGTTGTLPSTSYFP

TPSGSMVTSDAQWNKPYWLQRAQGHNNGICWSNQLFVTVVDTTRSTNM

SLCAAISTSETTYKNTNFKEYLRHGEEYDLQFWQLCKITLTADIIVIT

YWISMNSTILEDWNEGLQPPPGGTLEDTYREVTSQAIACQICHTPPAP

KEDPLKKYTFWEVNLKEKESADLDQFPLGRKFLLQAGLEAKPKFTLGK

RKATPTTSSTSTTAKRKKRKL

Sequence 8 (SEQ ID NO: 8):
MLPSEATVYLPPVPVSKVVSTDEYVARTNIYYHAGTSRLLAVGHPYFP

IKKPNJKILVPKVSGLQYRVERIHLPDPNKFGFPDTSFYNPDTQRLVW

ACVGVEVGRGQPLGVGISGHPLLNKLDDTENASAYAANAGVDNRECIS

MDYKQTQLCLIGCKPPIGEHWGKGSPCTNVAVNPGDCPPLELINTVIQ
DGDMVDTGFGAMDFTTLQANKSEVPLDICTSICKYPDYIKMVSEPYGD
SLFFYLRREQMFVRHLENRAGAVGDNVPDDLYIKGSGSTANLASSNYF
PTPSGSMVTSDAQWNKPYWLQRAQGHNNGICWSNQLFVTVVDTTRSTN
MSLCAAVSSSDSTYKNDNFKEYLRHGEEYDLQFIFQLCKITLTADWIT
YIHSMNSTILEDWNEGLQPPPGGTLEDTYREVTSQAIACQKHTPPAPK
EDPLKKYTFWEVNLKEKFSADLDQFPLGRKFLLQAGLEAKPKFTLGKR
KATPTTSSTSTTAKRKKRKL

Sequence 9 (SEQ ID NO: 9):
MLPSEATVYLPPVPVSKVVSTDEYVARTNIYYHAGTSRLLAVGITPYY
STPKSDNPKKIVVPKVSGLQYRVERIHLPDPNKFGFPDTSFYNPDTQR
LVWACVGVEVGRGQPLGVGISGHPLLNKLDDTENASAYAANAGVDNRE
CISMDYKQTQLCLIGCKPPIGEHWGKGSPCTNVAVNPGDCPPLELINT
VIQDGDMVDTGEGAMDFTTLQANKSEVPLDICTSICKYPDYIKMVSEP
YGDSLFFYLRREQMFVRHLENRAGTVGETVPADLYIKGTTGTLPSTSY
FPTPSGSMVTSDAQIFNICPYWLQRAQGHNNGICWSNQLFVTVVDTTR
STNIVISLCAAISTSETTYKNTNEKEYLRHGEEYDLQFIFQLCKITLT
ADIMTYIHSMNSTILEDWNEGLQPPPGGTLEDTYRFVTSQAIACQKHT
PPAPKEDPLKKYTFWEVNLKEKFSADLDQFPLGRKFLLQAGLEAKPKF
TLGKRKATPTTSSTSTTAKRKKRKL Sequence 10 (SEQ ID NO: 10):
MLPSEATVYLPPVPVSKVVSTDEYVARTNIYYHAGTSRLLAVGHPYFP
IKKPNNNKILVPKVSGLQYRVFRIHLPDPNKFGFPDTSFYNPDTQREV
WACVGVEVGRGQPLGVGISGHPLLNKFDDTENSNRYAGGPGTDNRECI
SMDYKQTQLCLIGCKPPIGEHWGKGSPCTNVAVNPGDCPPLELINTVI
QDGDMVDTGFGAMDFTTLQANKSEVPLDICTSICKYPDYIKMVSEPYG
DSLFFYLRREQMFVRHLFNRAGTVGETVPADEYIKGTTGTLPSTSYFP
TPSGSMVTSDAQIFNKPYWLQRAQGHNNGICWSNQLFVTVVDTTRSTN
MSLCAAISTSETTYKNTNFKEYLRHGEEYDLQFIFQLCKITLTADIMT
YIHSMNSTILEDWNFGLQPPPGGTLEDTYRFVTSQAIACQKHTPPAPK
EDPLKKYTFWEVNLKEKFSADLDQFPLGRKFLLQAGLEAKPKFTLGKR
KATPTTSSTSTTAKRKKRKL Sequence 11 (SEQ ID NO: 11):
MLPSEATVYLPPVPVSKVVSTDEYVARTNIYYHAGTSRLLAVGFIPYF
PIKKPNNNKILVPKVSGLQYRVFRIHLPDPNKFGFPDTSFYNPDTQRL
VWACVGVEVGRGQPLGVGISGFIPLLNKLDDTENASAYAANAGVDNRE
CISMDYKQTQLCLIGCKPPIGEHWGKGSPCSNNAITPGDCPPLELINT
VIQDGDMVDTGFGAMDFTTLQANKSEVPLDICTSICKYPDYIKMVSEP
YGDSLFFYLRREQMFVRHLFNRAGTVGETVPADLYIKGTTGTLPSTSY
FPTPSGSMVTSDAQIFNKPYWLQRAQGHNNGICWSNQLFVTVVDTTRS
TNMSLCAAISTSETTYKNTNFKEYLRHGEEYDLQFIFQLCKITLTADI
MTYIHSMNSTILEDWNFGLQPPPGGTLEDTYRFVTSQAIACQKHTPPA
PKEDPLKKYTFWEVNLKEKFSADLDQFPLGRKFLLQAGLEAKPKFTLG
KRKATPTTSSTSTTAKRKKRKL Sequence 12 (SEQ ID NO: 12):
MLPSEATVYLPPVPVSKVVSTDEYVARTNIYYHAGTSRLLAVGHPYFP
IKKPNNNKILVPKVSGLQYRVFRIHLPDPNKFGFPDTSFYNPDTQRLV
WACVGVEVGRGQPLGVGISGHPLLNKLDDTENASAYAANAGVDNRECI
SMDYKQTQLCLIGCKPPIGEHWGKGSPCTNVAVNPGDCPPLELINTVI
QDGDMVDTGFGAMDFTTLQANKSEVPLDICTSICKYPDYIKMVSEPYG
DSLFFYLRREQMFVRHLFNRAGTVGETVPADLYIKGTTGTLPSTSYFP
TPSGSMVTSDAQIFNKPYWLQRAQGHNNGICWSNQLFVTVVDTTRSTN
MSLCAAIANSDTTFKSSNFKEYLRHGEEYDLQHFQLCKITLTADIMTY
IFISMNSTILEDWNFGLQPPPGGTLEDTYRFVTSQAIACQKHTPPAPK
EDPLKKYTFWEVNLKEKFSADLDQFPLGRKFLLQAGLEAKPKFTLGKR
KATPTTSSTSTTAKRKKRKL Sequence 13 (SEQ ID NO: 13):
ATGCAGGTGACTTTTATTTACATCCTAGTTATTACATGTTACGAAAAC
GACGTAAACGTTTACCATATTTTTTTTCAGATGTCTCTTTGGCTTCCT
AGTGAGGCCACTGTCTACTTGCCTCCTGTCCCAGTATCTAAGGTTGTA
AGCACGGATGAATATGTTGCACGCACAAACATATATTATCATGCAGGA
ACATCCAGACTACTTGCAGTTGGACATCCCTATTTTCCTATTAAAAAA
CCTAACAATAACAAAATATTAGTTCCTAAAGTATCAGGATTACAATAC
AGGGTATTTAGAATACATTTACCTGACCCCAATAAGTTTGGTTTTCCT
GACACCTCATTTTATAATCCAGATACACAGCGGCTGGTTTGGGCCTGT
GTAGGTGTTGAGGTAGGTCGTGGTCAGCCATTAGGTGTGGGCATTAGT
GGCCATCCTTTATTAAATAAATTGGATGACACAGAAAATGCTAGTGCT
TATGCAGCAAATGCAGGTGTGGATAATAGAGAATGTATATCTATGGAT
TACAAACAAACACAATTGTGTTTAATTGGTTGCAAACCACCTATAGGG
GAACACTGGGGCAAAGGATCCCCATGTACCAATGTTGCAGTAAATCCA
GGTGATTGTCCACCATTAGAGTTAATAAACACAGTTATTCAGGATGGT
GATATGGTTGATACTGGCTTTGGTGCTATGGACTTTACTACATTACAG
GCTAACAAAGTGAAGTTCCACTGGATATTTGTACATCTATTTGCAAA
TATCCAGATTATATTAAAATGGTGTCAGAACCATATGGCGACAGCTTA
TTTTTTTATCTACGAAGGGAACAAATGTTTGTTAGACATTTATTTAAT
AGGGCTGGTGCTGTTGGTGATAATGTACCAGACGATTTATACATTAAA
GGCTCTGGGTCTACTGCAAATTTAGCCAGTTCAAATTATTTTCCTACA
CCTAGTGGTTCTATGGTTACCTCTGATGCCCAAATATTCAATAAACCT
TACTGGTTACAACGAGCACAGGGCCACAATAATGGCATTTGTTGGGT
AACCAACTATTTGTTACTGTTGTTGATACTACACGCAGTACAAATATG
TCATTATGTGCTGCCATATCTACTTCAGAAACTACATATAAAAATACT
AACTTTAAGGAGTACCTACGACATGGGGAGGAATATGATTTACAGTTT
ATTTTTCAACTGTGCAAAATAACCTTAACTGCAGACATTATGACATAC
ATACATTCTATGAATTCCACTATTTTGGAGGACTGGAATTTTGGTCTA

CAACCTCCCCCAGGAGGCACACTAGAAGATACTTATAGGTTTGTAACA

TCCCAGGCAATTGCTTGTCAAAAACATACACCTCCAGCACCTAAAGAA

GATCCCCTTAAAAAATACACTTTTTGGGAAGTAAATTTAAAGGAAAAG

TTTTCTGCAGACCTAGATCAGTTTCCTTTAGGACGCAAATTTTTACTA

CAAGCAGGATTGGAGGCCAAACCAAAATTTACATTAGGAAAACGAAAA

GCTACACCCACCACCTCATCTACCTCTACAACTGCTAAACGCAAAAAA

CGTAAGCTGTAA

Sequence 14 (SEQ ID NO: 14):
ATGAGCCTGTGGAGGAGCAACGAGGCCACCGTGTACCTGCCCCCCGTG

AGCGTGAGCAAGGTGGTGAGCACCGACGAGTACGTGACCAGGACCAAC

ATCTACTACCACGCCGGCAGCAGCAGGCTGCTGGCCGTGGGCCACCCC

TACTACGCCATCAAGAAGCAGGACAGCAACAAGATCGCCGTGCCCAAG

GTGAGCGGCCTGCAGTACAGGGTGTTCAGGGTGAAGCTGCCCGACCCC

AACAAGTTCGGCTTCCCCGACACCAGCTTCTACGACCCCGCCAGCCAG

AGGCTGGTGTGGGCCTGCACCGGCGTGGAGGTGGGCAGGGGCCAGCCC

CTGGGCGTGGGCATCAGCGGCCACCCCCTGCTGAACAAGCTGGACGAC

ACCGAGAACAGCAACAAGTACGTGGGCAACAGCGGCACCGACAACAGG

GAGTGCATCAGCATGGACTACAAGCAGACCCAGCTGTGCCTGATCGGC

TGCAGGCCCCCATCGGCGAGCACTGGGGCAAGGGCACCCCCTGCAAC

GCCAACCAGGTGAAGGCCGGCGAGTGCCCCCCCCTGGAGCTGCTGAAC

ACCGTGCTGCAGGACGGCGACATGGTGGACACCGGCTTCGGCGCCATG

GACTTCACCACCCTGCAGGCCAACAAGAGCGACGTGCCCCTGGACATC

TGCAGCAGCATCTGCAAGTACCCCGACTACCTGAAGATGGTGAGCGAG

CCCTACGGCGACATGCTGTTCTTCTACCTGAGGAGGGAGCAGATGTTC

GTGAGGCACCTGTTCAACAGGGCCGGCACCGTGGGCGAGACCGTGCCC

GCCGACCTGTACATCAAGGGCACCACCGGCACCCTGCCCAGCACCAGC

TACTTCCCCACCCCCAGCGGCAGCATGGTGACCAGCGACGCCCAGATC

TTCAACAAGCCCTACTGGCTGCAGAGGGCCCAGGGCCACAACAACGGC

ATCTGCTGGAGCAACCAGCTGTTCGTGACCGTGGTGGACACCACCAGG

AGCACCAACATGAGCGTGTGCGCAGCGCCGTGAGCAGCAGCGACAGCACC

TACAAGAACGACAACTTCAAGGAGTACCTGAGGCACGGCGAGGAGTAC

GACCTGCAGTTCATCTTCCAGCTGTGCAAGATCACCCTGACCGCCGAC

GTGATGACCTACATCCACAGCATGAACCCCAGCATCCTGGAGGACTGG

AACTTCGGCCTGACCCCCCCCCCAGCGGCACCCTGGAGGACACCTAC

AGGTACGTGACCAGCCAGGCCGTGACCTGCCAGAAGCCCAGCGCCCCC

AAGCCCAAGGACGACCCCCTGAAGAACTACACCTTCTGGGAGGTGGAC

CTGAAGGAGAAGTTCAGCGCCGACCTGGACCAGTTCCCCCTGGGCAGG

AAGTTCCTGCTGCAGGCCGGCCTGAAGGCCAGGCCCAACTTCAGGCTG

GGCAAGAGGGCCGCCCCCGCCAGCACCAGCAAGAAGAGCAGCACCAAG

AGGAGGAAGGTGAAGAGCTGA

Sequence 15 (SEQ ID NO: 15):
ATGAGCCTGTGGAGGCCCAGCGAGGCCACCGTGTACCTGCCCCCCGTG

CCCGTGAGCAAGGTGGTGAGCACCGACGAGTACGTGACCAGGACCAAC

ATCTACTACCACGCCGGCAGCGCCAGGCTGCTGACCGTGGGCCACCCC

TACTACAGCATCCCCAAGAGCGACAACCCCAAGAAGATCGTGGTGCCC

AAGGTGAGCGGCCTGCAGTACAGGGTGTTCAGGGTGAGGCTGCCCGAC

CCCAACAAGTTCGGCTTCCCCGACACCAGCTTCTACAACCCCGAGACC

CAGAGGCTGGTGTGGGCCTGCGTGGGCCTGGAGGTGGGCAGGGGCCAG

CCCCTGGGCGTGGGCATCAGCGGCCACCCCCTGCTGAACAAGTTCGAC

GACACCGAGAACAGCAACAGGTACGCCGGCGGCCCCGGCACCGACAAC

AGGGAGTGCATCAGCATGGACTACAAGCAGACCCAGCTGTGCCTGCTG

GGCTGCAAGCCCCCCATCGGCGAGCACTGGGGCAAGGGCAGCCCCTGC

AGCAACAACGCCATCACCCCCGGCGACTGCCCCCCCCTGGAGCTGAAG

AACAGCGTGATCCAGGACGGCGACATGGTGGACACCGGCTTCGGCGCC

ATGGACTTCACCGCCCTGCAGGACACCAAGAGCAACGTGCCCCTGGAC

ATCTGCAACAGCATCTGCAAGTACCCCGACTACCTGAAGATGGTGGCC

GAGCCCTACGCGACACCCTGTTCTTCTACCTGAGGAGGGAGCAGATG

TTCGTGAGGCACTTCTTCAACAGGAGCGGCACCGTGGGCGAGAGCGTG

CCCACCGACCTGTACATCAAGGGCAGCGGCAGCACCGCCACCCTGGCC

AACAGCACCTACTTCCCCACCCCCAGCGGCAGCATGGTGACCAGCGAC

GCCCAGATCTTCAACAAGCCCTACTGGATGCAGAGGGCCCAGGGCCAC

AACAACGGCATCTGCTGGGGCAACCAGCTGTTCGTGACCGTGGTGGAC

ACCACCAGGAGCACCAACATGAGCGTGTGCGCCGCCATCGCCAACAGC

GACACCACCTTCAAGAGCAGCAACTTCAAGGAGTACCTGAGGCACGGC

GAGGAGTTCGACCTGCAGTTCATCTTCCAGCTGTGCAAGATCACCCTG

AGCGCCGACATCATGACCTACATCCACAGCATGAACCCCGCCATCCTG

GAGGACTGGAACTTCGGCCTGACCACCCCCCCCAGCGGCAGCCTGGAG

GACACCTACAGGTTCGTGACCAGCCAGGCCATCACCTGCCAGAAGACC

GCCCCCCAGAAGCCCAAGGAGGACCCCTTCAAGGACTACGTGTTCTGG

GAGGTGAACCTGAAGGAGAAGTTCAGCGCCGACCTGGACCAGTTCCCC

CTGCTGCAGGAAGTTCCTGCTGCAGGCCGGCTACAGGGCCAGGCCCAA

GTTCAAGGCCGGCAAGAGGAGCGCCCCCAGCGCCAGCACCACCACCCC

CGCCAAGAGGAAGAAGACCAAGAAGTAA

Sequence 16 (SEQ ID NO: 16):
ATGCTTCCTAGTGAGGCCACTGTCTACTTGCCTCCTGTCCCAGTATCT

AAGGTTGTAAGCACGGATGAATATGTTGCACGCACAAACATATATTAT

CATGCAGGAACAAGCAGGCTGCTGGCCGTGGGCCACCCCTACTACGCC

ATCAAGAAGCAGGACAGCAACAAGATCGCCGTGCCCAAGGTGAGCGGC

CTGCAGTACAGGGTGTTCAGGATACATTTACCTGACCCCAATAAGTTT

GGTTTTCCTGACACCTCATTTTATAATCCAGATACACAGCGGCTGGTT

TGGGCCTGTGTAGGTGTTGAGGTAGGTCGTGGTCAGCCATTAGGTGTG

-continued
```
GGCATTAGTGGCCATCCTTTATTAAATAAATTGGATGACACAGAAAAT
GCTAGTGCTTATGCAGCAAATGCAGGTGTGGATAATAGAGAATGTATA
TCTATGGATTACAAACAAACACAATTGTGTTTAATTGGTTGCAAACCA
CCTATAGGGGAACACTGGGGCAAAGGATCCCCATGTACCAATGTTGCA
GTAAATCCAGGTGATTGTCCACCATTAGAGTTAATAAACACAGTTATT
CAGGATGGTGATATGGTTGATACTGGCTTTGGTGCTATGGACTTTACT
ACATTACAGGCTAACAAAGTGAAGTTCCACTGGATATTTGTACATCT
ATTTGCAAATATCCAGATTATATTAAAATGGTGTCAGAACCATACGGC
GACAGCTTATTTTTTATCTACGAAGGGAACAAATGTTTGTTAGACAT
TTATTTAATAGGGCTGGTGCTGTTGGTGATAATGTACCAGACGATTTA
TACATTAAAGGCTCTGGGTCTACTGCAAATTTAGCCAGTTCAAATTAT
TTTCCTACACCTAGTGGTTCTATGGTTACCTCTGATGCCCAAATATTC
AATAAACCTTACTGGTTACAACGAGCACAGGGCCACAATAATGGCATT
TGTTGGGGTAACCAACTATTTGTTACTGTTGTTGATACTACACGCAGT
ACAAATATGTCATTATGTGCTGCCATATCTACTTCAGAAACTACATAT
AAAAATACTAACTTTAAGGAGTACCTACGACATGGGAGGAATATGAT
TTACAGTTTATTTTTCAACTGTGCAAAATAACCTTAACTGCAGACATT
ATGACATACATACATTCTATGAATTCCACTATTTTGGAGGACTGGAAT
TTTGGTCTACAACCTCCCCCAGGAGGCACACTAGAAGATACTTATAGG
TTTGTAACATCCCAGGCAATTGCTTGTCAAAAACATACACCTCCAGCA
CCTAAAGAAGATCCCCTTAAAAAATACACTTTTTGGGAAGTAAATTTA
AAGGAAAAGTTTTCTGCAGACCTAGATCAGTTTCCTTTAGGACGCAAA
TTTTTACTACAAGCAGGATTGGAGGCCAAACCAAAATTTACATTAGGA
AAACGAAAGCTACACCCACCACCTCATCTACCTCTACAACTGCTAAA
CGCAAAAAACGTAAGCTGTAA
```

Sequence 17 (SEQ ID NO: 17):
```
ATGCTTCCTAGTGAGGCCACTGTCTACTTGCCTCCTGTCCCAGTATCT
AAGGTTGTAAGCACGGATGAATATGTTGCACGCACAAACATATATTAT
CATGCAGGAACATCCAGACTACTTGCAGTTGGACATCCCTATTTTCCT
ATTAAAAAACCTAACAATAACAAAATATTAGTTCCTAAAGTATCAGGA
TTACAATACAGGGTATTTAGAATACATTTACCTGACCCCAATAAGTTT
GGTTTTCCTGACACCTCATTTTATAATCCAGATACACAGCGGCTGGTT
TGGGCCTGTGTAGGCGTGGAGGTGGGCAGCTGGCCAGCCCCTGGGCGT
GGGCATCAGCGGCCACCCCCTGCTGAACAAGCTGGACGACACCGAGAA
CAGCAACAAGTACGTGGGCAACAGCGGCACCGACAACAGGGAGTGCAT
CAGCATGGACTACAAGCAGACCCAGCTGTGCCTGATCGGCTGCAAACC
ACCTATAGGGGAACACTGGGGCAAAGGATCCCCATGTACCAATGTTGC
AGTAAATCCAGGTGATTGTCCACCATTAGAGTTAATAAACACAGTTAT
TCAGGATGGTGATATGGTTGATACTGGCTTTGGTGCTATGGACTTTAC
TACATTACAGGCTAACAAAGTGAAGTTCCACTGGATATTTGTACATC
TATTTGCAAATATCCAGATTATATTAAAATGGTGTCAGAACCATACGG
```

-continued
```
CGACAGCTTATTTTTTATCTACGAAGGGAACAAATGTTTGTTAGACA
TTTATTTAATAGGGCTGGTGCTGTTGGTGATAATGTACCAGACGATTT
ATACATTAAAGGCTCTGGGTCTACTGCAAATTTAGCCAGTTCAAATTA
TTTTCCTACACCTAGTGGTTCTATGGTTACCTCTGATGCCCAAATATT
CAATAAACCTTACTGGTTACAACGAGCACAGGGCCACAATAATGGCAT
TTGTTGGGGTAACCAACTATTTGTTACTGTTGTTGATACTACACGCAG
TACAAATATGTCATTATGTGCTGCCATATCTACTTCAGAAACTACATA
TAAAAATACTAACTTTAAGGAGTACCTACGACATGGGAGGAATATGA
TTTACAGTTTATTTTTCAACTGTGCAAAATAACCTTAACTGCAGACAT
TATGACATACATACATTCTATGAATTCCACTATTTTGGAGGACTGGAA
TTTTGGTCTACAACCTCCCCCAGGAGGCACACTAGAAGATACTTATAG
GTTTGTAACATCCCAGGCAATTGCTTGTCAAAAACATACACCTCCAGC
ACCTAAAGAAGATCCCCTTAAAAAATACACTTTTTGGGAAGTAAATTT
AAAGGAAAAGTTTTCTGCAGACCTAGATCAGTTTCCTTTAGGACGCAA
ATTTTTACTACAAGCAGGATTGGAGGCCAAACCAAAATTTACATTAGG
AAAACGAAAGCTACACCCACCACCTCATCTACCTCTACAACTGrCTA
AACGCAAAAAACGTAAGCTGTAA
```

Sequence 18 (SEQ ID NO: 18):
```
ATGCTTCCTAGTGAGGCCACTGTCTACTTGCCTCCTGTCCCAGTATCT
AAGGTTGTAAGCACGGATGAATATGTTGCACGCACAAACATATATTAT
CATGCAGGAACATCCAGACTACTTGCAGTTGGACATCCCTATTTTCCT
ATTAAAAAACCTAACAATAACAAAATATTAGTTCCTAAAGTATCAGGA
TTACAATACAGGGTATTTAGAATACATTTACCTGACCCCAATAAGTTT
CGGTTTTCCTGACACCTCATTTTATAATCCAGATACACAGCGGTGGTT
TGGGCCTGTGTAGGTGTTGAGGTAGGTCGTGGTCAGCCATTAGGTGTG
GGCATTAGTGGCCATCCTTTATTAAATAAATTGGATGACACAGAAAAT
GCTAGTGCTTATGCAGCAAATGCAGGTGTGGATAATAGAGAATGTATA
TCTATGGATTACAAACAAACACAATTGTGTTTAATTGGTTGCAAACCA
CCTATAGGGGAACACTGGGGCAAAGGACCCCATGTAACGCTAATCAA
GTAAAGGCAGGTGAGTGTCCACCATTAGAGTTAATAAACACAGTTATT
CAGGATGGTGATATGGTTGATACTGGCTTTGGTGCTATGGACTTTACT
ACATTACAGGCTAACAAAGTGAAGTTCCACTGGATATTTGTACATCT
ATTTGCAAATATCCAGATTATATTAAAATGGTGTCAGAACCATACGGC
GACAGCTTATTTTTTATCTACGAAGGGAACAAATGTTTGTTAGACAT
TTATTTAATAGGGCTGGTGCTGTTGGTGATAATGTACCAGACGATTTA
TACATTAAAGGCTCTGGGTCTACTGCAAATTTAGCCAGTTCAAATTAT
TTTCCTACACCTAGTGGTTCTATGGTTACCTCTGATGCCCAAATATTC
AATAAACCTTACTGGTTACAACGAGCACAGGGCCACAATAATGGCATT
TGTTGGGGTAACCAACTATTTGTTACTGTTGTTGATACTACACGCAGT
ACAAATATGTCATTATGTGCTGCCATATCTACTTCAGAAACTACATAT
AAAAATACTAACTTTAAGGAGTACCTACGACATGGGAGGAATATGAT
```

TTACAGTTTATTTTTCAACTGTGCAAAATAACCTTAACTGCAGACATT

ATGACATACATACATTCTATGAATTCCACTATTTTGGAGGACTGGAAT

TTTGGTCTACAACCTCCCCCAGGAGGCACACTAGAAGATACTTATAGG

TTTGTAACATCCCAGGCAATTGCTTGTCAAAAACATACACCTCCAGCA

CCTAAAGAAGATCCCCTTAAAAAATACACTTTTTGGGAAGTAAATTTA

AAGGAAAAGTTTTCTGCAGACCTAGATCAGTTTCCTTTAGGACGCAAA

TTTTTACTACAAGCAGGATTGGAGGCCAAACCAAAATTTACATTAGGA

AAACGAAAAGCTACACCCACCACCTCATCTACCTCTACAACTGCTAAA

CGCAAAAAACGTAAGCTGTAA

Sequence 19 (SEQ ID NO: 19):
ATGCTTCCTAGTGAGGCCACTGTCTACTTGCCTCCTGTCCCAGTATCT

AAGGTTGTAAGCACGGATGAATATGTTGCACGCACAAACATATATTAT

CATGCAGGAACATCCAGACTACTTGCAGTTGGACATCCCTATTTTCCT

ATTAAAAAACCTAACAATAACAAAATATTAGTTCCTAAAGTATCAGGA

TTACAATACAGGGTATTTAGAATACATTTACCTGACCCCAATAAGTTT

GGTTTTCCTGACACCTCATTTTATAATCCAGATACACAGCGGCTGGTT

TGGGCCTGTGTAGGTGTTGAGGTAGGTCGTGGTCAGCCATTAGGTGTG

GGCATTAGTGGCCATCCTTTATTAAATAAATTGGATGACACAGAAAAT

GCTAGTGCTTATGCAGCAAATGCAGGTGTGGATAATAGAGAATGTATA

TCTATGGATTACAAACAAACACAATTGTGTTTAATTGGTTGCAAACCA

CCTATAGGGGAACACTGGGGCAAAGGATCCCCATGTACCAATGTTGCA

GTAAATCCAGGTGATTGTCCACCATTAGAGTTAATAAACACAGTTATT

CAGGATGGTGATATGGTTGATACTGGCTTTGGTGCTATGGACTTTACT

ACATTACAGGCTAACAAAAGTGAAGTTCCACTGGATATTGTACATCT

ATTTGCAAATATCCAGATTATATTAAAATGGTGTCAGAACCATATGGC

GACAGCTTATTCTTCTACCTGAGGAGGGAGCAGATGTTCGTGAGGCAC

CTGTTCAACAGGGCCGGCACCGTGGGCGAGACCGTGCCCGCCGACCTG

TACATCAAGGGCACCACCGGCACCCTGCCCAGCACCAGCTACTTCCCC

ACCCCCAGCGGCAGCATGGTGACCAGCGACGCCCAGATCTTCAACAAG

CCCTACTGGCTGCAGAGGGCCCAGGGCCACAACAACGGCATCTGCTGG

AGTAACCAACTATTTGTTACTGTTGTTGATACTACACGCAGTACAAAT

ATGTCATTATGTGCTGCCATATCTACTTCAGAAACTACATATAAAAAT

ACTAACTTTAAGGAGTACCTACGACATGGGGAGGAATATGATTTACAG

TTTATTTTTCAACTGTGCAAAATAACCTTAACTGCAGACATTATGACA

TACATACATTCTATGAATTCCACTATTTTGGAGGACTGGAATTTTGGT

CTACAACCTCCCCCAGGAGGCACACTAGAAGATACTTATAGGTTTGTA

ACATCCCAGGCAATTGCTTGTCAAAAACATACACCTCCAGCACCTAAA

CGAAGATCCCCTTAAAAAATACACTTTTTGGGAAGTAAATTTAAAGGA

CCAAAGTTTTCTGCAGACTAGATCAGTTTCCTTTAGGACGCAAATTTT

TACTACAAGCAGGATTGGAGGCCAAAAAAATTTACATTAGGAAAACGA

AAAGCTACACCCACCACCTCATCTACCTCTACAACTGCTAAACGCAAA

AAACGTAAGCTGTAA

Sequence 20 (SEQ ID NO: 20):
ATGCTTCCTAGTGAGGCCACTGTCTACTTGCCTCCTGTCCCAGTATCT

AAGGTTGTAAGCACGGATGAATATGTTGCACGCACAAACATATATTAT

CATGCAGGAACATCCAGACTACTTGCAGTTGGACATCCCTATTTTCCT

ATTAAAAAACCTAACAATAACAAAATATTAGTTCCTAAAGTATCAGGA

TTACAATACAGGGTATTTAGAATACATTTACCTGACCCCAATAAGTTT

GGTTTTCCTGACACCTCATTTTATAATCCAGATACACAGCGGCTGGTT

TGGGCCTGTGTAGGTGTTGAGGTAGGTCGTGGTCAGCCATTAGGTGTG

GGCATTAGTGGCCATCCTTTATTAAATAAATTGGATGACACAGAAAAT

GCTAGTGCTTATGCAGCAAATGCAGGTGTGGATAATAGAGAATGTATA

TCTATGGATTACAAACAAACACAATTGTGTTTAATTGGTTGCAAACCA

CCTATAGGGGAACACTGGGGCAAAGGATCCCCATGTACCAATGTTGCA

GTAAATCCAGGTGATTGTCCACCATTAGAGTTAATAAACACAGTTATT

CAGGATGGTGATATGGTTGATACTGGCTTTGGTGCTATGGACTTTACT

ACATTACAGGCTAACAAAAGTGAAGTTCCACTGGATATTGTACATCT

ATTTGCAAATATCCAGATTATATTAAAATGGTGTCAGAACCATACGGC

GACAGCTTATTTTTTTATCTACGAAGGGAACAAATGTTTGTTAGACAT

TTATTTAATAGGGCTGGTGCTGTTGGTGATAATGTACCAGACGATTTA

TACATTAAAGGCTCTGGGTCTACTGCAAATTTAGCCAGTTCAAATTAT

TTTCCTACACCTAGTGGTTCTATGGTTACCTCTGATGCCCAAATATTC

AATAAACCTTACTGGTTACAACGAGCACAGGGCCACAATAATGGCATT

TGTTGGAGCAACCAACTATTTGTTACTGTTGTTGATACTACACGCAGT

ACAAATATGTCATTATGTGCTGCCGTATCTAGTTCAGACAGTACATAT

AAAAATGATAACTTTAAGGAGTACCTACGACATGGGGAGGAATATGAT

TTACAGTTTATTTTTCAACTGTGCAAAATAACCTTAACTGCAGACATT

ATGACATACATACATTCTATGAATTCCACTATTTTGGAGGACTGGAAT

TTTGGTCTACAACCTCCCCCAGGAGGCACACTAGAAGATACTTATAGG

TTTGTAACATCCCAGGCAATTGCTTGTCAAAAACATACACCTCCAGCA

CCTAAAGAAGATCCCCTTAAAAAATACACTTTTTGGGAAGTAAATTTA

AAGGAAAAGTTTTCTGCAGACCTAGATCAGTTTCCTTTAGGACGCAAA

TTTTTACTACAAGCAGGATTGGAGGCCAAACCAAAATTTACATTAGGA

AAACGAAAAGCTACACCCACCACCTCATCTACCTCTACAACTGCTAAA

CGCAAAAAACGTAAGCTGTAA

Sequence 21 (SEQ ID NO: 21):
ATGCTTCCTAGTGAGGCCACTGTCTACTTGCCTCCTGTCCCAGTATCT

AAGGTTGTAAGCACGGATGAATATGTTGCACGCACAAACATATATTAT

CATGCAGGAACATCCAGACTACTTGCAGTGGGCCACCCCTACTACAGC

ATCCCCAAGAGCGACAACCCCAAGAAGATCGTGGTGCCCAAGGTGAGC

GGCCTGCAGTACAGGGTGTTCAGGATACATTTACCTGACCCCAATAAG

-continued
```
TTTGGTTTTCCTGACACCTCATTTTATAATCCAGATACACAGCGGCTG

GTTTGGGCCTGTGTAGGTGTTGAGGTAGGTCGTGGTCAGCCATTAGGT

GTGGGCATTAGTGGCCATCCTTTATTAAATAAATTGGATGACACAGAA

AATGCTAGTGCTTATGCAGCAAATGCAGGTGTGGATAATAGAGAATGT

ATATCTATGGATTACAAACAAACACAATTGTGTTTAATTGGTTGCAAA

CCACCTATAGGGGAACACTGGGGCAAAGGATCCCCATGTACCAATGTT

GCAGTAAATCCAGGTGATTGTCCACCATTAGAGTTAATAAACACAGTT

ATTCAGGATGGTGATATGGTTGATACTGGCTTTGGTGCTATGGACTTT

ACTACATTACAGGCTAACAAAAGTGAAGTTCCACTGGATATTTGTACA

TTCTATTGCAAATATCCAGATTATATTAAATGGTGTCAGAACCATAT

GGCGACAGCTTATTCTTCTACCTGAGGAGGGAGCAGATGTTCGTGAGG

CACCTGTTCAACAGGGCCGGCACCGTGGGCGAGACCGTGCCCGCCGAC

CTGTACATCAAGGGCACCACCGGCACCCTGCCCAGCACCAGCTACTTC

CCCACCCCCAGCGGCAGCATGGTGACCAGCGACGCCCAGATCTTCAAC

AAGCCCTACTGGCTGCAGAGGGCCCAGGGCCACAACAACGGCATCTG

TGGAGTAACCAACTATTTGTTACTGTTGTTGATACTACACGCAGTACA

GAATATGTCATTATGTGCTGCCATATCTACTTCAGAAACTACATATAA

AAATACTAACTTTAAGGATACCTACGACATGGGGAGGAATATGATTTA

CAGTTTATTTTTCAACTGTGCAAAATAACCTTAACTGCAGACATTATG

ACATACATACATTCTATGAATTCCACTATTTTGGAGGACTGGAATTTT

GGTCTACAACCTCCCCCAGGAGGCACACTAGAAGATACTTATAGGTTT

GTAACATCCCAGGCAATTGCTTGTCAAAAACATACACCTCCAGCACCT

AAAGAAGATCCCCTTAAAAAATACACTTTTTGGGAAGTAAATTTAAAG

GAAAAGTTTTCTGCAGACCTAGATCAGTTTCCTTTAGGACGCAAATTT

TTACTACAAGCAGGATTGGAGGCCAAACCAAAATTTACATTAGGAAAA

CGAAAAGCTACACCCACCACCTCATCTACCTCTACAACTGCTAAACGC

AAAAAACGTAAGCTGTAA

Sequence 22 (SEQ ID NO: 22):
ATGCTTCCTAGTGAGGCCACTGTCTACTTGCCTCCTGTCCCAGTATCT

AAGGTTGTAAGCACGGATGAATATGTTGCACGCACAAACATATATTAT

CATGCAGGAACATCCAGACTACTTGCAGTTGGACATCCCTATTTTCCT

ATTAAAAAACCTAACAATAACAAAATATTAGTTCCTAAAGTATCAGGA

TTACAATACAGGGTATTTAGAATACATTTACCTGACCCCAATAAGTTT

GGTTTTCCTGACACCTCATTTTATAATCCAGATACACAGCGGCTGGTT

TGGGCCTGTGTAGGTGTTGAGGTGGGCAGGGGCCAGCCCCTGGGCGTG

GGCATCAGCGGCCACCCCCTGCTGAACAAGTTCGACGACACCGAGAAC

AAGCAACAGGTACGCCGGCGGCCCCGGCACCGACAACAGGGAGTGCAT

CAGCATGGACTACAAGCAGCCCAGCTGTGCCTGATTGGTTGCAAACCA

CCTATAGGGGAACACTGGGGCAAAGGATCCCCATGTACCAATGTTGCA

GTAAATCCAGGTGATTGTCCACCATTAGAGTTAATAAACACAGTTATT

CAGGATGGTGATATGGTTGATACTGGCTTTGGTGCTATGGACTTTACT
```

-continued
```
ACATTACAGGCTAACAAAAGTGAAGTTCCACTGGATATTTGTACATCT

ATTTGCAAATATCCAGATTATATTAAATGGTGTCAGAACCATATGGC

GACAGCTTATTCTTCTACCTGAGGAGGGAGCAGATGTTCGTGAGGCAC

CTGTTCAACAGGGCCGGCACCGTGGGCGAGACCGTGCCCGCCGACCTG

TACATCAAGGGCACCACCGGCACCCTGCCCAGCACCAGCTACTTCCCC

ACCCCCAGCGGCAGCATGGTGACCAGCGACGCCCAGATCTTCAACAAG

CCCTACTGGCTGCAGAGGGCCCAGGGCCACAACAACGGCATCTGCTGG

AGTAACCAACTATTTGTTACTGTTGTTGATACTACACGCAGTACAAAT

ATGTCATTATGTGCTGCCATATCTACTTCAGAAACTACATATAAAAAT

ACTAACTTTAAGGAGTACCTACGACATGGGGAGGAATATGATTTACAG

TTTATTTTTCAACTGTGCAAAATAACCTTAACTGCAGACATTATGACA

TACATACATTCTATGAATTCCACTATTTTGGAGGACTGGAATTTTGGT

CTACAACCTCCCCCAGGAGGCACACTAGAAGATACTTATAGGTTTGTA

AACATCCCAGGCAATTGCTTGTCAAAAACATACACCTCCAGCACCTAA

AGAAGATCCCCTTAAAAAATACACTTTTTGGGAAGTAAATTTAAAGGA

AAAGTTTTCTGCAGCCTAGATCAGTTTCCTTTAGGACGCAAATTTTTA

CTACAAGCAGGATTGGAGGCCAAACCAAAATTTACATTAGGAAAACGA

AAAGCTACACCCACCACCTCATCTACCTCTACAACTGCTAAACGCAAA

AAACGTAAGCTGTAA

Sequence 23 (SEQ ID NO: 23):
ATGCTTCCTAGTGAGGCCACTGTCTACTTGCCTCCTGTCCCAGTATCT

AAGGTTGTAAGCACGGATGAATATGTTGCACGCACAAACATATATTAT

CATGCAGGAACATCCAGACTACTTGCAGTTGGACATCCCTATTTTCCT

ATTAAAAAACCTAACAATAACAAAATATTAGTTCCTAAAGTATCAGGA

TTACAATACAGGGTATTTAGAATACATTTACCTGACCCCAATAAGTTT

GGTTTTCCTGACACCTCATTTTATAATCCAGATACACAGCGGCTGGTT

TGGGCCTGTGTAGGTGTTGAGGTAGGTCGTGGTCAGCCATTAGGTGTG

GGCATTAGTGGCCATCCTTTATTAAATAAATTGGATGACACAGAAAAT

GCTAGTGCTTATGCAGCAAATGCAGGTGTGGATAATAGAGAATGTATA

GTCTATGGATTACAAACAAACACAATTGTGTTTAATTGGCTGCAAGCC

CCCCATCGGCGAGCACTGGGGCAAGGGCACCCCTGCAGCAACAACGCC

ACATCACCCCCGGCGACTGCCCCCCCCTGGAGCTGATAAACACAGTTA

TTCAGGATGGTGATATGGTTGATACTGGCTTTGGTGCTATGGACTTTT

ACATTACAGGCTAACAAAAGTGAAGTTCCACTGGATATTTGTACATCT

ATTTGCAAATATCCAGATTATATTAAATGGTGTCAGAACCATATGGC

GACAGCTTATTCTTCTACCTGAGGAGGGAGCAGATGTTCGTGAGGCAC

CTGTTCAACAGGGCCGGCACCGTGGGCGAGACCGTGCCCGCCGACCTG

TACATCAAGGGCACCACCGGCACCCTGCCCAGCACCAGCTACTTCCCC

ACCCCCAGCGGCAGCATGGTGACCAGCGACGCCCAGATCTTCAACAAG

CCCTACTGGCTGCAGAGGGCCCAGGGCCACAACAACGGCATCTGCTGG

AGTAACCAACTATTTGTTACTGTTGTTGATACTACACGCAGTACAAAT
```

```
ATGTCATTATGTGCTGCCATATCTACTTCAGAAACTACATATAAAAT

CACTAACTTTAAGGAGTACCTACGACATGGGGAGGAATATGATTTACA

GTTTATTTTTCAACTGTGCAAAATAACTTAACTGCAGACATTATGACA

TACATACATTCTATGAATTCCACTATTTTGGAGGACTGGAATTTTGGT

ACTACAACCTCCCCCAGGAGGCACACTAGAAGATACTTATAGGTTTGT

AACATCCCAGGCAATTGCTTGTCAAAAACATACACCTCCAGCACCTAA

AGAAGTCCCCTTAAAAAATACACTTTTTGGGAAGTAAATTTAAAGGAA

AAGTTTTCTGCAGACCTAGATCAGTTTCCTTTAGGACGCAAATTTTTA

CTACAAGCAGGATTGGAGGCCAAACCAAAATTTACATTAGGAAAACGA

AAAGCTACACCCACCACCTCATCTACCTCTACAACTGCTAAACGCAAA

AAACGTAAGCTGTAA

Sequence 24 (SEQ ID NO: 24):
ATGCTTCCTAGTGAGGCCACTGTCTACTTGCCTCCTGTCCCAGTATCT

AAGGTTGTAAGCACGGATGAATATGTTGCACGCACAAACATATATTAT

CATGCAGGAACATCCAGACTACTTGCAGTTGGACATCCCTATTTTCCT

ATTAAAAAACCTAACAATAACAAAATATTAGTTCCTAAAGTATCAGGA

TTACAATACAGGGTATTTAGAATACATTTACCTGACCCCAATAAGTTT

GGTTTTCCTGACACCTCATTTTATAATCCAGATACACAGCGGCTGGTT

TGGGCCTGTGTAGGTGTTGAGGTAGGTCGTGGTCAGCCATTAGGTGTG

GGCATTAGTGGCCATCCTTTATTAAATAAATTGGATGACACAGAAAT

GCTAGTGCTTATGCAGCAAATGCAGGTGTGGATAATAGAGAATGTATA

TCTATGGATTACAAACAAACACAATTGTGTTTAATTGGTTGCAAACCA

CCTATAGGGGAACACTGGGGCAAAGGATCCCCATGTACCAATGTTGCA

GTAAATCCAGGTGATTGTCCACCATTAGAGTTAATAAACACAGTTATT

CAGGATGGTGATATGGTTGATACTGGCTTTGGTGCTATGGACTTTACT

ACATTACAGGCTAACAAAAGTGAAGTTCCACTGGATATTTGTACATCT

ATTTGCAAATATCCAGATTATATTAAAATGGTGTCAGAACCATATGGC

GACAGCTTATTCTTCTACCTGAGGAGGGAGCAGATGTTCGTGAGGCAC

CTGTTCAACAGGGCCGGCACCGTGGGCGAGACCGTGCCCGCCGACCTG

TACATCAAGGGCACCACCGGCACCCTGCCCAGCACCAGCTACTTCCCC

ACCCCCAGCGGCAGCATGGTGACCAGCGACGCCCAGATCTTCAACAAG

CCCTACTGGCTGCAGAGGGCCCAGGGCCACAACAACGGCATCTGCTGG

AGTAACCAACTATTTGTTACTGTTGTTGATACTACACGCAGTACAAAT

ATGTCATTATGCGCCGCCATCGCCAACAGCGACACCACCTTCAAGAGC

AGCAACTTCAAGGAGTACCTGAGGCACGGCGAGGAGTATGATTTACAG

TTTATTTTTCAACTGTGCAAAATAACCTTAACTGCAGACATTATGACA

TACATACATTCTATGAATTCCACTATTTTGGAGGACTGGAATTTTGGT

CTACAACCTCCCCCAGGAGGCACACTAGAAGATACTTATAGGTTTGTA

ACATCCCAGGCAATTGCTTGTCAAAAACATACACCTCCAGCACCTAAA

GAAGATCCCCTTAAAAAATACACTTTTTGGGAAGTAAATTTAAAGGAA

AAGTTTTCTGCAGACCTAGATCAGTTTCCTTTAGGACGCAAATTTTTA

CTACAAGCAGGATTGGAGGCCAAACCAAAATTTACATTAGGAAAACGA

AAAGCTACACCCACCACCTCATCTACCTCTACAACTGCTAAACGCAAA

AAACGTAAGCTGTAA

Sequence 25 (SEQ ID NO: 25):
TVGETVPADLYIKGTTGTLPSTS

Sequence 26 (SEQ ID NO: 26):
YSIPKSDNPKKIV

Sequence 27 (SEQ ID NO: 27):
FDDTENSNRYAGGPGT

Sequence 28 (SEQ ID NO: 28):
SNNAIT
```

Specific Models for Carrying Out the Invention

The invention is described with reference to the following examples which are intended to illustrate, but not limit the invention.

Unless otherwise specified, the molecular biology experimental methods and immunoassays used in the present invention were carried out substantially by referring to the procedures of J. Sambrook et al., Molecular Cloning: A Laboratory Manual, 2nd Edition, Cold Spring Harbor Laboratory Press, 1989, and F. M. Ausubel et al., Short Protocols in Molecular Biology, 3rd Edition, John Wiley & Sons, Inc., 1995; restriction endonucleases were used under the conditions recommended by the manufacturers. It will be understood by those skilled in the art that the present invention is described by way of examples, and the examples are not intended to limit the scope of the invention.

Example 1. Expression and Purification of Mutated HPV16 L1 Protein

Construction of Expression Vector

An expression vector encoding the mutated HPV16 L1 protein containing Segment 3 or Segment 5 derived from HPV35 L1 protein was constructed by PCR for multi-site mutagenesis, in which the initial template used was pTO-T7-HPV16L1N30C plasmid (which encoded the HPV16 L1 protein with a N-terminal truncation of 30 amino acids (this protein was named as HPV16N30); abbreviated as 16L1N30 in Table 2). The templates and primers used for each PCR reaction were shown in Table 2, and the amplification conditions of the PCR reaction were set as: denaturating at 94° C. for 10 minutes; 25 cycles of (denaturating at 94° C. for 50 seconds, annealing at a specified temperature for a certain time, extending at 72° C. for 7 minutes and 30 seconds); finally extending at 72° C. for 7 minutes. The sequences of the used PCR primers were listed in Table 3.

2 μL of restriction endonuclease DpnI was added to the amplification product (50 μL), and incubated at 37° C. for 60 minutes. 10 μL of the enzyme-digested product was used for transformation of 40 μL of competent E. coli ER2566 (purchased from New England Biolabs) prepared by the calcium chloride method. The transformed E. coli was spread onto a solid LB medium (LB medium components: 10 g/L peptone, 5 g/L yeast powder, 10 g/L sodium chloride, the same hereinafter) containing kanamycin (final concentration: 25 mg/mL, the same hereinafter), and was subjected to static culture at 37° C. for 10-12 hours until single colonies were observed clearly. Single colonies were picked and inoculated into a test tube containing 4 mL of liquid LB medium (containing kanamycin), and cultured with shaking at 220 rpm for 10 hours at 37° C. Subsequently, 1 mL of the bacterial solution was taken and stored at −70° C. Plasmid was extracted from the *E. coli*, and the nucleotide sequences of the target fragments inserted into the plasmid were sequenced using T7 primer. The sequencing results showed that the nucleotide sequences of the target fragments inserted in each of the constructed plasmids (expression vectors) were SEQ ID NOs: 18 and 20, respectively, and the amino acid sequences encoded thereby were SEQ ID NOs: 6 and 8 (the corresponding proteins were named as H16N30-35T3 and H16N30-35T5, respectively).

The mutated protein H16N30-35T3 differed from HPV16N30 in that the amino acid residues at positions 199-210 of the wild-type HPV16 L1 protein were replaced with the amino acid residues at positions 173-184 of the wild-type HPV35 L1 protein. The mutated protein H16N30-35T5 differed from HPV16N30 in that the amino acid residues at positions 374-384 of the wild-type HPV16 L1 protein were replaced with the amino acid residues at positions 346-356 of the wild-type HPV35 L1 protein.

An expression vector of the mutated HPV16 L1 protein containing Segment 1, Segment 2 or Segment 4 derived from HPV35 L1 protein was constructed by using Gibson assembly (Gibson D G, Young L, Chuang R Y, Venter J C, Hutchison C A, Smith H O. Enzymatic assembly of DNA molecules up to several hundred kilobases. Nat Methods. 2009; 6:343-5. doi: 10.1038/nmeth. 1318). Briefly, a short fragment containing a mutation and a long fragment containing no mutation were first obtained by PCR reaction, and then the two fragments were ligated into a loop using a Gibson assembly system. The initial template used was pTO-T7-HPV16L1N30C plasmid and pTO-T7-HPV35L1 plasmid (which encoded HPV35 L1 protein; abbreviated as 35L1 in Table 2). The templates and primers used for the respective PCR reactions were shown in Table 2, and the amplification conditions for the PCR reaction for amplifying the short fragment were set as: denaturating at 94° C. for 10 minutes; 25 cycles of (denaturating at 94° C. for 50 seconds, annealing at a specified temperature for a certain time, extending at 72° C. for 1 minute); finally extending at 72° C. for 10 minutes. The amplification conditions for the PCR reaction for amplifying the long fragment were set as: denaturating at 94° C. for 10 minutes; 25 cycles of (denaturating at 94° C. for 50 seconds, annealing at a specified temperature for a certain time, extending at 72° C. for 7 minutes and 30 seconds); finally extending at 72° C. for 10 minutes. The sequences of the PCR primers used were listed in Table 3. The amplified product was subjected to electrophoresis, and then the target fragments were recovered using a DNA recovery kit and their concentrations were determined. The amplified short and long fragments were mixed at a molar ratio of 2:1 (total volume of 3 µL), followed by the addition of 3 µL of 2× Gibson Assembly premixes (2× Gibson Assembly Master Mix, purchased from NEB, containing T5 exonuclease, Phusion DNA polymerase, Taq DNA ligase), and reacted at 50° C. for 1 hour.

40 µL of competent *E. coli* ER2566 (purchased from New England Biolabs) prepared by the calcium chloride method was transformed with the assembled product (6 µL). The transformed *E. coli* was spread on a solid LB medium containing kanamycin and were subjected to static culture at 37° C. for 10-12 hours until the single colonies were observed clearly. Single colonies were picked and inoculated into a test tube containing 4 mL of a liquid LB medium (containing kanamycin), and cultured with shaking at 220 rpm for 10 hours at 37° C. Subsequently, 1 mL of the bacterial solution was taken and stored at −70° C. The plasmid was extracted from *E. coli*, and the nucleotide sequences of the target fragments inserted into the plasmid were sequenced using T7 primer. The sequencing results showed that the nucleotide sequences of the target fragments inserted in each of the constructed plasmids (expression vectors) were SEQ ID NOs: 16, 17, and 19, respectively, and the amino acid sequences encoded thereby were SEQ ID NOs: 4, 5, and 7 (the corresponding proteins were named as H16N30-35T1, H16N30-35T2 and H16N30-35T4, respectively).

The mutated protein H16N30-35T1 differed from HPV in that the amino acid residues at positions 76-87 of the wild-type HPV16 L1 protein were replaced with the amino acid residues at positions 50-61 of the wild-type HPV35 L1 protein. The mutated protein H16N30-35T2 differed from HPV16N30 in that the amino acid residues at positions 158-167 of the wild-type HPV16 L1 protein were replaced with the amino acid residues at positions 132-141 of the wild-type HPV35 L1 protein. The mutated protein H16N30-35T4 differed from HPV16N30 in that the amino acid residues at positions 292-316 of the wild-type HPV16 L1 protein were replaced with the amino acid residues at positions 266-288 of the wild-type HPV35 L1 protein.

An expression vector encoding the mutated HPV16 L1 protein with double-substitution which contains a segment derived from HPV35 L1 and a segment derived from HPV31 L1, was constructed by using Gibson assembly. Briefly, a short fragment containing a mutation and a long fragment containing no mutation were firstly obtained by PCR reaction, and then the two fragments were ligated into a loop using a Gibson assembly system. The initial template used included pTO-T7-H16N30-35T4 plasmid (which encoded the mutated protein H16N30-35T4; abbreviated as H16N30-35T4 in Table 2), and p TO-T7-HPV31L1 plasmid (which encoded HPV31 L1 protein; abbreviated as 31L1 in Table 2). The templates and primers used for the respective PCR reactions were shown in Table 2, and the amplification conditions for the PCR reaction for amplifying the short fragment were set as: denaturating at 94° C. for 10 minutes; 25 cycles of (denaturating at 94° C. for 50 seconds, annealing at a specified temperature for a certain time, extending at 72° C. for 1 minute); finally extending at 72° C. for 10 minutes. The amplification conditions for the PCR reaction for amplifying the long fragment were set as: denaturating at 94° C. for 10 minutes; 25 cycles of (denaturating at 94° C. for 50 seconds, annealing at a specified temperature for a certain time, extending at 72° C. for 7 minutes and 30 seconds); finally extending at 72° C. for 10 minutes. The sequences of the PCR primers used are listed in Table 3. The amplified product was subjected to electrophoresis, and then the target fragments were recovered using a DNA recovery kit and its concentration was determined. The amplified short and long fragments were mixed at a molar ratio of 2:1 (total volume of 3 µL), followed by the addition of 3 µL of 2× Gibson Assembly premixes (2× Gibson Assembly Master Mix, purchased from NEB, containing T5 exonuclease, Phusion DNA polymerase, Taq DNA ligase), and reacted at 50° C. for 1 hour.

40 µL of competent *E. coli* ER2566 (purchased from New England Biolabs) prepared by the calcium chloride method was transformed with the assembled product (6 µL). The transformed *E. coli* was spread on a solid LB medium containing kanamycin and subjected to static culture at 37° C. for 10-12 hours until the single colonies were observed clearly. Single colonies were picked and inoculated into a test tube containing 4 mL of a liquid LB medium (containing kanamycin), and cultured with shaking at 220 rpm for 10 hours at 37° C. Subsequently, 1 mL of the bacterial solution was taken and stored at −70° C. The plasmid was extracted from *E. coli*, and the nucleotide sequences of the target fragments inserted into the plasmid was sequenced using T7 primer. The sequencing results showed that the nucleotide sequences of the desired fragments inserted in each of the constructed plasmids (expression vectors) were SEQ ID NOs: 21, 22, 23, and 24, respectively, and the amino acid sequences encoded thereby were SEQ ID NOs: 9, 10, 11, 12 (the corresponding proteins were named as H16N30-35T4-31S1, H16N30-35T4-31S2, H16N30-35T4-31S3, and H16N30-35T4-31S5).

The mutated protein H16N30-35T4-31S1 differed from HPV16N30 in that the amino acid residues at positions 292-316 of the wild-type HPV16 L1 protein were replaced with the amino acid residues at positions 266-288 of the wild-type HPV35 L1 protein, and the amino acid residues at positions 76-87 of the wild-type HPV16 L1 protein were replaced with the amino acid residues at positions 50-62 of the wild-type HPV31 L1 protein. The mutated protein H16N30-35T4-31S2 differed from HPV16N30 in that the amino acid residues at positions 292-316 of the wild-type HPV16 L1 protein were replaced with the amino acid residues at positions 266-288 of the wild-type HPV35 L1 protein, and the amino acid residues at positions 152-167 of the wild-type HPV16 L1 protein were replaced with the amino acid residues at positions 127-142 of the wild-type HPV31 L1 protein. The mutated protein H16N30-35T4-31S3 differed from HPV16N30 in that the amino acid residues at positions 292-316 of the wild-type HPV16 L1 protein were replaced with the amino acid residues at positions 266-288 of the wild-type HPV35 L1 protein, and the amino acid residues at positions 202-207 of the wild-type HPV16 L1 protein were replaced with the amino acid residues at positions 177-182 of the wild type HPV31 L1 protein. The mutated protein H16N30-35T4-31S5 differed from HPV16N30 in that the amino acid residues at positions 292-316 of the wild-type HPV16 L1 protein were replaced with the amino acid residues at positions 266-288 of the wild-type HPV35 L1 protein, and the amino acid residues at positions 375-384 of the wild-type HPV16 L1 protein were replaced with the amino acid residues at positions 350-359 of the wild-type HPV31 L1 protein.

TABLE 2

Templates and primers for PCR reactions used to construct expression vectors

| Template | Upstream primer | Downstream primer | Product |
|---|---|---|---|
| 16L1N30 | G-V-H16N30-35T1-F | G-V-H16N30-35T1-R | H16N30-35T1 long fragment |
| 35L1 | G-H16N30-35T1-F | G-H16N30-35T1-R | H16N30-35T1 short fragment |
| 16L1N30 | G-V-H16N30-35T2-F | G-V-H16N30-35T2-R | H16N30-35T2 long fragment |
| 35L1 | G-H16N30-35T2-F | G-H16N30-35T2-R | H16N30-35T2 short fragment |
| 16L1N30 | H16N30-35T3-F | H16N30-35T3-R | H16N30-35T3 |
| 16L1N30 | G-V-H16N30-35T4-F | G-V-H16N30-35T4-R | H16N30-35T4 long fragment |
| 35L1 | G-H16N30-35T4-F | G-H16N30-35T4-R | H16N30-35T4 short fragment |
| 16L1N30 | H16N30-35T5-F | H16N30-35T5-R | H16N30-35T5 |
| H16N30-35T4 | G-V-H16N30-35T4-31S1-F | G-V-H16N30-35T4-31S1-R | H16N30-35T4-31S1 long fragment |
| 31L1 | G-H16N30-35T4-31S1-F | G-H16N30-35T4-31S1-R | H16N30-35T4-31S1 short fragment |
| H16N30-35T4 | G-V-H16N30-35T4-31S2-F | G-V-H16N30-35T4-31S2-R | H16N30-35T4-31S2 long fragment |

TABLE 2-continued

Templates and primers for PCR reactions used to construct expression vectors

| Template | Upstream primer | Downstream primer | Product |
|---|---|---|---|
| 31L1 | G-H16N30-35T4-31S2-F | G-H16N30-35T4-31S2-R | H16N30-35T4-31S2 short fragment |
| H16N30-35T4 | G-V-H16N30-35T4-31S3-F | G-V-H16N30-35T4-31S3-R | H16N30-35T4-31S3 long fragment |
| 31L1 | G-H16N30-35T4-31S3-F | G-H16N30-35T4-31S3-R | H16N30-35T4-31S3 short fragment |
| H16N30-35T4 | G-V-H16N30-35T4-31S5-F | G-V-H16N30-35T4-31S5-R | H16N30-35T4-31S5 long fragment |
| 31L1 | G-H16N30-35T4-31S5-F | G-H16N30-35T4-31S5-R | H16N30-35T4-31S5 short fragment |

TABLE 3

Sequences of the used primers (SEQ ID NO: 29-60)

| SEQ ID NO: | Primer name | Primer sequence (5'-3') |
|---|---|---|
| 29 | G-V-H16N30-35T1-F | ATACATTTACCTGACCCCAATAAG |
| 30 | G-V-H16N30-35T1-R | TGTTCCTGCATGATAATATATGTTTG |
| 31 | G-H16N30-35T1-F | AACATATATTATCATGCAGGAACAAGCAGGCTGCTGGCCGTGGGC |
| 32 | G-H16N30-35T1-R | CTTATTGGGGTCAGGTAAATGTATCCTGAACACCCTGTACTGCAGGC |
| 33 | G-V-H16N30-35T2-F | AAACCACCTATAGGGGAACACTG |
| 34 | G-V-H16N30-35T2-R | TACACAGGCCCAAACCAGCCGC |
| 35 | G-1-116N30-35T2-F | GCGGCTGGTTTGGGCCTGTGTAGGCGTGGAGGTGGGCAGGGGCC |
| 36 | G-H16N30-35T2-R | CAGTGTTCCCCTATAGGTGGTTTGCAGCCGATCAGGCACAGCTGGG |
| 37 | H16N30-35T3-F | GGCAAAGGAACCCCATGTAACGCTAATCAAGTAAAGGCAGGTGAGTGTCCACCAT |
| 38 | H16N30-35T3-R | ATGGTGGACACTCACCTGCCTTTACTTGATTAGCGTTACATGGGGTTCCTTTGCC |
| 39 | G-V-H16N30-35T4-F | TGGGGTAACCAACTATTTGTTACTG |
| 40 | G-V-H16N30-35T4-R | TAAGCTGTCGCCATATGGTTCTG |
| 41 | G-H16N30-35T4-F | CAGAACCATATGGCGACAGCTTATTCTTCTACCTGAGGAGGGAGC |
| 42 | G-H16N30-35T4-R | CAGTAACAAATAGTTGGTTACCCCAGCAGATGCCGTTGTTGTGG |

TABLE 3 -continued

Sequences of the used primers
(SEQ ID NO: 29-60)

| SEQ ID NO: | Primer name | Primer sequence (5'-3') |
|---|---|---|
| 43 | H16N30-35T5-F | ATGTGCTGCCGTATCTAGT TCAGACAGTACATATAAAA ATGATAACTTTAAGGAG |
| 44 | H16N30-35T5-R | CTCCTTAAAGTTATCATTT TTATATGTACTGTCTGAA CTAGATACGGCAGCACAT |
| 45 | G-V-H16N30-35T4-31S1-F | ATACATTTACCTGACCC CAATAAGTT |
| 46 | G-V-H16N30-35T4-31S1-R | TGCAAGTAGTCTGGAT GTTCCTGC |
| 47 | G-H16N30-335T4-1S1-F | CAGGAACATCCAGACTACT TGCAGTGGGCCACCCCTAC TACAGCAT |
| 48 | G-H16N30-35T4-31S1-R | CTTATTGGCTGTCAGGTAA ATGTATCCTGAACACCCTG TACTGCAGGC |
| 49 | G-V-H16N30-35T4-31S2-F | ATTGGTTGCAAACC ACCTATAGGGG |
| 50 | G-V-H16N30-35T4-31S2-R | AACACCTACACAGGC CCAAACCAGC |
| 51 | G-H16N30-35T4-31S2-F | TGGTTTGGGCCTGTGTAGG TGTTGAGGTGGGCAGGGGC CAGCC |
| 52 | G-H16N30-35T4-3152-R | CCTATAGGTGGTTTGCAAC CAATCAGGCACAGCTGGGT CTGCTTG |
| 53 | G-V-H16N30-35T4-31S3-F | ATAAACACAGTTATTCAG GATGG |
| 54 | G-V-H16N30-35T4-31S3-R | AATTAAACACAATTGTG TTTGTTTGT |
| 55 | G-H16N30-35T4-31S3-F | AACAAACACAATTGTGTTT AATTGGCTGCAAGCCCCCC ATCGGCG |
| 56 | G-H16N30-35T4-31S3-R | CCATCCTGAATAACTGTGT TTATCAGCTCCAGGGGGGG GCAGTCGC |
| 57 | G-V-H16N30-35T4-31S5-F | TATGATTTACAGTTTATT TTTC |
| 58 | G-V-H16N30-35T4-31S5-R | TAATGACATATTTGTACT GCGTG |
| 59 | G-H16N30-35T4-31S5-F | CACGCAGTACAAATATGTC ATTATGCGCCGCCATCGCC AACAGCG |
| 60 | G-H16N30-35T4-31S5-R | TGAAAAATAAACTGTAA ATCATACTCCTCGCCGT GCCTCAGGTACT |

Expression of Mutated Proteins on a Large Scale

The bacteria liquids of *E. coli* carrying recombinant plasmids pTO-T7-H16N30-35T1, pTO-T7-H16N30-35T2, pTO-T7-H16N30-35T3, pTO-T7-H16N30-35T4, pTO-T7-H16N30-35T5, pTO-T7-H16N30-35T4-31S1, pTO-T7-H16N30-35T4-31 S2, pTO-T7-H16N30-35T4-31S3, pTO-T7-H16N30-35T4-31S5 were taken out from the −70° C. refrigerator, separately inoculated into 100 ml of kanamycin-containing LB liquid medium, and cultured at 200 rpm and 37° C. for about 8 hours; then transferred and inoculated into 500 ml of kanamycin-containing LB medium (1 ml of bacterial liquid was inoculated), and cultured continuously. When the bacterial concentration reached an $OD_{600}$ of about 0.6, the culture temperature was lowered to 25° C., and 500 μL, of IPTG was added to each culture flask, and the culturing was continued for 8 hours. At the end of culturing, the bacterial cells were collected by centrifugation. The bacterial cells separately expressing H16N30-35T1, H16N30-35T2, H16N30-35T3, H16N30-35T4, H16N30-35T5, H16N30-35T4-31S1, H16N30-35T4-31 S2, H16N30-35T4-31 S3, H16N30-35T4-31 S5 proteins were obtained.

Disruption of Bacterial Cells Expressing Mutated Proteins

The obtained cells were resuspended in a ratio of 1 g of bacterial cells to 10 mL of a lysate (20 mM Tris buffer, pH 7.2, 300 mM NaCl). The cells were disrupted by a ultra-sonicator for 30 minutes. The lysate containing the disrupted cells was centrifuged at 13500 rpm (30000 g) for 15 minutes, and the supernatant (i.e., the supernatant of the disrupted bacterial cells) was taken.

Chromatographic Purification of Mutated Proteins

Instrument System: AKTA explorer 100 preparative liquid chromatography system, manufactured by GE Healthcare (formerly, Amershan Pharmacia).

Chromatographic media: SP Sepharose 4 Fast Flow (GE Healthcare), CHT-II (purchased from Bio-RAD), and Butyl Sepharose 4 Fast Flow (GE Healthcare).

Buffer solutions: 20 mM phosphate buffer, pH 8.0, 20 mM DTT; and, 20 mM phosphate buffer, pH 8.0, 20 mM DTT, 2 M NaCl.

Samples: the obtained supernatants of the disrupted bacterial cells containing H16N30-35T1, H16N30-35T2, H16N30-35T3, H16N30-35T4, H16N30-35T5, H16N30-35T4-31 S1, H16N30-35T4-31S2, H16N30-35T4-31S3, H16N30-35T4-31S5, respectively.

Elution Procedure:

(1) Cation exchange purification of the supernatants of the disrupted bacterial cells were carried out by using SP Sepharose 4 Fast Flow: the sample was loaded to a column, and then a buffer containing 400 mM NaCl was used to elute undesired proteins, and a buffer containing 800 mM NaCl was used to elute target protein, the fraction eluted by the buffer containing 800 mM NaCl was collected;

(2) Chromatographic purification of the eluted fraction obtained in the previous step was carried out by using CHT II (hydroxyapatite chromatography): the eluted fraction obtained in the previous step was diluted to reduce the concentration of NaCl to 0.5 M; the sample was loaded to a column, and then a buffer containing 500 mM NaCl was used to elute undesired proteins, and a buffer containing 1000 mM NaCl was used to elute target protein, and the fraction eluted by the buffer containing 1000 mM NaCl was collected;

(3) Chromatographic purification of the eluted fraction obtained in the previous step was carried out by using HIC (hydrophobic interaction chromatography): the sample was loaded to a column, and then a buffer containing 1000 mM NaCl was used to elute undesired proteins, and a buffer containing 200 mM NaCl was used to elute target protein, and the fraction eluted by the buffer containing 200 mM NaCl was collected.

150 μL of the eluted fraction obtained in step (3) was taken, added to 30 μL of 6× Loading Buffer, mixed, and incubated in a water bath at 80° C. for 10 min. Then, 10 μl of the sample was electrophoresed in a 10% SDS-polyacrylamide gel at 120 V for 120 min; and the electrophoresis band was visualized by Coomassie blue staining. The results of electrophoresis were shown in FIG. 1. The results showed that after the above purification steps, the proteins H16N30-35T1, H16N30-35T2, H16N30-35T3, H16N30-35T4, H16N30-35T5, H16N30-35T4-31S1, H16N30-35T4-31S2, H16N30-35T4-31 S3, H16N30-35T4-31S5 all had a purity of greater than 95%.

By similar methods, HPV16N30 protein was prepared and purified using *E. coli* and pTO-T7-HPV16L1N30C plasmid; HPV35 L1 protein (SEQ ID NO: 2) was prepared and purified using *E. coli* and pTO-T7-HPV35L1 plasmid; HPV31 L1 protein (SEQ ID NO: 3) was prepared and purified using *E. coli* and pTO-T7-HPV31L1 plasmid.

Western Blotting of Mutated Proteins

Figure 2:
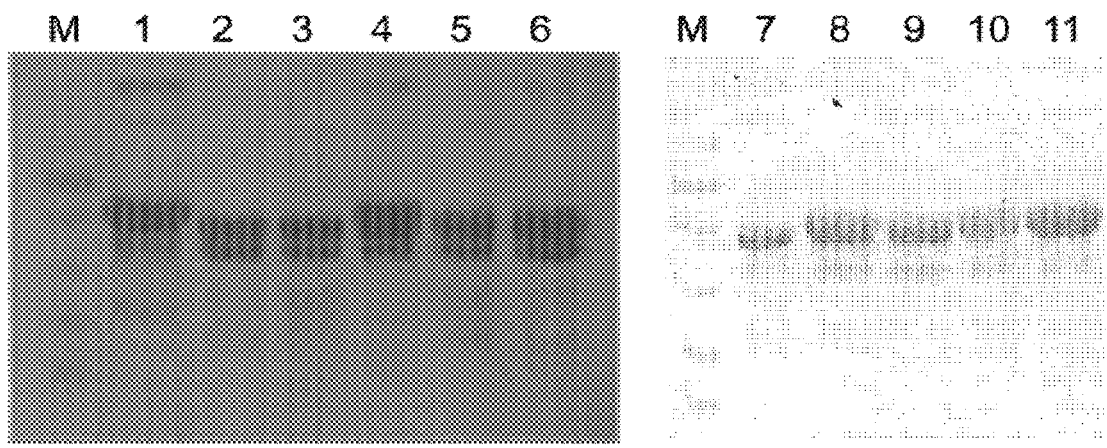
FIG. 2 shows the results of Western Blot detection of H16N30-35T1, H16N30-35T2, H16N30-35T3, H16N30-35T4, H16N30-35T5, H16N30-35T4-31S1, H16N30-35T4-31S2, H16N30-35T4-31S3 and H16N30-35T4-31S5 prepared in Example 1 using a broad-spectrum antibody 4B3. Lane M: protein molecular weight marker; Lane 1: HPV16N30; Lane 2: H16N30-35T1; Lane 3: H16N30-35T2; Lane 4: H16N30-35T3; Lane 5: H16N30-35T4; Lane 6: H16N30-35T5; Lane 7: HPV16N30; Lane 8: H16N30-35T4-31S1; Lane 9: H16N30-35T4-31S2; Lane 10: H16N30-35T4-31S3; Lane 11: H16N30-35T4-31S5. The results showed that the mutated proteins H16N30-35T1, H16N30-35T2, H16N30-35T3, H16N30-35T4, H16N30-35T5, H16N30-35T4-31S1, H16N30-35T4-31S2, H16N30-35T4-31S3, H16N30-35T4-31S5 can be specifically recognized by broad-spectrum antibody 4B3.
Figure 3A:
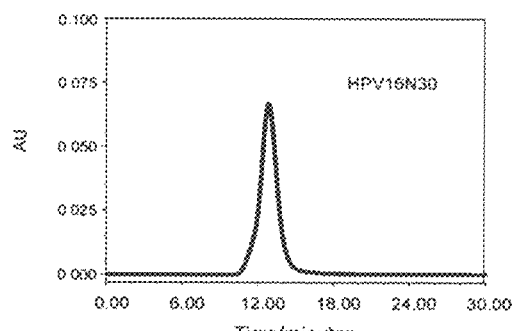
FIGS. 3A-3L show the results of molecular sieve chromatography analysis of samples containing proteins HPV16N30, HPV35 L1, HPV31 L1, H16N30-35T1, H16N30-35T2, H16N30-35T3, H16N30-35T4, H16N30-35T5, H16N30-35T4-31S1, H16N30-35T4-31S2, H16N30-35T4-31S3 and H16N30-35T4-31S5.
Figure 3B:
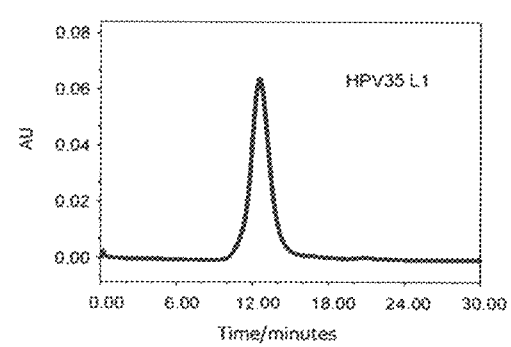
Figure 3C:
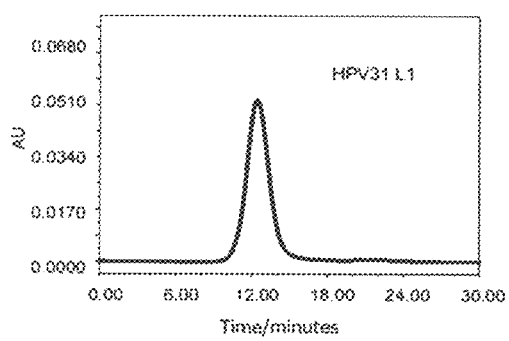
Figure 3D:
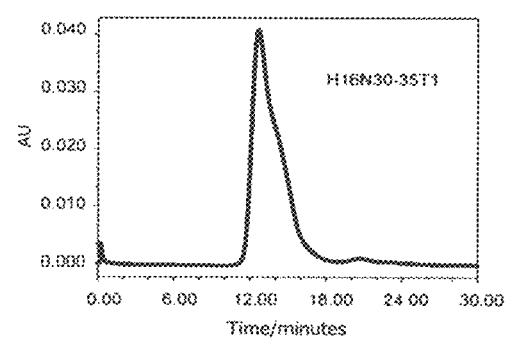
Figure 3E:
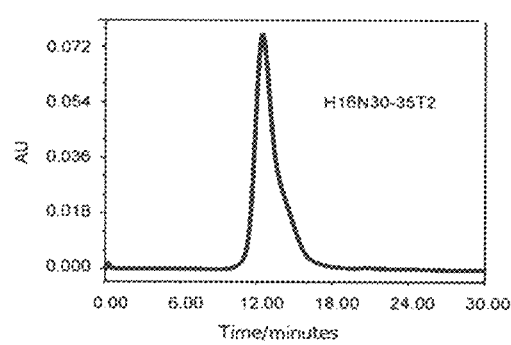
Figure 3F:
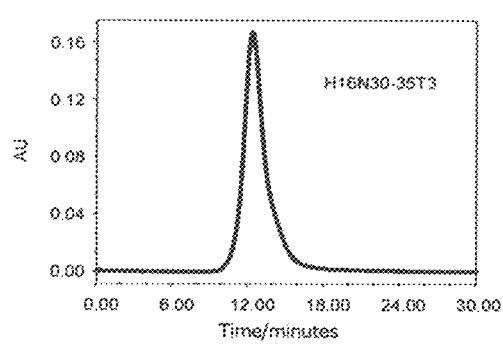
Figure 3G:
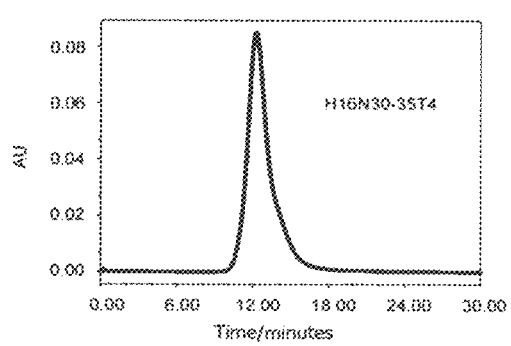
Figure 3H:
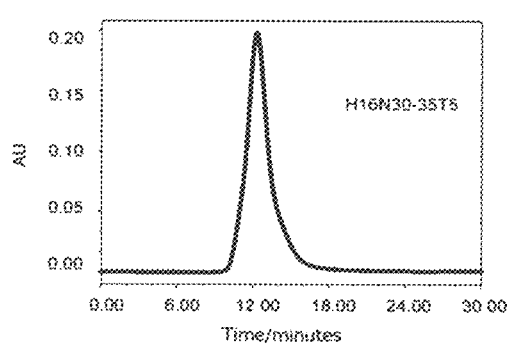
Figure 3I:
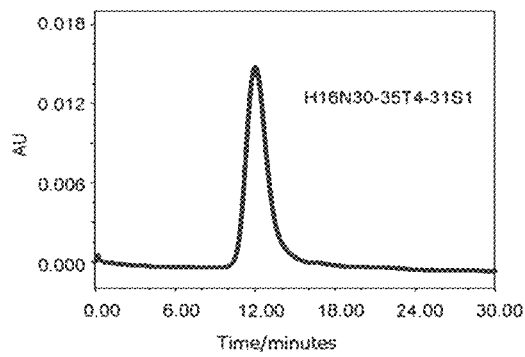
Figure 3J:
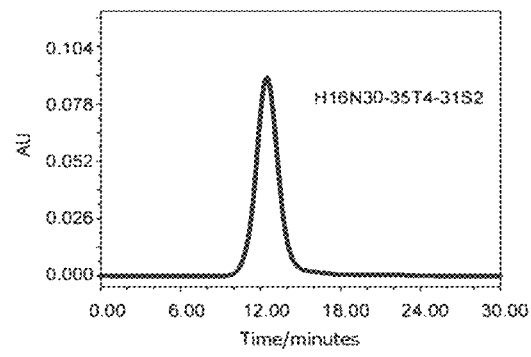
Figure 3K:
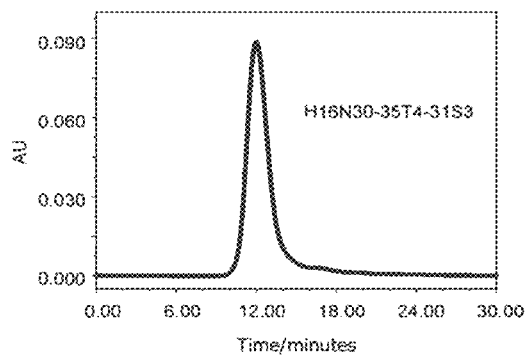
Figure 3L:
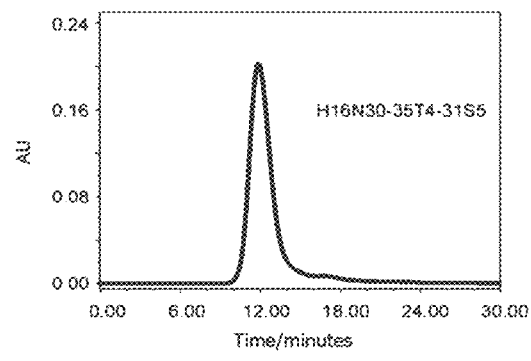
Figure 4A:
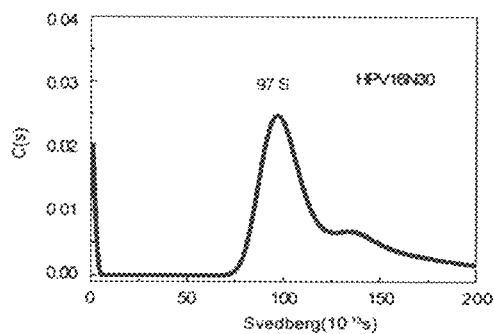
FIGS. 4A-4L show the results of sedimentation rate analysis for HPV16N30 VLP, HPV35 VLP, HPV31 VLP, H16N30-35T1 VLP, H16N30-35T2 VLP, H16N30-35T3 VLP, H16N30-35T4 VLP, H16N30-35T5 VLP, H16N30-35T4-31S1 VLP, H16N30-35T4-31S2 VLP, H16N30-35T4-31S3 VLP, H16N30-35T4-31S5 VLP.
Figure 4B:
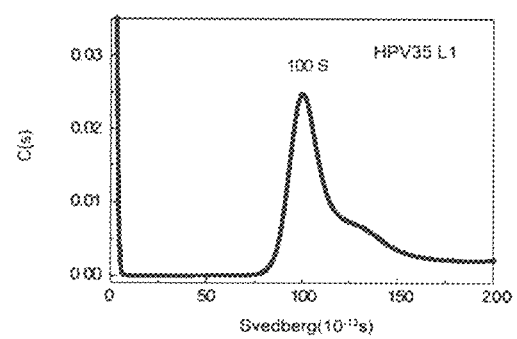
Figure 4C:
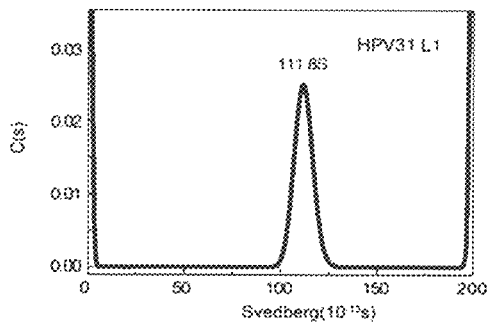
Figure 4D:
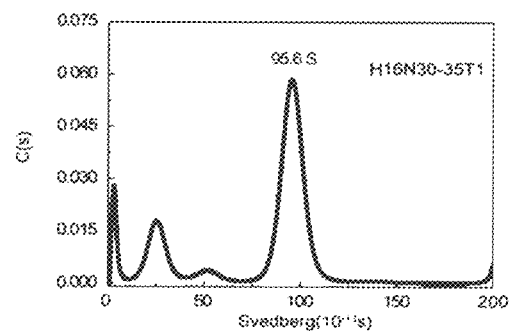
Figure 4E:
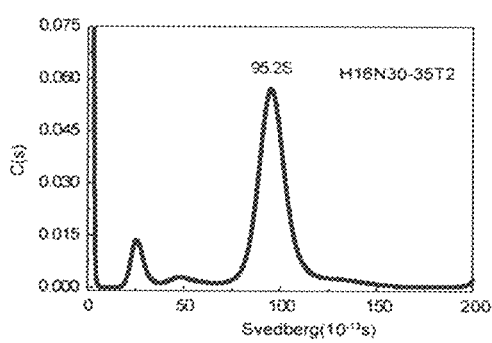
Figure 4F:
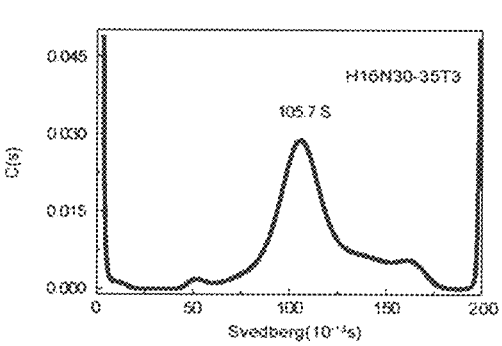
Figure 4G:
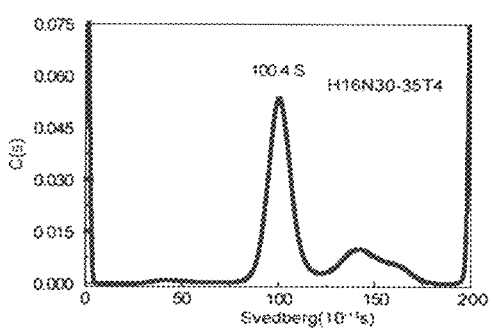
Figure 4H:
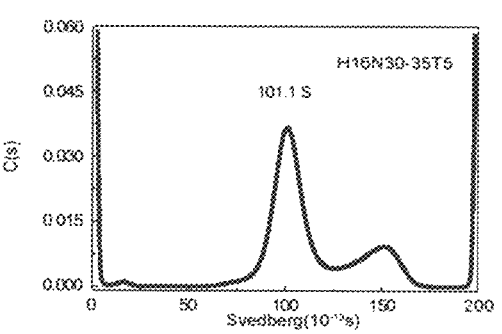
Figure 4I:
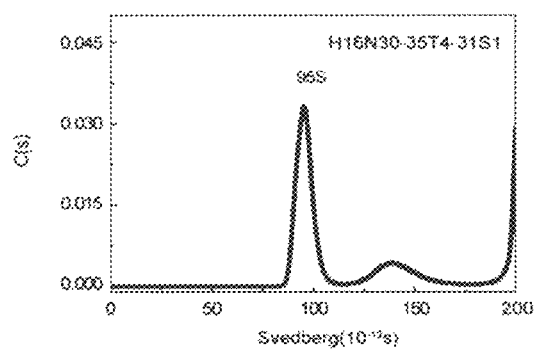
Figure 4J:
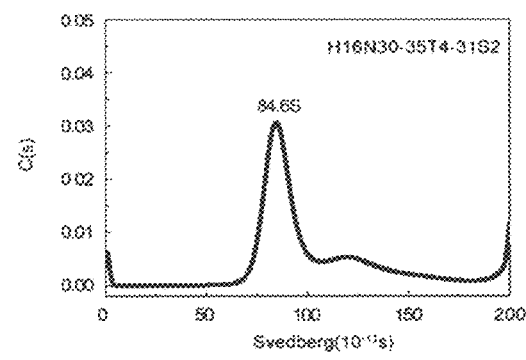
Figure 4K:
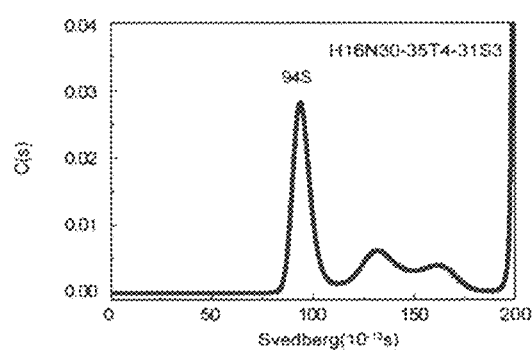
Figure 4L:
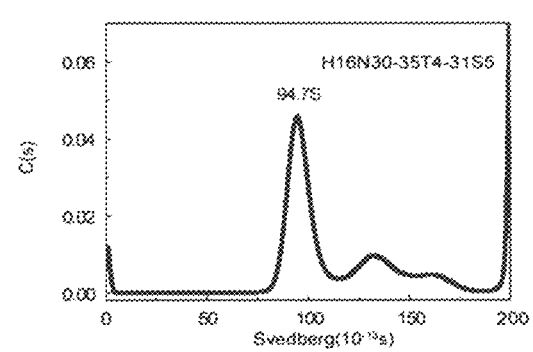
Figure 5A:
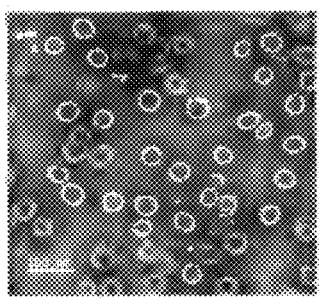
FIGS. 5A-5L show the results of transmission electron microscopy observation for various VLP samples (at a magnification of 100,000 times, Bar=0.1 μm).
Figure 5B:
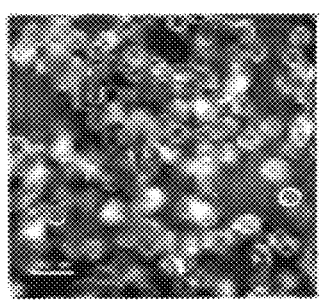
Figure 5C:
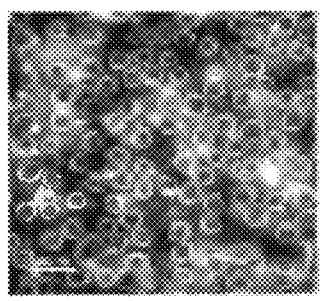
Figure 5D:
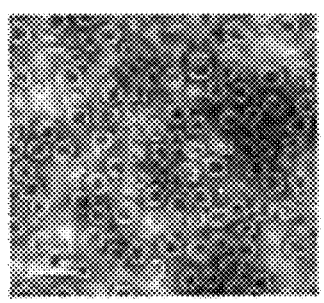
Figure 5E:
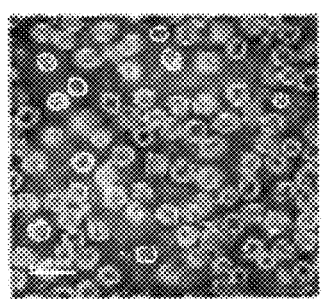
Figure 5F:
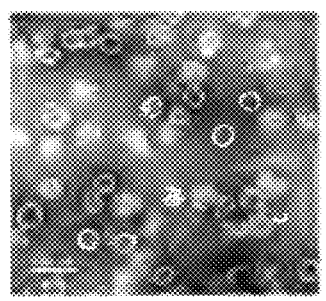
Figure 5G:
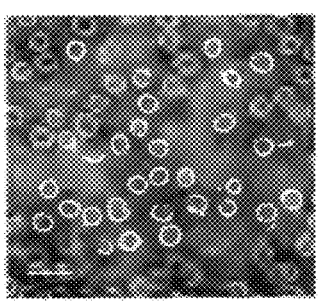
Figure 5H:
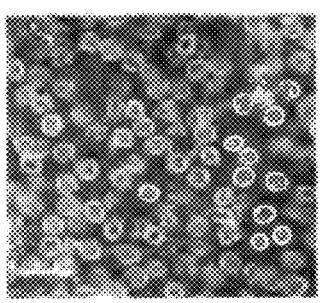
Figure 5I:
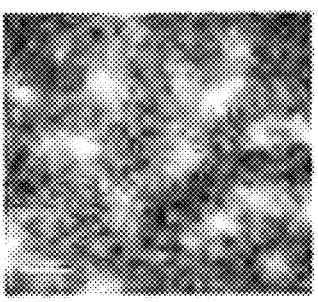
Figure 5J:
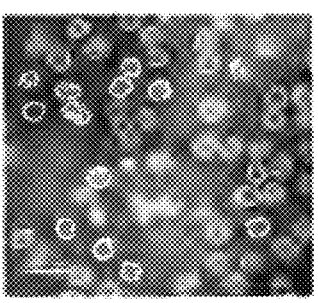
Figure 5K:
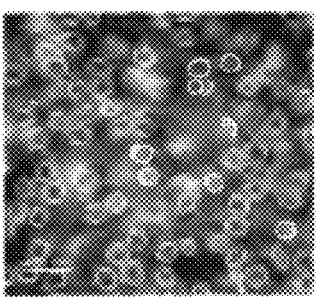
Figure 5L:
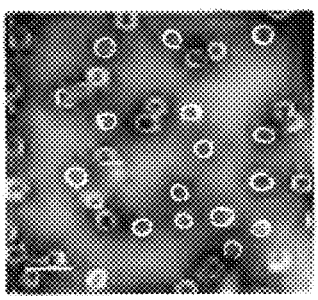
Figure 6A:
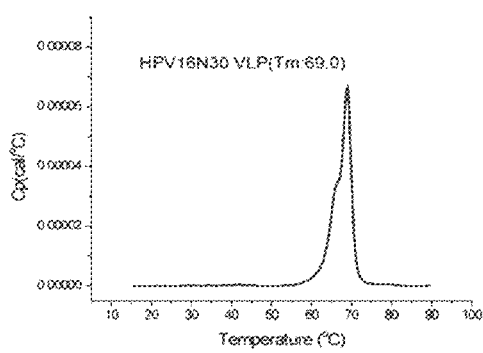
FIGS. 6A-6L show the results of thermal stability evaluation for HPV16N30 VLP, HPV35 VLP, HPV31 VLP, H16N30-35T1 VLP, H16N30-35T2 VLP, H16N30-35T3 VLP, H16N30-35T4 VLP, H16N30-35T5 VLP, H16N30-35T4-31S1 VLP, H16N30-35T4-31S2 VLP, H16N30-35T4-31S3 VLP, H16N30-35T4-31S5 VLP.
Figure 6B:
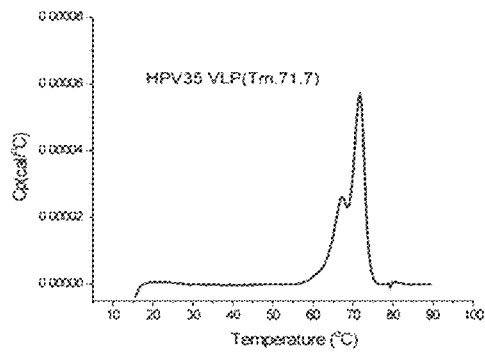
Figure 6C:
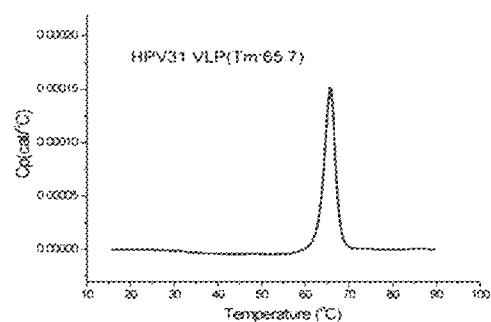
Figure 6D:
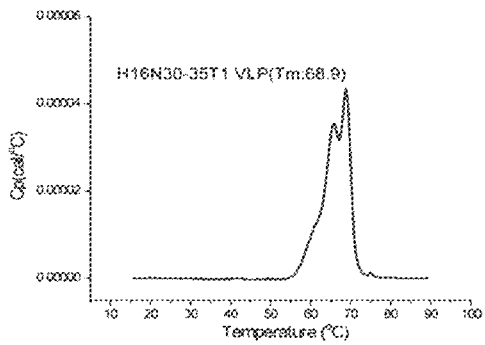
Figure 6E:
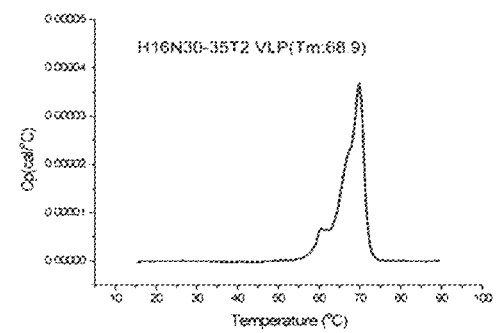
Figure 6F:
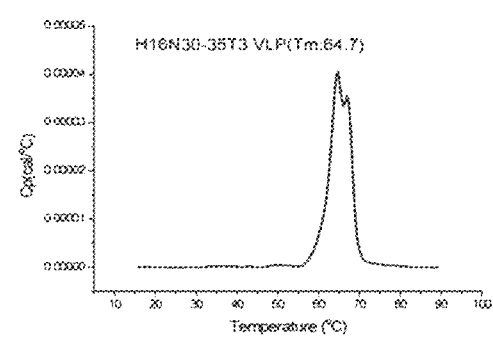
Figure 6G:
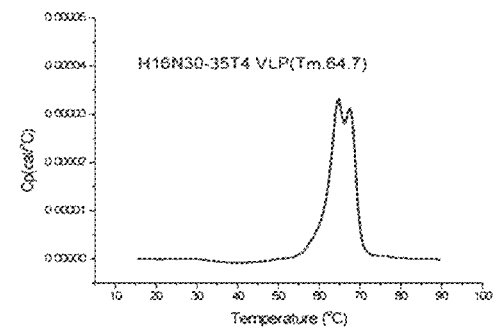
Figure 6H:
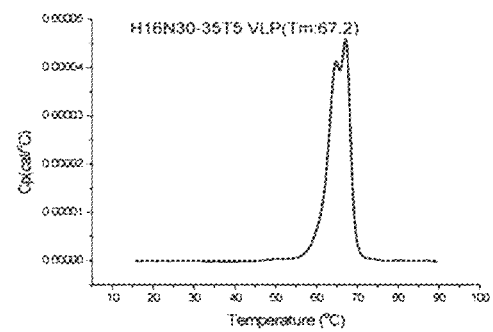
Figure 6I:
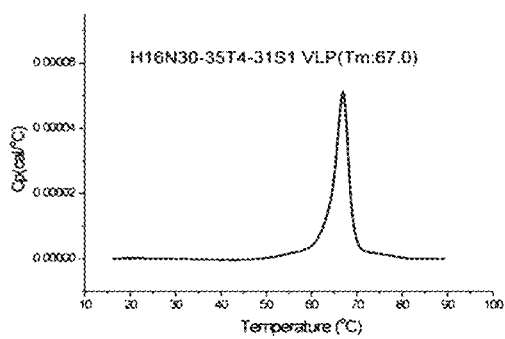
Figure 6J:
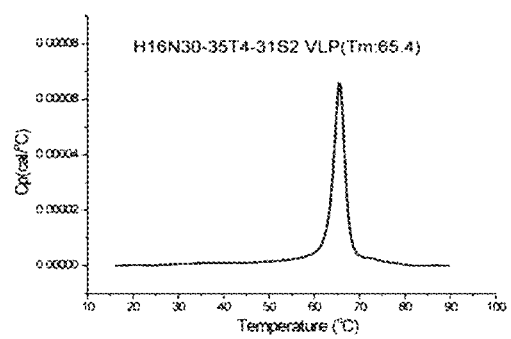
Figure 6K:
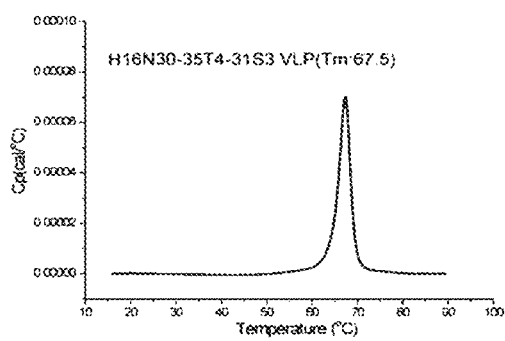
Figure 6L:
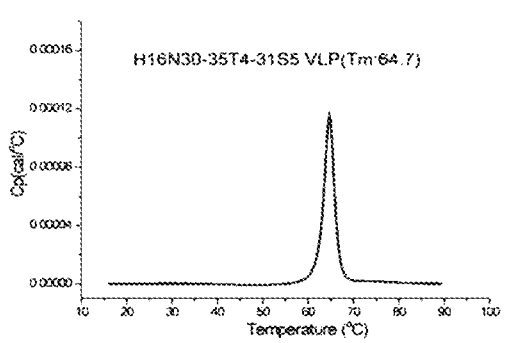

The purified proteins H16N30-35T1, H16N30-35T2, H16N30-35T3, H16N30-35T4, H16N30-35T5, H16N30-35T4-31S1, H16N30-35T4-31S2, H16N30-35T4-31S3, H16N30-35T4-31S5 were subjected to electrophoresis by the above methods. After electrophoresis, Western Blot detection was carried out using a broad-spectrum antibody 4B3 against HPV L1 protein, and the results were shown in FIG. 2. The results showed that the H16N30-35T1, H16N30-35T2, H16N30-35T3, H16N30-35T4, H16N30-35T5, H16N30-35T4-31S1, H16N30-35T4-31 S2, H16N30-35T4-31 S3, H16N30-35T4-31 S5 could be specifically recognized by the broad-spectrum antibody 4B3.

Example 2: Assembly and Particle Morphology Detection of HPV Virus-Like Particles Assembly of HPV Virus-Like Particles A given volume (about 2ml) of the protein H16N30-35T1, H16N30-35T2, H16N30-35T3, H16N30-35T4, H16N30-35T5, H16N30-35T4-31S1, H16N30-35T4-31S2, H16N30-35T4-31S3, or H16N30-35T4-31S5 was dialyzed to (1) 2 L storage buffer (20 mM sodium phosphate buffer, pH 6.5, 0.5M NaCl); (2) 2 L renaturation buffer (50 mM sodium phosphate buffer, pH 6.0, 2 mM $CaCl_2$, 2 mM $MgCl_2$, 0.5 M NaCl); and (3) 20 mM sodium phosphate buffer, pH 7.0, 0.5M NaCl, successively. The dialysis was carried out for 12 h in each of the three buffers.

By similar method, the proteins HPV16N30, HPV35 L1 and HPV31 L1 were assembled into HPV16N30 VLP, HPV35 VLP and HPV31 VLP, respectively.

Molecular Sieve Chromatography Analysis

The dialyzed samples were analyzed by molecular sieve chromatography using a 1120 Compact LC high performance liquid chromatography system from Agilent, USA, using an analytical column of TSK Gel PW5000xl 7.8×300 mm. The results of the analysis were shown in FIGS. 3A-3L. The results showed that for the samples containing proteins H16N30-35T1, H16N30-35T2, H16N30-35T3, H16N30-35T4, H16N30-35T5, H16N30-35T4-31S1, H16N30-35T4-31S2, H16N30-35T4-31S3, H16N30-35T4-31S5, the first protein peaks appeared at around 12 minutes, which was comparable to that of the HPV16N30 VLP, HPV35 VLP and HPV31 VLP. This indicated that the above-prepared proteins were assembled into VLPs.

Sedimentation Velocity Analysis

The instrument used for sedimentation velocity analysis was a Beckman XL-A analytical type ultracentrifuge equipped with optical inspection system, and An-50Ti and An-60Ti rotors. Sedimentation velocity method was used to analyze the sedimentation coefficients of HPV16N30 VLP, HPV35 VLP, HPV31 VLP, H16N30-35T1 VLP, H16N30-35T2 VLP, H16N30-35T3 VLP, H16N30-35T4 VLP, H16N30-35T5 VLP, H16N30-35T4-31S1 VLP, H16N30-35T4-31S2 VLP, H16N30-35T4-31S3 VLP, H16N30-35T4-31S5 VLP. The results were shown in FIGS. 4A-4L. The results showed that the sedimentation coefficients of the H16N30-35T1 VLP, H16N30-35T2 VLP, H16N30-35T3 VLP, H16N30-35T4 VLP, H16N30-35T5 VLP, H16N30-35T4-31S1 VLP, H16N30-35T4-31S2 VLP, H16N30-35T4-31S3 VLP, H16N30-35T4-31S5 VLP were similar to those of the HPV16N30 VLP, HPV35 VLP and HPV31 VLP. This indicated that the H16N30-35T1, H16N30-35T2, H16N30-35T3, H16N30-35T4, H16N30-35T5, H16N30-35T4-31S1, H16N30-35T4-31S2, H16N30-35T4-31S3, H16N30-35T4-31S5 were assembled into virus-like particles similar to wild-type VLP in term of size and morphology.

Morphological Detection of Virus-Like Particles

100 μL of the sample containing VLP was taken for observation of transmission electron microscopy. The instrument used was a 100 kV transmission electron microscope manufactured by JEOL, at a magnification of 100,000 times. Briefly, 13.5 μL of the sample was taken, negatively stained with 2% phosphotungstic acid at pH 7.0, and fixed on a carbon-coated copper mesh, and then observed by the transmission electron microscopy. The results of the observation were shown in FIGS. 5A-5L. The results showed that the H16N30-35T1, H16N30-35T2, H16N30-35T3, H16N30-35T4, H16N30-35T5, H16N30-35T4-31S1, H16N30-35T4-31S2, H16N30-35T4-31S3, H16N30-35T4-31S5 were all assembled into virus-like particles. In addition, the results also showed that the particles formed by these mutated proteins had a radius of about 30 nm, and were uniform in size. This indicated that these mutated proteins were similar to the L1 proteins of HPV16, HPV35 and HPV31, and were capable of forming VLPs of uniform size.

Example 3: Evaluation of Thermal Stability of Virus-Like Particles

The thermal stability of the VLPs formed by H16N30-35T1, H16N30-35T2, H16N30-35T3, H16N30-35T4, H16N30-35T5, H16N30-35T4-31S1, H16N30-35T4-31S2, H16N30-35T4-31S3, H16N30-35T4-31S5 were evaluated using a differential temperature calorimeter VP Capillary DSC purchased from GE Corporation (formerly, MicroCal Corporation), in which the storage buffer of the proteins was used as a control, and each of the proteins was scanned under a heating rate of 1.5° C./min within a range from 10° C. to 90° C. The test results were shown in FIGS. 6A-6L. The results showed that the VLP formed by each of the proteins had extremely high thermal stability.

Example 4: Evaluation 1 of Immunoprotection of Virus-Like Particles in Animals

The immunoprotective properties of VLPs formed by H16N30-35T1, H16N30-35T2, H16N30-35T3, H16N30-35T4, H16N30-35T5, H16N30-35T4-31S1, H16N30-35T4-31S2, H16N30-35T4-31S3, H16N30-35T4-31S5 were evaluated using mice. The animals used for immunization were 5-6 week old BalB/c mice (ordinary grade) (purchased from Shanghai SLAC Laboratory Animal Co., Ltd.).

Figure 7A:
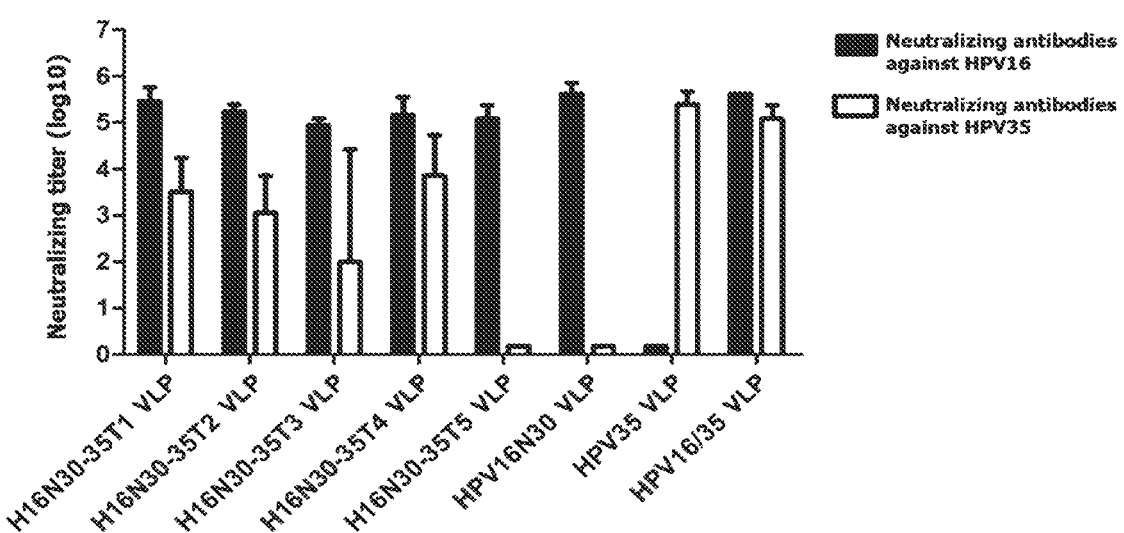
FIG. 7A shows the evaluation results of immunoprotection of the experimental groups of H16N30-35T1 VLP, H16N30-35T2 VLP, H16N30-35T3 VLP, H16N30-35T4 VLP, H16N30-35T5 VLP and the control groups of HPV16N30 VLP, HPV35 VLP and the mixed HPV16/HPV35 VLP in mice. The results showed that the H16N30-35T4 VLP induced high-titer neutralizing antibodies against HPV16 and HPV35 in mice; and its protective effect against HPV16 was comparable to those of the HPV16N30 VLP alone and the mixed HPV16/HPV35 VLP, and was significantly higher than that of the HPV35 VLP alone; in addition, its protective effect against HPV35 was comparable to those of the HPV35 VLP alone, the mixed HPV16/HPV35 VLP, and was significantly higher than that of the HPV16N30 VLP alone. This indicates that the H16N30-35T4 VLP can be used as an effective vaccine against HPV16 infection and HPV35 infection, and can be used in place of the mixed vaccine containing HPV16 VLP and HPV35 VLP.

The above-prepared H16N30-35T1 VLP, H16N30-35T2 VLP, H16N30-35T3 VLP, H16N30-35T4 VLP, H16N30-35T5 VLP, HPV16N30 VLP, HPV35 VLP, and the mixed HPV16/HPV35 VLP (i.e., a mixture of HPV16N30 VLP and HPV35 VLP) were adsorbed onto aluminum adjuvant, respectively. The mice were divided into 8 groups according to different immunogens, and each group contained 5 mice. The immunization procedure was: primary immunization was carried out at the $0^{th}$ week; and booster immunizations were carried out at the $2^{nd}$ and $4^{th}$ weeks respectively. The immunization method was intraperitoneal injection, and the immunogens and doses used were as shown in Table 4. At the $8^{th}$ week after the primary immunization, venous blood was collected from eyeball, and the serum was separated, and then the titers of the neutralizing antibodies in the serum were measured. The test results were shown in FIG. 7A. The results showed that the H16N30-35T4 VLP induced high-titer neutralizing antibodies against HPV16 and HPV35 in mice; and its protective effect against HPV16 was comparable to those of the HPV16N30 VLP alone and the mixed HPV16/HPV35 VLP, and was significantly higher than that of the HPV35 VLP alone; and its protective effect against HPV35 was comparable to those of the HPV35 VLP alone, the mixed HPV16/HPV35 VLP, and was significantly higher than that of the HPV16N30 VLP alone. This indicated that the H16N30-35T4 VLP could be used as an effective vaccine against HPV16 infection and HPV35 infection, and could be used in place of the mixed vaccine containing HPV16 VLP and HPV35 VLP.

TABLE 4

Immunization protocols

| Immunization antigen | Adjuvant | Immunization dose | Number | Immunization protocol (week) |
|---|---|---|---|---|
| H16N30-35T1 VLP | Aluminum adjuvant | 5 μg | 5 | 0, 2, 4 |
| H16N30-35T2 VLP | Aluminum adjuvant | 5 μg | 5 | 0, 2, 4 |
| H16N30-35T3 VLP | Aluminum adjuvant | 5 μg | 5 | 0, 2, 4 |
| H16N30-35T4 VLP | Aluminum adjuvant | 5 μg | 5 | 0, 2, 4 |
| H16N30-35T5 VLP | Aluminum adjuvant | 5 μg | 5 | 0, 2, 4 |
| HPV16N30 VLP | Aluminum adjuvant | 5 μg | 5 | 0, 2, 4 |
| HPV35 VLP | Aluminum adjuvant | 5 μg | 5 | 0, 2, 4 |
| HPV16/HPV35 VLP | Aluminum adjuvant | 5 μg for each VLP | 5 | 0, 2, 4 |

Figure 7B:
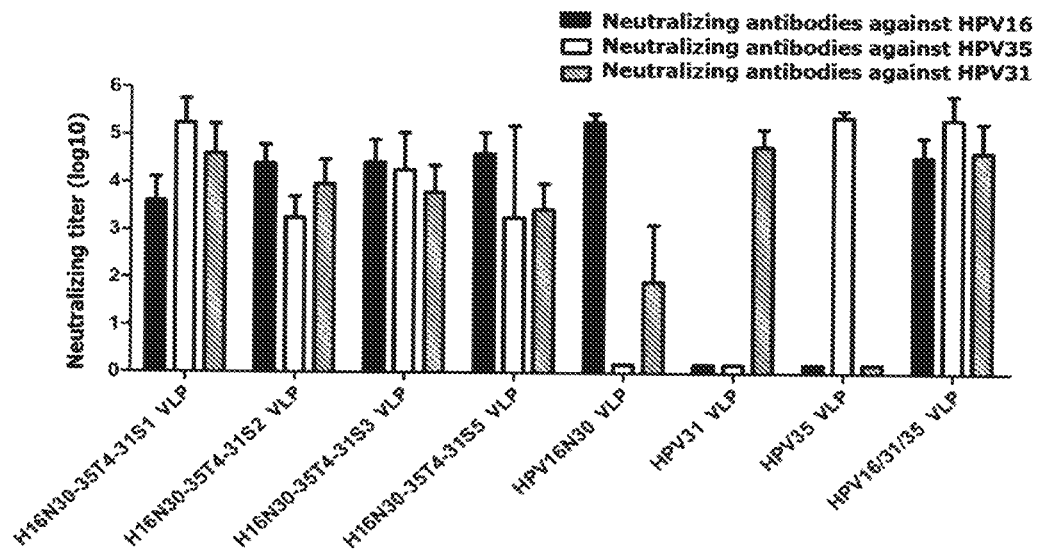
FIG. 7B shows the evaluation results of immunoprotection of the experimental groups of H16N30-35T4-31S1 VLP, H16N30-35T4-31S2 VLP, H16N30-35T4-31S3 VLP and H16N30-35T4-31S5 VLP, and the control groups of HPV16N30 VLP, HPV31 VLP, HPV35 VLP and the mixed HPV16/HPV35/HPV31 VLP in mice. The results showed that the H16N30-35T4-31S1 VLP, H16N30-35T4-31S2 VLP and H16N30-35T4-31S3 VLP induced high-titer neutralizing antibodies against HPV16, HPV35 and HPV31 in mice; and their protection effects against HPV16 were comparable to those of the HPV16N30 VLP alone and the mixed HPV16/HPV35/HPV31 VLP, and were significantly higher than those of the HPV35 VLP alone and the HPV31 VLP alone; and their protective effects against HPV35 were comparable to those of the HPV35 VLP alone and the mixed HPV16/HPV35/HPV31 VLP, and were significantly higher than those of the HPV16N30 VLP alone and the HPV31 VLP alone; and their protection effects against HPV31 were comparable to those of the HPV31 VLP alone and the mixed HPV16/HPV35/HPV31 VLP, and were significantly higher than those of the HPV16N30 VLP alone and the HPV35 VLP alone. This indicates that the H16N30-35T4-31S1 VLP, H16N30-35T4-31S2 VLP and H16N30-35T4-31S3 VLP can be used as effective vaccines against HPV16 infection, HPV35 infection and HPV31 infection, and can be used in place of the mixed vaccine containing HPV16 VLP, HPV35 VLP and HPV31 VLP.

In addition, the above-prepared H16N30-35T4-31S1 VLP, H16N30-35T4-31S2 VLP, H16N30-35T4-31S3 VLP, H16N30-35T4-31S5 VLP, HPV16N30 VLP, HPV31 VLP, HPV35 VLP, as well as the mixed HPV16/HPV35/HPV31 (i.e., a mixture of HPV16N30 VLP, HPV35 VLP and HPV31 VLP) were adsorbed onto aluminum adjuvant, respectively. Mice were divided into 8 groups according to different immunogens, and each group contained 5 mice. The immunization procedure was: primary immunization was carried out at the $0^{th}$ week; booster immunizations were carried out at the $2^{nd}$ and $4^{th}$ weeks respectively. The immunization method was intraperitoneal injection, and the immunogens and doses used were as shown in Table 5. At the $8^{th}$ week after the primary immunization, venous blood was collected from eyeball, and the serum was separated, and then the titers of the neutralizing antibodies in the serum were measured. The test results were shown in FIG. 7B. The results showed that the H16N30-35T4-31S1 VLP, H16N30-35T4-31S2 VLP and H16N30-35T4-31S3 VLPs induced high-titer neutralizing antibodies against HPV16, HPV35 and HPV31 in mice; and their protection effects against HPV16 were comparable to those of the HPV16N30 VLP alone and the mixed HPV16/HPV35/HPV31 VLP, and were significantly higher than those of the HPV35 VLP alone and the HPV31 VLP alone; and their protective effects against HPV35 were comparable to those of the HPV35 VLP alone, the mixed HPV16/HPV35/HPV31 VLP, and were significantly higher than those of the HPV16N30 VLP alone and the HPV31 VLP alone; and their protection effects against HPV31 were comparable to those of the HPV31 VLP alone and the mixed HPV16/HPV35/HPV31 VLP, and were significantly higher than those of the HPV16N30 VLP alone and the HPV35 VLP alone. This indicated that the H16N30-35T4-31S1 VLP, H16N30-35T4-31S2 VLP and H16N30-35T4-31S3 VLP could be used as effective vaccines against HPV16 infection, HPV35 infection and HPV31 infection, and could be used in place of the mixed vaccine containing HPV16 VLP, HPV35 VLP and HPV31 VLP.

TABLE 5

Immunization protocols

| Immunization antigen | Adjuvant | Immunization dose | Number | Immunization protocol (week) |
|---|---|---|---|---|
| H16N30-35T4-31S1 VLP | aluminum adjuvant | 5 μg | 5 | 0, 2, 4 |
| H16N30-35T4-31S2 VLP | aluminum adjuvant | 5 μg | 5 | 0, 2, 4 |
| H16N30-35T4-31S3 VLP | aluminum adjuvant | 5 μg | 5 | 0, 2, 4 |
| H16N30-35T4-31S5 VLP | aluminum adjuvant | 5 μg | 5 | 0, 2, 4 |
| HPV16N30 VLP | aluminum adjuvant | 5 μg | 5 | 0, 2, 4 |
| HPV31 VLP | aluminum adjuvant | 5 μg | 5 | 0, 2, 4 |
| HPV35 VLP | aluminum adjuvant | 5 μg | 5 | 0, 2, 4 |
| HPV16/HPV35/HPV31 VLP | aluminum adjuvant | 5 μg for each VLP | 5 | 0, 2, 4 |

Example 5: Evaluation 2 of Immunoprotection of Virus-Like Particles in Animals

ED50 of H16N30-35T4 VLP

Six weeks old BalB/c female mice (8 mice) were immunized with aluminum adjuvant by single intraperitoneal injection, in which the experimental groups were administered with the H16N30-35T4 VLP (immunization doses were 0.300 μg, 0.100 μg, 0.033 μg, 0.011 μg, and 0.004 μg), the control groups were administered with the HPV16N30 VLP alone and the HPV35 VLP alone (immunization doses were 0.300 μg, 0.100 μg, 0.033 μg, 0.011 μg, 0.004 μg), or the mixed HPV16/HPV35 VLP (immunization doses for each VLP were 0.300 μg, 0.100 μg, 0.033 μg, 0.011 μg, 0.004 μg); and the immunization volume was 1 mL. In the $5^{th}$ week after immunization, venous blood was collected from eyeball and the HPV antibodies in the blood were detected. ED50 for inducing seroconversion (i.e. inducing the generation of antibodies in mice) was calculated for each sample, by Reed-Muench method (Reed L J M H. A simple method of estimating fifty percent endpoints. Am J Hyg. 1938; 27:493-7). The results were shown in Tables 6-9.

TABLE 6

ED$_{50}$ values of HPV16N30 VLP for inducing the generation of anti-HPV16 and anti-HPV35 antibodies in mice

| Type | Dose (μg) | Number of mice (mice) | Seroconversion number (mice) | Seroconversion rate | ED50 (μg) |
|---|---|---|---|---|---|
| HPV16 | 0.300 | 8 | 8 | 100.00% | 0.019 |
| | 0.100 | 8 | 8 | 100.00% | |
| | 0.033 | 8 | 5 | 72.73% | |
| | 0.011 | 8 | 3 | 27.27% | |
| | 0.004 | 8 | 0 | 0.00% | |
| HPV35 | 0.300 | 8 | 0 | 0.00% | >0.3 |
| | 0.100 | 8 | 0 | 0.00% | |
| | 0.033 | 8 | 0 | 0.00% | |
| | 0.011 | 8 | 0 | 0.00% | |
| | 0.004 | 8 | 0 | 0.00% | |

TABLE 7

ED$_{50}$ values of HPV35 VLP for inducing the generation of anti-HPV16 and anti-HPV35 antibodies in mice

| Type | Dose (μg) | Number of mice (mice) | Seroconversion number (mice) | Seroconversion rate | ED50 (μg) |
|---|---|---|---|---|---|
| HPV16 | 0.300 | 8 | 0 | 0.00% | >0.3 |
| | 0.100 | 8 | 0 | 0.00% | |
| | 0.033 | 8 | 0 | 0.00% | |
| | 0.011 | 8 | 0 | 0.00% | |
| | 0.004 | 8 | 0 | 0.00% | |
| HPV35 | 0.300 | 8 | 5 | 70.00% | 0.196 |
| | 0.100 | 8 | 2 | 18.18% | |
| | 0.033 | 8 | 0 | 0.00% | |
| | 0.011 | 8 | 0 | 0.00% | |
| | 0.004 | 8 | 0 | 0.00% | |

TABLE 8

ED$_{50}$ values of the mixed HPV16/HPV35 VLP for inducing the generation of anti-HPV16 and anti-HPV35 antibodies in mice

| Type | Dose (μg) | Number of mice (mice) | Seroconversion number (mice) | Seroconversion rate | ED50 (μg) |
|---|---|---|---|---|---|
| HPV16 | 0.300 | 8 | 7 | 95.65% | 0.023 |
| | 0.100 | 8 | 8 | 93.75% | |
| | 0.033 | 8 | 6 | 70.00% | |
| | 0.011 | 8 | 1 | 9.09% | |
| | 0.004 | 8 | 0 | 0.00% | |
| HPV35 | 0.300 | 8 | 8 | 100.00% | 0.042 |
| | 0.100 | 8 | 8 | 100.00% | |
| | 0.033 | 8 | 3 | 37.50% | |
| | 0.011 | 8 | 0 | 0.00% | |
| | 0.004 | 8 | 0 | 0.00% | |

TABLE 9

ED$_{50}$ values of H16N30-35T4 VLP for inducing the generation of anti-HPV16 and anti-HPV35 antibodies in mice

| Type | Dose (μg) | Number of mice (mice) | Seroconversion number (mice) | Seroconversion rate | ED50 (μg) |
|---|---|---|---|---|---|
| HPV16 | 0.300 | 8 | 7 | 92.86% | 0.081 |
| | 0.100 | 8 | 5 | 60.00% | |
| | 0.033 | 8 | 1 | 8.33% | |
| | 0.011 | 8 | 0 | 0.00% | |
| | 0.004 | 8 | 0 | 0.00% | |
| HPV35 | 0.300 | 8 | 5 | 100.00% | 0.264 |
| | 0.100 | 8 | 1 | 100.00% | |
| | 0.033 | 8 | 0 | 22.22% | |
| | 0.011 | 8 | 0 | 6.67% | |
| | 0.004 | 8 | 0 | 0.00% | |

The results showed that after 5 weeks of immunization in mice, the ED$_{50}$ of the H16N30-35T4 VLP for inducing the generation of anti-HPV16 antibody in mice was comparable to those of the HPV16N30 VLP alone and the mixed HPV16/HPV35 VLP, and was significantly better than that of the HPV35 VLP alone; and the ED$_{50}$ thereof for inducing the generation of anti-HPV35 antibody in mice was comparable to those of the HPV35 VLP alone and the mixed HPV16/HPV35 VLP, and was significantly better than that of the HPV16N30 VLP alone. This indicated that the H16N30-35T4 VLP had good cross-immunogenicity and cross-protection against HPV16 and HPV35.

ED50 of H16N30-35T4-31S3 VLP

Six weeks old BalB/c female mice (8 mice) were immunized with aluminum adjuvant by single intraperitoneal injection. The experimental groups were administered with the H16N30-35T4-31S3 VL (immunization doses were 0.300 μg, 0.100 μg, 0.033 μg, 0.011 μg, 0.004 μg); the control groups were administered with the HPV16N30 VLP alone, the HPV35 VLP alone, the HPV31 VLP alone (immunization doses were 0.300 μg, 0.100 μg, 0.033 μg, 0.011 μg, 0.004 μg), and the mixed HPV16/HPV35/HPV31 VLP (immunization doses of each VLP were 0.300 μg, 0.100 μg, 0.033 μg, 0.011 μg, 0.004 μg); and the immunological volume was 1 mL. In the 5$^{th}$ week after immunization, venous blood was collected from eyeball and the HPV antibodies in the blood were detected. ED50 for inducing seroconversion (i.e. inducing the generation of antibodies in mice) was calculated for each sample, by Reed-Muench method (Reed L J M H. A simple method of estimating fifty percent endpoints. Am J Hyg. 1938; 27:493-7). The results were shown in Tables 10-14.

TABLE 10

ED$_{50}$ values of HPV16N30 VLP for inducing the generation of anti-HPV16, anti-HPV35 and anti-HPV31 antibodies in mice

| Type | Dose (μg) | Number of mice (mice) | Seroconversion number (mice) | Seroconversion rate | ED50 (μg) |
|---|---|---|---|---|---|
| HPV16 | 0.300 | 8 | 7 | 96.67% | 0.008 |
| | 0.100 | 8 | 8 | 95.65% | |
| | 0.033 | 8 | 8 | 93.33% | |
| | 0.011 | 8 | 6 | 66.67% | |
| | 0.004 | 8 | 0 | 0.00% | |
| HPV35 | 0.300 | 8 | 0 | 0.00% | >0.3 |
| | 0.100 | 8 | 0 | 0.00% | |
| | 0.033 | 8 | 0 | 0.00% | |
| | 0.011 | 8 | 0 | 0.00% | |
| | 0.004 | 8 | 0 | 0.00% | |
| HPV31 | 0.300 | 8 | 0 | 0.00% | >0.3 |
| | 0.100 | 8 | 0 | 0.00% | |
| | 0.033 | 8 | 0 | 0.00% | |
| | 0.011 | 8 | 0 | 0.00% | |
| | 0.004 | 8 | 0 | 0.00% | |

TABLE 11

$ED_{50}$ values of HPV35 VLP for inducing the generation of anti-HPV16, anti-HPV35 and anti-HPV31 antibodies in mice

| Type | Dose (μg) | Number of mice (mice) | Seroconversion number (mice) | Seroconversion rate | ED50 (μg) |
|---|---|---|---|---|---|
| HPV16 | 0.300 | 8 | 0 | 0.00% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |
| HPV35 | 0.300 | 8 | 8 | 100.00% | 0.017 |
|  | 0.100 | 8 | 8 | 100.00% |  |
|  | 0.033 | 8 | 7 | 90.00% |  |
|  | 0.011 | 8 | 2 | 22.22% |  |
|  | 0.004 | 8 | 0 | 0.00% |  |
| HPV31 | 0.300 | 8 | 0 | 0.00% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |

TABLE 12

$ED_{50}$ values of HPV31 VLP for inducing the generation of anti-HPV16, anti-HPV35 and anti-HPV31 antibodies in mice

| Type | Dose (μg) | Number of mice (mice) | Seroconversion number (mice) | Seroconversion rate | ED50 (μg) |
|---|---|---|---|---|---|
| HPV16 | 0.300 | 8 | 0 | 0.00% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |
| HPV35 | 0.300 | 8 | 0 | 0.00% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |
| HPV31 | 0.300 | 8 | 8 | 100.00% | 0.014 |
|  | 0.100 | 8 | 8 | 100.00% |  |
|  | 0.033 | 8 | 7 | 91.67% |  |
|  | 0.011 | 8 | 3 | 40.00% |  |
|  | 0.004 | 8 | 1 | 7.14% |  |

TABLE 13

$ED_{50}$ values of the mixed HPV16/HPV35/HPV31 VLP for inducing the generation of anti-HPV16, anti-HPV35 and anti-HPV31 antibodies in mice

| Type | Dose (μg) | Number of mice (mice) | Seroconversion number (mice) | Seroconversion rate | ED50 (μg) |
|---|---|---|---|---|---|
| HPV16 | 0.300 for each VLP | 8 | 7 | 95.24% | 0.043 |
|  | 0 100 for each VLP | 8 | 5 | 76.47% |  |
|  | 0.033 for each VLP | 8 | 1 | 42.11% |  |
|  | 0.011 for each VLP | 8 | 5 | 33.33% |  |
|  | 0.004 for each VLP | 8 | 2 | 9.09% |  |
| HPV35 | 0.300 for each VLP | 8 | 8 | 100.00% | 0.011 |
|  | 0.100 for each VLP | 8 | 8 | 100.00% |  |
|  | 0.033 for each VLP | 8 | 8 | 100.00% |  |
|  | 0.011 for each VLP | 8 | 4 | 50.00% |  |
|  | 0.004 for each VLP | 8 | 0 | 0.00% |  |
| HPV31 | 0 300 for each VLP | 8 | 8 | 100.00% | 0.006 |
|  | 0.100 for each VLP | 8 | 8 | 100.00% |  |
|  | 0.033 for each VLP | 8 | 8 | 100.00% |  |
|  | 0.011 for each VLP | 8 | 7 | 88.89% |  |
|  | 0.004 for each VLP | 8 | 1 | 11.11% |  |

TABLE 14

$ED_{50}$ values of H16N30-35T4-31S3 VLP for inducing the generation of anti-HPV16, anti-HPV35 and anti-HPV31 antibodies in mice

| Type | Dose (μg) | Number of mice (mice) | Seroconversion number (mice) | Seroconversion rate | ED50 (μg) |
|---|---|---|---|---|---|
| HPV16 | 0.300 | 8 | 8 | 100.00% | 0.017 |
|  | 0.100 | 8 | 7 | 94.44% |  |
|  | 0.033 | 8 | 7 | 83.33% |  |
|  | 0.011 | 8 | 3 | 30.00% |  |
|  | 0.004 | 8 | 0 | 0.00% |  |
| HPV35 | 0.900 | 8 | 6 | 86.67% | 0.100 |
|  | 0.300 | 8 | 3 | 50.00% |  |
|  | 0.033 | 8 | 1 | 22.22% |  |
|  | 0.011 | 8 | 3 | 13.64% |  |
|  | 0.004 | 8 | 0 | 0.00% |  |
| HPV31 | 0.900 | 8 | 5 | 80.00% | 0.121 |
|  | 0.100 | 8 | 2 | 43.75% |  |
|  | 0.033 | 8 | 5 | 29.41% |  |
|  | 0.011 | 8 | 0 | 0.00% |  |
|  | 0.004 | 8 | 0 | 0.00% |  |

The results showed that after 5 weeks of immunization in mice, the $ED_{50}$ of H16N30-35T4-31S3 VLP for inducing the generation of anti-HPV16 antibody in mice was comparable to those of the HPV16N30 VLP alone and the mixed HPV16/HPV35/HPV31 VLP, and was significantly better than those of the HPV35 VLP alone and the HPV31 VLP alone; and the $ED_{50}$ thereof for inducing the generation of anti-HPV35 antibody in mice was comparable to those of the HPV35 VLP alone and the mixed HPV16/HPV35/HPV31 VLP, and was significantly better than those of the HPV16N30 VLP alone and the HPV31 VLP alone; the $ED_{50}$ thereof for inducing the generation of anti-HPV31 antibody in mice was comparable to those of the HPV31 VLP alone and the mixed HPV16/HPV35/HPV31 VLP, and was significantly better than those of the HPV16N30 VLP alone and the HPV35 VLP alone. This indicated that the H16N30-35T4-31S3 VLP had good cross-immunogenicity and cross-protection against HPV16, HPV35 and HPV31.

Evaluation of Titers of Neutralizing Antibodies in Serum After Immunization with H16N30-35T4 VLP in Mice In this experiment, the immunization protocols were shown in Table 15. All mice (6-weeks old BalB/c female mice) were divided into 3 groups: 10 μg dose group (immunization dose was 10 μg, using aluminum adjuvant), 1 μg dose group (immunization dose was 1 μg, using aluminum adjuvant), and 0.1 μg dose group (immunization dose was 0.1 μg, using aluminum adjuvant). Each group was subdivided into 4 subgroups, in which the control subgroups 1 and 2 were immunized with the HPV16N30 VLP alone and the HPV35 VLP alone respectively, the control subgroup 3 was immunized with the mixed HPV16/HPV35 VLP, and the experimental subgroup was immunized with H16N30-35T4 VLP.

Figure 8A:
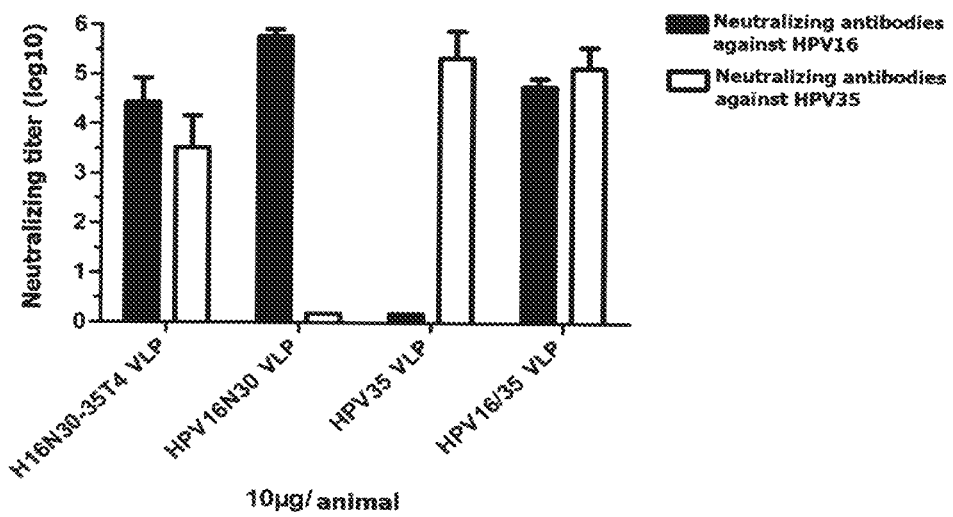
FIGS. 8A-8C show the evaluation results of neutralizing antibody titers in mouse serum after immunization of mice with H16N30-35T4 VLP.
Figure 8B:
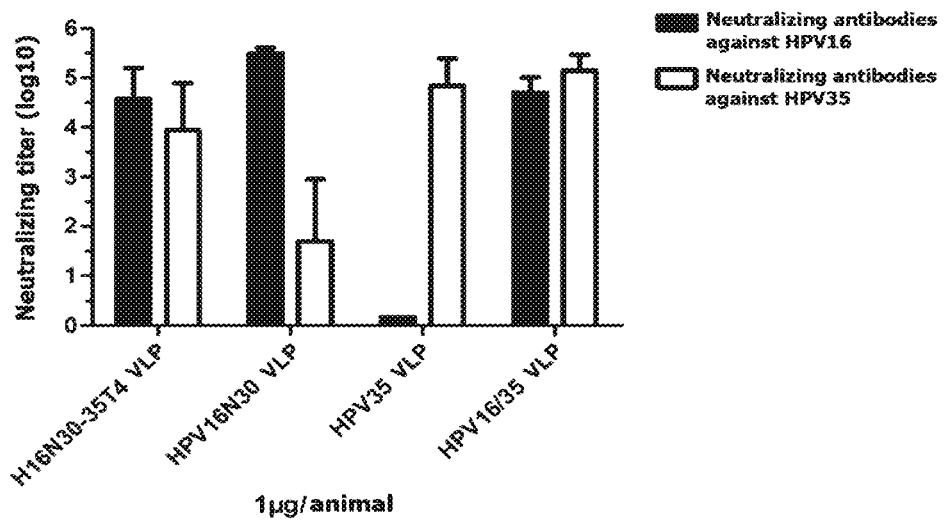
Figure 8C:
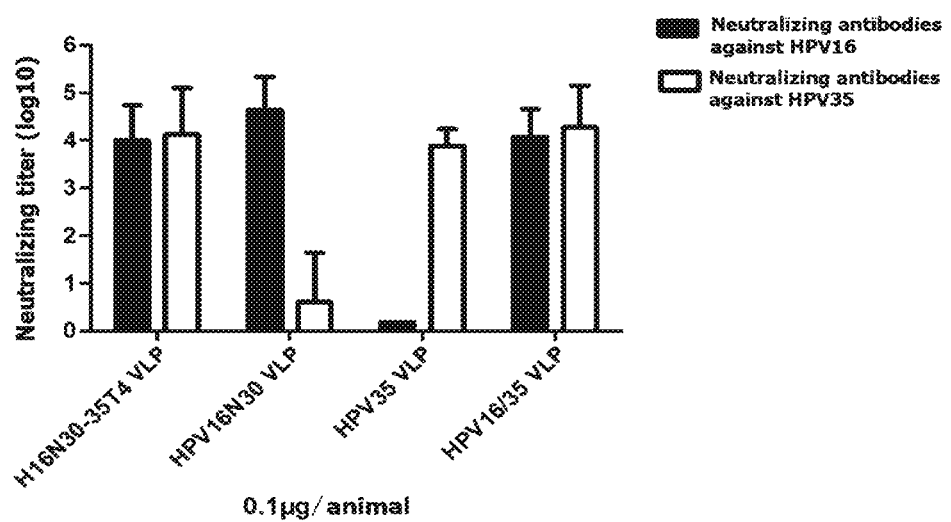

Six mice per subgroup were immunized by intraperitoneal injection, and the immunization doses were 10 μg, 1 μg, and 0.1 μg, respectively, and the injection volume was 1 ml. All mice were immunized initially at the $0^{th}$ week, and boosted at the $2^{nd}$ and $4^{th}$ weeks, respectively. Blood samples were collected from the mice via orbital bleeding at the $8^{th}$ week, and the titers of antibodies against HPV16 and HPV35 in the serum were analyzed. The results of the analysis were shown in FIGS. 8A-8C. The results showed that the H16N30-35T4 VLP induced high titers of neutralizing antibodies against HPV16 in mice, and its protective effect was comparable to those of the HPV16N30 VLP alone and the mixed HPV16/HPV35 VLP at the same dose, and was significantly better than that of the HPV35 VLP alone at the same dose; and it induced high titers of neutralizing antibodies against HPV35 in mice, and its protective effect was comparable to those of the HPV35 VLP alone and the mixed HPV16/HPV35 VLP at the same dose, and was significantly better than that of the HPV16N30 VLP alone at the same dose. This indicated that the H16N30-35T4 VLP had good cross-immunogenicity and cross-protection against HPV16 and HPV35.

TABLE 15

Immunization protocols

| Group | | Immunization antigen | Adjuvant | Immunization dose | Number | Immunization protocol (week) |
|---|---|---|---|---|---|---|
| 10 µg dose group | | HPV16N30 VLP | Aluminum adjuvant | 10 µg | 6 | 0, 2, 4 |
| | | HPV35 VLP | Aluminum adjuvant | 10 µg | 6 | 0, 2, 4 |
| | | HPV16/HPV35 VLP | Aluminum adjuvant | 10 µg for each VLP | 6 | 0, 2, 4 |
| | | H16N30-35T4 VLP | Aluminum adjuvant | 10 µg | 6 | 0, 2, 4 |
| 1 µg dose group | | HPV16N30 VLP | Aluminum adjuvant | 1 µg | 6 | 0, 2, 4 |
| | | HPV35 VLP | Aluminum adjuvant | 1 µg | 6 | 0, 2, 4 |
| | | HPV16/HPV35 VLP | Aluminum adjuvant | 1 µg for each VLP | 6 | 0, 2, 4 |
| | | H16N30-35T4 VLP | Aluminum adjuvant | 1 µg | 6 | 0, 2, 4 |
| 0.1 µg dose group | | HPV16N30 VLP | Aluminum adjuvant | 0.1 µg | 6 | 0, 2, 4 |
| | | HPV35 VLP | Aluminum adjuvant | 0.1 µg | 6 | 0, 2, 4 |
| | | HPV16/HPV35 VLP | Aluminum adjuvant | 0.1 µg for each VLP | 6 | 0, 2, 4 |
| | | H16N30-35T4 VLP | Aluminum adjuvant | 0.1 µg | 6 | 0, 2, 4 |

Evaluation of Titers of Neutralizing Antibodies in Serum After Immunization with H16N30-35T4-31S3 VLP in Mice In this experiment, the immunization protocols were shown in Table 16. All mice (6-weeks old BalB/c female mice) were divided into 3 groups: 10 µg dose group (immunization dose was 10 µg, using aluminum adjuvant), 1 µg dose group (immunization dose was 1 µg, using aluminum adjuvant), and 0.1 µg dose group (immunization dose was 0.1 µg, using aluminum adjuvant). Each group was subdivided into 6 subgroups, in which the control subgroups 1, 2, and 3 were immunized with the HPV16N30 VLP alone, the HPV35 VLP alone and the HPV31 VLP alone, respectively, the control subgroup 4 was immunized with the mixed HPV16/HPV35/HPV31 VLP, and the experimental subgroup was immunized with H16N30-35T4-31S3 VLP alone.

Figure 8D:
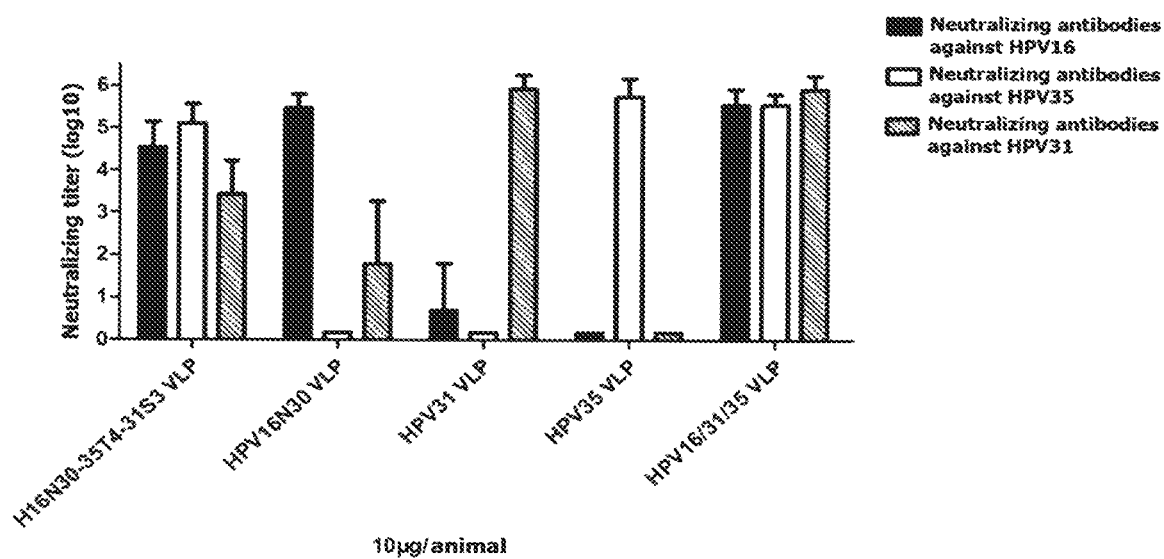
FIGS. 8D-8F show the evaluation results of neutralizing antibody titers in mouse serum after immunization of mice with H16N30-35T4-31S3 VLP.
Figure 8E:
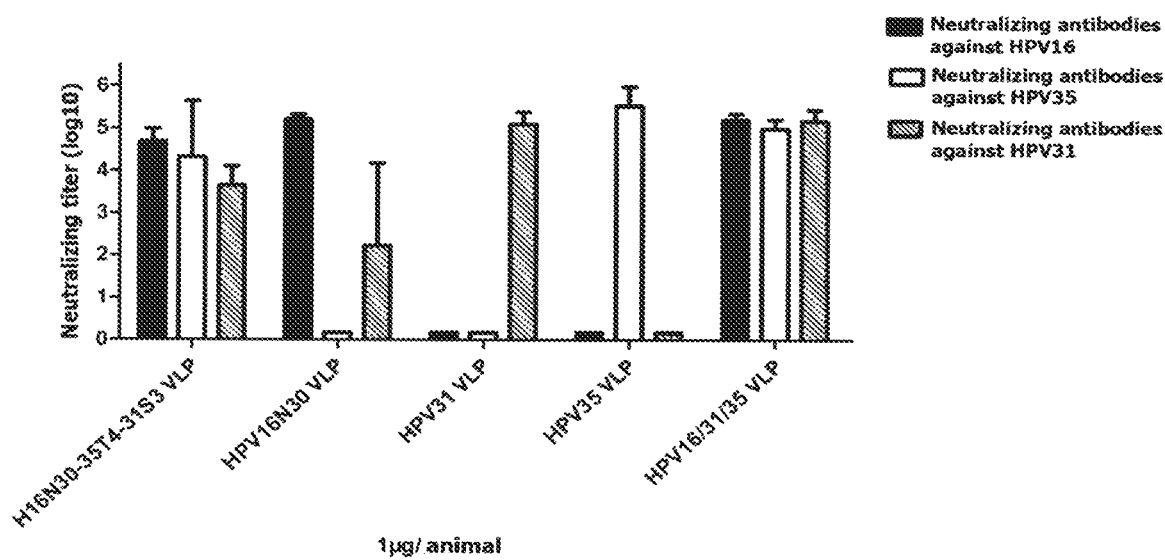
Figure 8F:
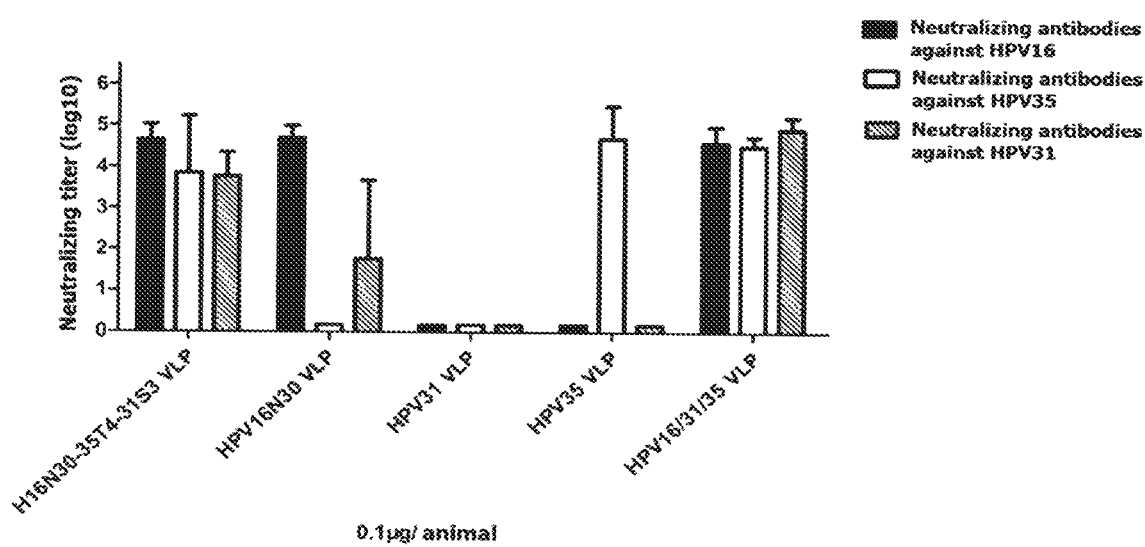

Six mice per subgroup were immunized by intraperitoneal injection, and the immunization doses were 10 µg, 1 µg, 0.1 µg, and the injection volume was 1 ml. All mice were immunized initially at the $0^{th}$ week, and boosted at the $2^{nd}$ and $4^{th}$ weeks, respectively. Blood samples were collected from the mice via orbital bleeding at the $8^{th}$ week, and the titers of antibodies against HPV16, HPV35 and HPV31 in the serum were analyzed. The results of the analysis were shown in FIGS. 8D-8F. The results showed that the H16N30-35T4-31S3 VLP induced high titers of neutralizing antibodies against HPV16 in mice, and its protective effect was comparable to those of the HPV16N30 VLP alone and the mixed HPV16/HPV35/HPV31 VLP at the same dose, and was significantly better than that of the HPV35 VLP alone or the HPV31 VLP alone at the same dose; and it induced high titers of neutralizing antibodies against HPV35 in mice, and its protective effect was comparable to those of the HPV35 VLP alone and the mixed HPV16/HPV35/HPV31 VLP at the same dose, and was significantly better than that of the HPV16N30 VLP alone or the HPV31 VLP alone at the same dose; and it induced high titers of neutralizing antibodies against HPV31 in mice, and its protection effect was comparable to those of the HPV31 VLP alone and the mixed HPV16/HPV35/HPV31 VLP at the same dose, and significantly better than that of the HPV16N30 VLP alone or the HPV35 VLP alone at the same dose. This indicated that the H16N30-35T4-31S3 VLP had good cross-immunogenicity and cross-protection against HPV16, HPV35 and HPV31.

TABLE 16

Immunization protocols

| Group | | Immunization antigen | Adjuvant | Immunization dose | Number | Immunization protocol (week) |
|---|---|---|---|---|---|---|
| 10 µg dose group | | HPV16N30 VLP | aluminum adjuvant | 10 µg | 6 | 0, 2, 4 |
| | | HPV35 VLP | aluminum adjuvant | 10 µg | 6 | 0, 2, 4 |
| | | HPV31 VLP | aluminum adjuvant | 10 µg | 6 | 0, 2, 4 |
| | | HPV16/HPV35/HPV31 VLP | aluminum adjuvant | 10 µg for each VLP | 6 | 0, 2, 4 |
| | | H16N30-35T4-31S3 VLP | aluminum adjuvant | 10 µg | 6 | 0, 2, 4 |

TABLE 16-continued

Immunization protocols

| Group | Immunization antigen | Adjuvant | Immunization dose | Number | Immunization protocol (week) |
|---|---|---|---|---|---|
| 1 µg dose group | HPV16N30 VLP | aluminum adjuvant | 1 µg | 6 | 0, 2, 4 |
| | HPV35 VLP | aluminum adjuvant | 1 µg | 6 | 0, 2, 4 |
| | HPV31 VLP | aluminum adjuvant | 1 µg | 6 | 0, 2, 4 |
| | HPV16/HPV35/HPV31 VLP | aluminum adjuvant | 1 µg for each VLP | 6 | 0, 2, 4 |
| | H16N30-35T4-31S3 VLP | aluminum adjuvant | 1 µg | 6 | 0, 2, 4 |
| 0.1 µg dose group | HPV16N30 VLP | aluminum adjuvant | 0.1 µg | 6 | 0, 2, 4 |
| | HPV35 VLP | aluminum adjuvant | 0.1 µg | 6 | 0, 2, 4 |
| | HPV31 VLP | aluminum adjuvant | 0.1 µg | 6 | 0, 2, 4 |
| | HPV16/HPV35/HPV31 VLP | aluminum adjuvant | 0.1 µg for each VLP | 6 | 0, 2, 4 |
| | H16N30-35T4-31S3 VLP | aluminum adjuvant | 0.1 µg | 6 | 0, 2, 4 |

Although specific embodiments of the invention have been described in detail, a person skilled in the art will appreciate that various modifications and alterations of the details of the invention can be made in light of the teachings of all disclosures, and all these modifications and alterations fall within the scope of the invention. The full scope of the invention is given by the appended claims and any equivalents thereof.

What is claimed is:

1. A mutated HPV16 L1 protein or a variant thereof, wherein the mutated HPV16 L1 protein has the following mutations compared to a wild-type HPV16 L1 protein:
   (1) a N-terminal truncation of 4-50 amino acids; and
   (2) a substitution of amino acid residues at positions 292-316 of the wild-type HPV16 L1 protein with amino acid residues at the corresponding positions of a L1 protein of a second type of wild-type HPV;

optionally, the mutated HPV16 L1 protein further has the following mutation:

(3) a substitution of amino acid residues at positions 76-87 of the wild-type HPV16 L1 protein with amino acid residues at the corresponding positions of a L1 protein of a third type of wild-type HPV;

(4) a substitution of amino acid residues at positions 152-167 of the wild-type HPV16 L1 protein with amino acid residues at the corresponding positions of a L1 protein of a third type of wild-type HPV; or, (5) a substitution of amino acid residues at positions 202-207 of the wild-type HPV16 L1 protein with amino acid residues at the corresponding positions of a L1 protein of a third type of wild-type HPV;

and, the variant differs from the mutated HPV16 L1 protein only by substitution, addition or deletion of 1, 2, 3, 4, 5, 6, 7, 8, or 9 amino acids, and maintains the function of the mutated HPV16 L1 protein, including an ability of inducing neutralizing antibodies against at least two types of HPV.

2. An isolated nucleic acid, which encodes the mutated HPV16 L1 protein or variant thereof according to claim 1.

3. A vector comprising the isolated nucleic acid according to claim 2.

4. A host cell comprising the isolated nucleic acid according to claim 2 and/or a vector comprising the isolated nucleic acid.

5. A HPV virus-like particle, which comprises or consists of the mutated HPV16 L1 protein or variant thereof according to claim 1.

6. A composition, which comprises:

(i) the mutated HPV16 L1 protein or a variant thereof according to claim 1, or (ii) an isolated nucleic acid encoding the mutated HPV16 L1 protein or variant thereof as described in (i), or (iii) a vector comprising the isolated nucleic acid as described in (ii), or (iv) a host cell comprising the isolated nucleic acid as described in (ii) or the vector as described in (iii), or (v) a HPV virus-like particle comprising or consisting of the mutated HPV16 L1 protein or variant thereof as described in (i).

7. A pharmaceutical composition or vaccine, which comprises the HPV virus-like particle according to claim 5, and optionally further comprises a pharmaceutically acceptable carrier and/or excipient.

8. A method for preparing the mutated HPV16 L1 protein or variant thereof according to claim 1, which comprises expressing the mutated HPV16 L1 protein or variant thereof in a host cell, and then recovering the mutated HPV16 L1 protein or a variant thereof from a culture of the host cell.

9. A method for preparing a vaccine, which comprises combining the HPV virus-like particle according to claim 5 with a pharmaceutically acceptable carrier and/or excipient.

10. A method for preventing HPV infection or a disease caused by HPV infection, which comprises administering to a subject a prophylactically effective amount of the HPV virus-like particle according to claim 5 or a pharmaceutical composition or vaccine comprising the HPV virus-like particle and optionally a pharmaceutically acceptable carrier and/or excipient.

11. The mutated HPV16 L1 protein or variant thereof according to claim 1, wherein the mutated HPV16 L1 protein is characterized by one or more of the following items:

(i) the mutated HPV16 L1 protein has a N-terminal truncation of 4, 6, 8, 10, 20, 30 or 40 amino acids compared with a wild-type HPV16 L1 protein;

(ii) the second type of wild-type HPV is HPV35;

(iii) the third type of wild-type HPV is HPV31;

(iv) the amino acid residues at the corresponding positions described in (2) are the amino acid residues at positions 266-288 of the wild-type HPV35 L1 protein;

(v) the amino acid residues at the corresponding positions described in (3) are the amino acid residues at positions 50-62 of the wild-type HPV31 L1 protein;

(vi) the amino acid residues at the corresponding positions described in (4) are the amino acid residues at positions 127-142 of the wild-type HPV31 L1 protein;

(vii) the amino acid residues at the corresponding positions described in (5) are the amino acid residues at positions 177-182 of the wild-type HPV31 L1 protein;

(viii) the wild-type HPV16 L1 protein has an amino acid sequence set forth in SEQ ID NO: 1;

(ix) the wild-type HPV35 L1 protein has an amino acid sequence set forth in SEQ ID NO: 2; and (x) the wild-type HPV31 L1 protein has an amino acid sequence set forth in SEQ ID NO: 3.

12. The mutated HPV16 L1 protein or variant thereof according to claim 1, wherein the mutated HPV16 L1 protein has an amino acid sequence selected from the group consisting of SEQ ID NOs: 7, 9, 10, and 11.

13. The pharmaceutical composition or vaccine according to claim 7, wherein the HPV virus-like particle is present in an amount effective for preventing HPV infection or a disease caused by HPV infection.

14. The pharmaceutical composition or vaccine according to claim 13, wherein: the HPV infection is infection by one or more HPV types; and/or, the disease caused by HPV infection is selected from the group consisting of a cervical cancer and a condyloma acuminatum.

15. The pharmaceutical composition or vaccine according to claim 13, wherein the HPV infection is one or more selected from the group consisting of the following: HPV 16 infection, HPV 35 infection, and HPV 31 infection.

16. The method according to claim 8, wherein the host cell is *E. coli*.

17. The method according to claim 8, wherein the method comprises: expressing the mutated HPV16 L1 protein or a variant thereof in *E. coli*, and then obtaining the mutated HPV16 L1 protein or a variant thereof by purifying a lysate supernatant of the *E. coli*.

18. The method according to claim 10, wherein: the HPV infection is infection by one or more HPV types; and/or, the disease caused by HPV infection is selected from the group consisting of cervical cancer and condyloma acuminatum.

19. The method according to claim 10, wherein the HPV infection is one or more selected from the group consisting of the following: HPV 16 infection, HPV 35 infection, and HPV 31 infection.

* * * * *

SEQUENCE LISTING

<160> NUMBER OF SEQ ID NOS: 60

<210> SEQ ID NO 1
<211> LENGTH: 531
<212> TYPE: PRT
<213> ORGANISM: Human papillomavirus type 16

<400> SEQUENCE: 1

Met Gln Val Thr Phe Ile Tyr Ile Leu Val Ile Thr Cys Tyr Glu Asn
1               5                   10                  15

Asp Val Asn Val Tyr His Ile Phe Phe Gln Met Ser Leu Trp Leu Pro
            20                  25                  30

Ser Glu Ala Thr Val Tyr Leu Pro Pro Val Pro Val Ser Lys Val Val
        35                  40                  45

Ser Thr Asp Glu Tyr Val Ala Arg Thr Asn Ile Tyr Tyr His Ala Gly
    50                  55                  60

Thr Ser Arg Leu Leu Ala Val Gly His Pro Tyr Phe Pro Ile Lys Lys
65                  70                  75                  80

Pro Asn Asn Asn Lys Ile Leu Val Pro Lys Val Ser Gly Leu Gln Tyr
                85                  90                  95

Arg Val Phe Arg Ile His Leu Pro Asp Pro Asn Lys Phe Gly Phe Pro
            100                 105                 110

Asp Thr Ser Phe Tyr Asn Pro Asp Thr Gln Arg Leu Val Trp Ala Cys
        115                 120                 125

Val Gly Val Glu Val Gly Arg Gly Gln Pro Leu Gly Val Gly Ile Ser
    130                 135                 140

Gly His Pro Leu Leu Asn Lys Leu Asp Asp Thr Glu Asn Ala Ser Ala
145                 150                 155                 160

Tyr Ala Ala Asn Ala Gly Val Asp Asn Arg Glu Cys Ile Ser Met Asp
                165                 170                 175

```
Tyr Lys Gln Thr Gln Leu Cys Leu Ile Gly Cys Lys Pro Pro Ile Gly
            180                 185                 190

Glu His Trp Gly Lys Gly Ser Pro Cys Thr Asn Val Ala Val Asn Pro
        195                 200                 205

Gly Asp Cys Pro Pro Leu Glu Leu Ile Asn Thr Val Ile Gln Asp Gly
    210                 215                 220

Asp Met Val Asp Thr Gly Phe Gly Ala Met Asp Phe Thr Thr Leu Gln
225                 230                 235                 240

Ala Asn Lys Ser Glu Val Pro Leu Asp Ile Cys Thr Ser Ile Cys Lys
                245                 250                 255

Tyr Pro Asp Tyr Ile Lys Met Val Ser Glu Pro Tyr Gly Asp Ser Leu
            260                 265                 270

Phe Phe Tyr Leu Arg Arg Glu Gln Met Phe Val Arg His Leu Phe Asn
        275                 280                 285

Arg Ala Gly Ala Val Gly Asp Asn Val Pro Asp Asp Leu Tyr Ile Lys
    290                 295                 300

Gly Ser Gly Ser Thr Ala Asn Leu Ala Ser Ser Asn Tyr Phe Pro Thr
305                 310                 315                 320

Pro Ser Gly Ser Met Val Thr Ser Asp Ala Gln Ile Phe Asn Lys Pro
                325                 330                 335

Tyr Trp Leu Gln Arg Ala Gln Gly His Asn Asn Gly Ile Cys Trp Gly
            340                 345                 350

Asn Gln Leu Phe Val Thr Val Val Asp Thr Thr Arg Ser Thr Asn Met
        355                 360                 365

Ser Leu Cys Ala Ala Ile Ser Thr Ser Glu Thr Thr Tyr Lys Asn Thr
    370                 375                 380

Asn Phe Lys Glu Tyr Leu Arg His Gly Glu Glu Tyr Asp Leu Gln Phe
385                 390                 395                 400

Ile Phe Gln Leu Cys Lys Ile Thr Leu Thr Ala Asp Ile Met Thr Tyr
                405                 410                 415

Ile His Ser Met Asn Ser Thr Ile Leu Glu Asp Trp Asn Phe Gly Leu
            420                 425                 430

Gln Pro Pro Pro Gly Gly Thr Leu Glu Asp Thr Tyr Arg Phe Val Thr
        435                 440                 445

Ser Gln Ala Ile Ala Cys Gln Lys His Thr Pro Pro Ala Pro Lys Glu
    450                 455                 460

Asp Pro Leu Lys Lys Tyr Thr Phe Trp Glu Val Asn Leu Lys Glu Lys
465                 470                 475                 480

Phe Ser Ala Asp Leu Asp Gln Phe Pro Leu Gly Arg Lys Phe Leu Leu
                485                 490                 495

Gln Ala Gly Leu Glu Ala Lys Pro Lys Phe Thr Leu Gly Lys Arg Lys
            500                 505                 510

Ala Thr Pro Thr Thr Ser Ser Thr Ser Thr Thr Ala Lys Arg Lys Lys
        515                 520                 525

Arg Lys Leu
    530

<210> SEQ ID NO 2
<211> LENGTH: 502
<212> TYPE: PRT
<213> ORGANISM: Human papillomavirus type 35

<400> SEQUENCE: 2

Met Ser Leu Trp Arg Ser Asn Glu Ala Thr Val Tyr Leu Pro Pro Val
1               5                   10                  15
```

```
Ser Val Ser Lys Val Val Ser Thr Asp Glu Tyr Val Thr Arg Thr Asn
            20                  25                  30

Ile Tyr Tyr His Ala Gly Ser Ser Arg Leu Leu Ala Val Gly His Pro
            35                  40                  45

Tyr Tyr Ala Ile Lys Lys Gln Asp Ser Asn Lys Ile Ala Val Pro Lys
        50                  55                  60

Val Ser Gly Leu Gln Tyr Arg Val Phe Arg Val Lys Leu Pro Asp Pro
65                  70                  75                  80

Asn Lys Phe Gly Phe Pro Asp Thr Ser Phe Tyr Asp Pro Ala Ser Gln
                85                  90                  95

Arg Leu Val Trp Ala Cys Thr Gly Val Glu Val Gly Arg Gly Gln Pro
                100                 105                 110

Leu Gly Val Gly Ile Ser Gly His Pro Leu Leu Asn Lys Leu Asp Asp
            115                 120                 125

Thr Glu Asn Ser Asn Lys Tyr Val Gly Asn Ser Gly Thr Asp Asn Arg
130                 135                 140

Glu Cys Ile Ser Met Asp Tyr Lys Gln Thr Gln Leu Cys Leu Ile Gly
145                 150                 155                 160

Cys Arg Pro Pro Ile Gly Glu His Trp Gly Lys Gly Thr Pro Cys Asn
                165                 170                 175

Ala Asn Gln Val Lys Ala Gly Glu Cys Pro Pro Leu Glu Leu Leu Asn
            180                 185                 190

Thr Val Leu Gln Asp Gly Asp Met Val Asp Thr Gly Phe Gly Ala Met
        195                 200                 205

Asp Phe Thr Thr Leu Gln Ala Asn Lys Ser Asp Val Pro Leu Asp Ile
        210                 215                 220

Cys Ser Ser Ile Cys Lys Tyr Pro Asp Tyr Leu Lys Met Val Ser Glu
225                 230                 235                 240

Pro Tyr Gly Asp Met Leu Phe Phe Tyr Leu Arg Arg Glu Gln Met Phe
                245                 250                 255

Val Arg His Leu Phe Asn Arg Ala Gly Thr Val Gly Glu Thr Val Pro
            260                 265                 270

Ala Asp Leu Tyr Ile Lys Gly Thr Thr Gly Thr Leu Pro Ser Thr Ser
        275                 280                 285

Tyr Phe Pro Thr Pro Ser Gly Ser Met Val Thr Ser Asp Ala Gln Ile
    290                 295                 300

Phe Asn Lys Pro Tyr Trp Leu Gln Arg Ala Gln Gly His Asn Asn Gly
305                 310                 315                 320

Ile Cys Trp Ser Asn Gln Leu Phe Val Thr Val Val Asp Thr Thr Arg
                325                 330                 335

Ser Thr Asn Met Ser Val Cys Ser Ala Val Ser Ser Ser Asp Ser Thr
            340                 345                 350

Tyr Lys Asn Asp Asn Phe Lys Glu Tyr Leu Arg His Gly Glu Glu Tyr
        355                 360                 365

Asp Leu Gln Phe Ile Phe Gln Leu Cys Lys Ile Thr Leu Thr Ala Asp
        370                 375                 380

Val Met Thr Tyr Ile His Ser Met Asn Pro Ser Ile Leu Glu Asp Trp
385                 390                 395                 400

Asn Phe Gly Leu Thr Pro Pro Ser Gly Thr Leu Glu Asp Thr Tyr
                405                 410                 415

Arg Tyr Val Thr Ser Gln Ala Val Thr Cys Gln Lys Pro Ser Ala Pro
        420                 425                 430
```

```
Lys Pro Lys Asp Asp Pro Leu Lys Asn Tyr Thr Phe Trp Glu Val Asp
            435                 440                 445

Leu Lys Glu Lys Phe Ser Ala Asp Leu Asp Gln Phe Pro Leu Gly Arg
450                 455                 460

Lys Phe Leu Leu Gln Ala Gly Leu Lys Ala Arg Pro Asn Phe Arg Leu
465                 470                 475                 480

Gly Lys Arg Ala Ala Pro Ala Ser Thr Ser Lys Lys Ser Ser Thr Lys
                485                 490                 495

Arg Arg Lys Val Lys Ser
            500

<210> SEQ ID NO 3
<211> LENGTH: 504
<212> TYPE: PRT
<213> ORGANISM: Human papillomavirus type 31

<400> SEQUENCE: 3

Met Ser Leu Trp Arg Pro Ser Glu Ala Thr Val Tyr Leu Pro Pro Val
1               5                   10                  15

Pro Val Ser Lys Val Val Ser Thr Asp Glu Tyr Val Thr Arg Thr Asn
            20                  25                  30

Ile Tyr Tyr His Ala Gly Ser Ala Arg Leu Leu Thr Val Gly His Pro
        35                  40                  45

Tyr Tyr Ser Ile Pro Lys Ser Asp Asn Pro Lys Lys Ile Val Val Pro
50                  55                  60

Lys Val Ser Gly Leu Gln Tyr Arg Val Phe Arg Val Arg Leu Pro Asp
65                  70                  75                  80

Pro Asn Lys Phe Gly Phe Pro Asp Thr Ser Phe Tyr Asn Pro Glu Thr
                85                  90                  95

Gln Arg Leu Val Trp Ala Cys Val Gly Leu Glu Val Gly Arg Gly Gln
            100                 105                 110

Pro Leu Gly Val Gly Ile Ser Gly His Pro Leu Leu Asn Lys Phe Asp
        115                 120                 125

Asp Thr Glu Asn Ser Asn Arg Tyr Ala Gly Gly Pro Gly Thr Asp Asn
130                 135                 140

Arg Glu Cys Ile Ser Met Asp Tyr Lys Gln Thr Gln Leu Cys Leu Leu
145                 150                 155                 160

Gly Cys Lys Pro Pro Ile Gly Glu His Trp Gly Lys Gly Ser Pro Cys
                165                 170                 175

Ser Asn Asn Ala Ile Thr Pro Gly Asp Cys Pro Pro Leu Glu Leu Lys
            180                 185                 190

Asn Ser Val Ile Gln Asp Gly Asp Met Val Asp Thr Gly Phe Gly Ala
        195                 200                 205

Met Asp Phe Thr Ala Leu Gln Asp Thr Lys Ser Asn Val Pro Leu Asp
210                 215                 220

Ile Cys Asn Ser Ile Cys Lys Tyr Pro Asp Tyr Leu Lys Met Val Ala
225                 230                 235                 240

Glu Pro Tyr Gly Asp Thr Leu Phe Phe Tyr Leu Arg Arg Glu Gln Met
                245                 250                 255

Phe Val Arg His Phe Phe Asn Arg Ser Gly Thr Val Gly Glu Ser Val
            260                 265                 270

Pro Thr Asp Leu Tyr Ile Lys Gly Ser Gly Ser Thr Ala Thr Leu Ala
        275                 280                 285

Asn Ser Thr Tyr Phe Pro Thr Pro Ser Gly Ser Met Val Thr Ser Asp
290                 295                 300
```

```
Ala Gln Ile Phe Asn Lys Pro Tyr Trp Met Gln Arg Ala Gln Gly His
305                 310                 315                 320

Asn Asn Gly Ile Cys Trp Gly Asn Gln Leu Phe Val Thr Val Val Asp
                325                 330                 335

Thr Thr Arg Ser Thr Asn Met Ser Val Cys Ala Ala Ile Ala Asn Ser
            340                 345                 350

Asp Thr Thr Phe Lys Ser Ser Asn Phe Lys Glu Tyr Leu Arg His Gly
        355                 360                 365

Glu Glu Phe Asp Leu Gln Phe Ile Phe Gln Leu Cys Lys Ile Thr Leu
    370                 375                 380

Ser Ala Asp Ile Met Thr Tyr Ile His Ser Met Asn Pro Ala Ile Leu
385                 390                 395                 400

Glu Asp Trp Asn Phe Gly Leu Thr Thr Pro Pro Ser Gly Ser Leu Glu
                405                 410                 415

Asp Thr Tyr Arg Phe Val Thr Ser Gln Ala Ile Thr Cys Gln Lys Thr
            420                 425                 430

Ala Pro Gln Lys Pro Lys Glu Asp Pro Phe Lys Asp Tyr Val Phe Trp
        435                 440                 445

Glu Val Asn Leu Lys Glu Lys Phe Ser Ala Asp Leu Asp Gln Phe Pro
    450                 455                 460

Leu Gly Arg Lys Phe Leu Leu Gln Ala Gly Tyr Arg Ala Arg Pro Lys
465                 470                 475                 480

Phe Lys Ala Gly Lys Arg Ser Ala Pro Ser Ala Ser Thr Thr Thr Pro
                485                 490                 495

Ala Lys Arg Lys Lys Thr Lys Lys
            500

<210> SEQ ID NO 4
<211> LENGTH: 502
<212> TYPE: PRT
<213> ORGANISM: Artificial Sequence
<220> FEATURE:
<223> OTHER INFORMATION: H16N30-35T1

<400> SEQUENCE: 4

Met Leu Pro Ser Glu Ala Thr Val Tyr Leu Pro Pro Val Pro Val Ser
1               5                   10                  15

Lys Val Val Ser Thr Asp Glu Tyr Val Ala Arg Thr Asn Ile Tyr Tyr
            20                  25                  30

His Ala Gly Thr Ser Arg Leu Leu Ala Val Gly His Pro Tyr Tyr Ala
        35                  40                  45

Ile Lys Lys Gln Asp Ser Asn Lys Ile Ala Val Pro Lys Val Ser Gly
    50                  55                  60

Leu Gln Tyr Arg Val Phe Arg Ile His Leu Pro Asp Pro Asn Lys Phe
65                  70                  75                  80

Gly Phe Pro Asp Thr Ser Phe Tyr Asn Pro Asp Thr Gln Arg Leu Val
                85                  90                  95

Trp Ala Cys Val Gly Val Glu Val Gly Arg Gly Gln Pro Leu Gly Val
            100                 105                 110

Gly Ile Ser Gly His Pro Leu Leu Asn Lys Leu Asp Asp Thr Glu Asn
        115                 120                 125

Ala Ser Ala Tyr Ala Ala Asn Ala Gly Val Asp Asn Arg Glu Cys Ile
    130                 135                 140

Ser Met Asp Tyr Lys Gln Thr Gln Leu Cys Leu Ile Gly Cys Lys Pro
145                 150                 155                 160
```

Pro Ile Gly Glu His Trp Lys Gly Ser Pro Cys Thr Asn Val Ala
        165                 170                 175

Val Asn Pro Gly Asp Cys Pro Leu Glu Leu Ile Asn Thr Val Ile
        180                 185                 190

Gln Asp Gly Asp Met Val Asp Thr Gly Phe Gly Ala Met Asp Phe Thr
        195                 200                 205

Thr Leu Gln Ala Asn Lys Ser Glu Val Pro Leu Asp Ile Cys Thr Ser
    210                 215                 220

Ile Cys Lys Tyr Pro Asp Tyr Ile Lys Met Val Ser Glu Pro Tyr Gly
225                 230                 235                 240

Asp Ser Leu Phe Phe Tyr Leu Arg Arg Glu Gln Met Phe Val Arg His
                245                 250                 255

Leu Phe Asn Arg Ala Gly Ala Val Gly Asp Asn Val Pro Asp Asp Leu
            260                 265                 270

Tyr Ile Lys Gly Ser Gly Ser Thr Ala Asn Leu Ala Ser Ser Asn Tyr
        275                 280                 285

Phe Pro Thr Pro Ser Gly Ser Met Val Thr Ser Asp Ala Gln Ile Phe
    290                 295                 300

Asn Lys Pro Tyr Trp Leu Gln Arg Ala Gln Gly His Asn Asn Gly Ile
305                 310                 315                 320

Cys Trp Gly Asn Gln Leu Phe Val Thr Val Val Asp Thr Thr Arg Ser
                325                 330                 335

Thr Asn Met Ser Leu Cys Ala Ala Ile Ser Thr Ser Glu Thr Thr Tyr
            340                 345                 350

Lys Asn Thr Asn Phe Lys Glu Tyr Leu Arg His Gly Glu Glu Tyr Asp
        355                 360                 365

Leu Gln Phe Ile Phe Gln Leu Cys Lys Ile Thr Leu Thr Ala Asp Ile
    370                 375                 380

Met Thr Tyr Ile His Ser Met Asn Ser Thr Ile Leu Glu Asp Trp Asn
385                 390                 395                 400

Phe Gly Leu Gln Pro Pro Pro Gly Gly Thr Leu Glu Asp Thr Tyr Arg
                405                 410                 415

Phe Val Thr Ser Gln Ala Ile Ala Cys Gln Lys His Thr Pro Pro Ala
            420                 425                 430

Pro Lys Glu Asp Pro Leu Lys Lys Tyr Thr Phe Trp Glu Val Asn Leu
        435                 440                 445

Lys Glu Lys Phe Ser Ala Asp Leu Asp Gln Phe Pro Leu Gly Arg Lys
    450                 455                 460

Phe Leu Leu Gln Ala Gly Leu Glu Ala Lys Pro Lys Phe Thr Leu Gly
465                 470                 475                 480

Lys Arg Lys Ala Thr Pro Thr Thr Ser Ser Thr Ser Thr Thr Ala Lys
                485                 490                 495

Arg Lys Lys Arg Lys Leu
            500

<210> SEQ ID NO 5
<211> LENGTH: 502
<212> TYPE: PRT
<213> ORGANISM: Artificial Sequence
<220> FEATURE:
<223> OTHER INFORMATION: H16N30-35T2

<400> SEQUENCE: 5

Met Leu Pro Ser Glu Ala Thr Val Tyr Leu Pro Pro Val Pro Val Ser
1               5                   10                  15

```
Lys Val Val Ser Thr Asp Glu Tyr Val Ala Arg Thr Asn Ile Tyr Tyr
            20                  25                  30

His Ala Gly Thr Ser Arg Leu Leu Ala Val Gly His Pro Tyr Phe Pro
            35                  40                  45

Ile Lys Lys Pro Asn Asn Asn Lys Ile Leu Val Pro Lys Val Ser Gly
50                  55                  60

Leu Gln Tyr Arg Val Phe Arg Ile His Leu Pro Asp Pro Asn Lys Phe
65                  70                  75                  80

Gly Phe Pro Asp Thr Ser Phe Tyr Asn Pro Asp Thr Gln Arg Leu Val
                85                  90                  95

Trp Ala Cys Val Gly Val Glu Val Gly Arg Gly Gln Pro Leu Gly Val
            100                 105                 110

Gly Ile Ser Gly His Pro Leu Leu Asn Lys Leu Asp Asp Thr Glu Asn
            115                 120                 125

Ser Asn Lys Tyr Val Gly Asn Ser Gly Thr Asp Asn Arg Glu Cys Ile
            130                 135                 140

Ser Met Asp Tyr Lys Gln Thr Gln Leu Cys Leu Ile Gly Cys Lys Pro
145                 150                 155                 160

Pro Ile Gly Glu His Trp Gly Lys Gly Ser Pro Cys Thr Asn Val Ala
                165                 170                 175

Val Asn Pro Gly Asp Cys Pro Pro Leu Glu Leu Ile Asn Thr Val Ile
            180                 185                 190

Gln Asp Gly Asp Met Val Asp Thr Gly Phe Gly Ala Met Asp Phe Thr
            195                 200                 205

Thr Leu Gln Ala Asn Lys Ser Glu Val Pro Leu Asp Ile Cys Thr Ser
            210                 215                 220

Ile Cys Lys Tyr Pro Asp Tyr Ile Lys Met Val Ser Glu Pro Tyr Gly
225                 230                 235                 240

Asp Ser Leu Phe Phe Tyr Leu Arg Arg Glu Gln Met Phe Val Arg His
                245                 250                 255

Leu Phe Asn Arg Ala Gly Ala Val Gly Asp Asn Val Pro Asp Asp Leu
            260                 265                 270

Tyr Ile Lys Gly Ser Gly Ser Thr Ala Asn Leu Ala Ser Ser Asn Tyr
            275                 280                 285

Phe Pro Thr Pro Ser Gly Ser Met Val Thr Ser Asp Ala Gln Ile Phe
            290                 295                 300

Asn Lys Pro Tyr Trp Leu Gln Arg Ala Gln Gly His Asn Asn Gly Ile
305                 310                 315                 320

Cys Trp Gly Asn Gln Leu Phe Val Thr Val Val Asp Thr Thr Arg Ser
                325                 330                 335

Thr Asn Met Ser Leu Cys Ala Ala Ile Ser Thr Ser Glu Thr Thr Tyr
            340                 345                 350

Lys Asn Thr Asn Phe Lys Glu Tyr Leu Arg His Gly Glu Glu Tyr Asp
            355                 360                 365

Leu Gln Phe Ile Phe Gln Leu Cys Lys Ile Thr Leu Thr Ala Asp Ile
            370                 375                 380

Met Thr Tyr Ile His Ser Met Asn Ser Thr Ile Leu Glu Asp Trp Asn
385                 390                 395                 400

Phe Gly Leu Gln Pro Pro Pro Gly Gly Thr Leu Glu Asp Thr Tyr Arg
                405                 410                 415

Phe Val Thr Ser Gln Ala Ile Ala Cys Gln Lys His Thr Pro Pro Ala
            420                 425                 430
```

```
Pro Lys Glu Asp Pro Leu Lys Lys Tyr Thr Phe Trp Glu Val Asn Leu
            435                 440                 445

Lys Glu Lys Phe Ser Ala Asp Leu Asp Gln Phe Pro Leu Gly Arg Lys
450                 455                 460

Phe Leu Leu Gln Ala Gly Leu Glu Ala Lys Pro Lys Phe Thr Leu Gly
465                 470                 475                 480

Lys Arg Lys Ala Thr Pro Thr Thr Ser Ser Thr Ser Thr Thr Ala Lys
                485                 490                 495

Arg Lys Lys Arg Lys Leu
                500

<210> SEQ ID NO 6
<211> LENGTH: 502
<212> TYPE: PRT
<213> ORGANISM: Artificial Sequence
<220> FEATURE:
<223> OTHER INFORMATION: H16N30-35T3

<400> SEQUENCE: 6

Met Leu Pro Ser Glu Ala Thr Val Tyr Leu Pro Val Pro Val Ser
1               5                   10                  15

Lys Val Val Ser Thr Asp Glu Tyr Val Ala Arg Thr Asn Ile Tyr Tyr
                20                  25                  30

His Ala Gly Thr Ser Arg Leu Leu Ala Val Gly His Pro Tyr Phe Pro
            35                  40                  45

Ile Lys Lys Pro Asn Asn Asn Lys Ile Leu Val Pro Lys Val Ser Gly
        50                  55                  60

Leu Gln Tyr Arg Val Phe Arg Ile His Leu Pro Asp Pro Asn Lys Phe
65                  70                  75                  80

Gly Phe Pro Asp Thr Ser Phe Tyr Asn Pro Asp Thr Gln Arg Leu Val
                85                  90                  95

Trp Ala Cys Val Gly Val Glu Val Gly Arg Gly Gln Pro Leu Gly Val
            100                 105                 110

Gly Ile Ser Gly His Pro Leu Leu Asn Lys Leu Asp Asp Thr Glu Asn
        115                 120                 125

Ala Ser Ala Tyr Ala Ala Asn Ala Gly Val Asp Asn Arg Glu Cys Ile
130                 135                 140

Ser Met Asp Tyr Lys Gln Thr Gln Leu Cys Leu Ile Gly Cys Lys Pro
145                 150                 155                 160

Pro Ile Gly Glu His Trp Gly Lys Gly Thr Pro Cys Asn Ala Asn Gln
                165                 170                 175

Val Lys Ala Gly Glu Cys Pro Pro Leu Glu Leu Ile Asn Thr Val Ile
            180                 185                 190

Gln Asp Gly Asp Met Val Asp Thr Gly Phe Gly Ala Met Asp Phe Thr
        195                 200                 205

Thr Leu Gln Ala Asn Lys Ser Glu Val Pro Leu Asp Ile Cys Thr Ser
210                 215                 220

Ile Cys Lys Tyr Pro Asp Tyr Ile Lys Met Val Ser Glu Pro Tyr Gly
225                 230                 235                 240

Asp Ser Leu Phe Phe Tyr Leu Arg Arg Glu Gln Met Phe Val Arg His
                245                 250                 255

Leu Phe Asn Arg Ala Gly Ala Val Gly Asp Asn Val Pro Asp Asp Leu
            260                 265                 270

Tyr Ile Lys Gly Ser Gly Ser Thr Ala Asn Leu Ala Ser Ser Asn Tyr
        275                 280                 285
```

```
Phe Pro Thr Pro Ser Gly Ser Met Val Thr Ser Asp Ala Gln Ile Phe
    290                 295                 300

Asn Lys Pro Tyr Trp Leu Gln Arg Ala Gln Gly His Asn Asn Gly Ile
305                 310                 315                 320

Cys Trp Gly Asn Gln Leu Phe Val Thr Val Val Asp Thr Thr Arg Ser
                325                 330                 335

Thr Asn Met Ser Leu Cys Ala Ala Ile Ser Thr Ser Glu Thr Thr Tyr
            340                 345                 350

Lys Asn Thr Asn Phe Lys Glu Tyr Leu Arg His Gly Glu Glu Tyr Asp
                355                 360                 365

Leu Gln Phe Ile Phe Gln Leu Cys Lys Ile Thr Leu Thr Ala Asp Ile
    370                 375                 380

Met Thr Tyr Ile His Ser Met Asn Ser Thr Ile Leu Glu Asp Trp Asn
385                 390                 395                 400

Phe Gly Leu Gln Pro Pro Gly Gly Thr Leu Glu Asp Thr Tyr Arg
                405                 410                 415

Phe Val Thr Ser Gln Ala Ile Ala Cys Gln Lys His Thr Pro Pro Ala
                420                 425                 430

Pro Lys Glu Asp Pro Leu Lys Lys Tyr Thr Phe Trp Glu Val Asn Leu
            435                 440                 445

Lys Glu Lys Phe Ser Ala Asp Leu Asp Gln Phe Pro Leu Gly Arg Lys
450                 455                 460

Phe Leu Leu Gln Ala Gly Leu Glu Ala Lys Pro Lys Phe Thr Leu Gly
465                 470                 475                 480

Lys Arg Lys Ala Thr Pro Thr Thr Ser Ser Thr Ser Thr Thr Ala Lys
                485                 490                 495

Arg Lys Lys Arg Lys Leu
                500

<210> SEQ ID NO 7
<211> LENGTH: 500
<212> TYPE: PRT
<213> ORGANISM: Artificial Sequence
<220> FEATURE:
<223> OTHER INFORMATION: H16N30-35T4

<400> SEQUENCE: 7

Met Leu Pro Ser Glu Ala Thr Val Tyr Leu Pro Pro Val Pro Val Ser
1               5                   10                  15

Lys Val Val Ser Thr Asp Glu Tyr Val Ala Arg Thr Asn Ile Tyr Tyr
                20                  25                  30

His Ala Gly Thr Ser Arg Leu Leu Ala Val Gly His Pro Tyr Phe Pro
            35                  40                  45

Ile Lys Lys Pro Asn Asn Asn Lys Ile Leu Val Pro Lys Val Ser Gly
        50                  55                  60

Leu Gln Tyr Arg Val Phe Arg Ile His Leu Pro Asp Pro Asn Lys Phe
65                  70                  75                  80

Gly Phe Pro Asp Thr Ser Phe Tyr Asn Pro Asp Thr Gln Arg Leu Val
                85                  90                  95

Trp Ala Cys Val Gly Val Glu Val Gly Arg Gly Gln Pro Leu Gly Val
            100                 105                 110

Gly Ile Ser Gly His Pro Leu Leu Asn Lys Leu Asp Asp Thr Glu Asn
        115                 120                 125

Ala Ser Ala Tyr Ala Ala Asn Ala Gly Val Asp Asn Arg Glu Cys Ile
    130                 135                 140
```

Ser Met Asp Tyr Lys Gln Thr Gln Leu Cys Leu Ile Gly Cys Lys Pro
145                 150                 155                 160

Pro Ile Gly Glu His Trp Gly Lys Gly Ser Pro Cys Thr Asn Val Ala
            165                 170                 175

Val Asn Pro Gly Asp Cys Pro Pro Leu Glu Leu Ile Asn Thr Val Ile
        180                 185                 190

Gln Asp Gly Asp Met Val Asp Thr Gly Phe Gly Ala Met Asp Phe Thr
    195                 200                 205

Thr Leu Gln Ala Asn Lys Ser Glu Val Pro Leu Asp Ile Cys Thr Ser
210                 215                 220

Ile Cys Lys Tyr Pro Asp Tyr Ile Lys Met Val Ser Glu Pro Tyr Gly
225                 230                 235                 240

Asp Ser Leu Phe Phe Tyr Leu Arg Arg Glu Gln Met Phe Val Arg His
            245                 250                 255

Leu Phe Asn Arg Ala Gly Thr Val Gly Glu Thr Val Pro Ala Asp Leu
        260                 265                 270

Tyr Ile Lys Gly Thr Thr Gly Thr Leu Pro Ser Thr Ser Tyr Phe Pro
    275                 280                 285

Thr Pro Ser Gly Ser Met Val Thr Ser Asp Ala Gln Ile Phe Asn Lys
290                 295                 300

Pro Tyr Trp Leu Gln Arg Ala Gln Gly His Asn Asn Gly Ile Cys Trp
305                 310                 315                 320

Ser Asn Gln Leu Phe Val Thr Val Val Asp Thr Thr Arg Ser Thr Asn
            325                 330                 335

Met Ser Leu Cys Ala Ala Ile Ser Thr Ser Glu Thr Thr Tyr Lys Asn
        340                 345                 350

Thr Asn Phe Lys Glu Tyr Leu Arg His Gly Glu Glu Tyr Asp Leu Gln
    355                 360                 365

Phe Ile Phe Gln Leu Cys Lys Ile Thr Leu Thr Ala Asp Ile Met Thr
370                 375                 380

Tyr Ile His Ser Met Asn Ser Thr Ile Leu Glu Asp Trp Asn Phe Gly
385                 390                 395                 400

Leu Gln Pro Pro Gly Gly Thr Leu Glu Asp Thr Tyr Arg Phe Val
            405                 410                 415

Thr Ser Gln Ala Ile Ala Cys Gln Lys His Thr Pro Pro Ala Pro Lys
        420                 425                 430

Glu Asp Pro Leu Lys Lys Tyr Thr Phe Trp Glu Val Asn Leu Lys Glu
    435                 440                 445

Lys Phe Ser Ala Asp Leu Asp Gln Phe Pro Leu Gly Arg Lys Phe Leu
450                 455                 460

Leu Gln Ala Gly Leu Glu Ala Lys Pro Lys Phe Thr Leu Gly Lys Arg
465                 470                 475                 480

Lys Ala Thr Pro Thr Thr Ser Ser Thr Ser Thr Thr Ala Lys Arg Lys
            485                 490                 495

Lys Arg Lys Leu
            500

<210> SEQ ID NO 8
<211> LENGTH: 502
<212> TYPE: PRT
<213> ORGANISM: Artificial Sequence
<220> FEATURE:
<223> OTHER INFORMATION: H16N30-35T5

<400> SEQUENCE: 8

```
Met Leu Pro Ser Glu Ala Thr Val Tyr Leu Pro Pro Val Pro Val Ser
1               5                   10                  15

Lys Val Val Ser Thr Asp Glu Tyr Val Ala Arg Thr Asn Ile Tyr Tyr
                20                  25                  30

His Ala Gly Thr Ser Arg Leu Leu Ala Val Gly His Pro Tyr Phe Pro
            35                  40                  45

Ile Lys Lys Pro Asn Asn Lys Ile Leu Val Pro Lys Val Ser Gly
    50                  55                  60

Leu Gln Tyr Arg Val Phe Arg Ile His Leu Pro Asp Pro Asn Lys Phe
65                  70                  75                  80

Gly Phe Pro Asp Thr Ser Phe Tyr Asn Pro Asp Thr Gln Arg Leu Val
                85                  90                  95

Trp Ala Cys Val Gly Val Glu Val Gly Arg Gly Gln Pro Leu Gly Val
                100                 105                 110

Gly Ile Ser Gly His Pro Leu Leu Asn Lys Leu Asp Asp Thr Glu Asn
                115                 120                 125

Ala Ser Ala Tyr Ala Ala Asn Ala Gly Val Asp Asn Arg Glu Cys Ile
            130                 135                 140

Ser Met Asp Tyr Lys Gln Thr Gln Leu Cys Leu Ile Gly Cys Lys Pro
145                 150                 155                 160

Pro Ile Gly Glu His Trp Gly Lys Gly Ser Pro Cys Thr Asn Val Ala
                165                 170                 175

Val Asn Pro Gly Asp Cys Pro Pro Leu Glu Leu Ile Asn Thr Val Ile
                180                 185                 190

Gln Asp Gly Asp Met Val Asp Thr Gly Phe Gly Ala Met Asp Phe Thr
            195                 200                 205

Thr Leu Gln Ala Asn Lys Ser Glu Val Pro Leu Asp Ile Cys Thr Ser
    210                 215                 220

Ile Cys Lys Tyr Pro Asp Tyr Ile Lys Met Val Ser Glu Pro Tyr Gly
225                 230                 235                 240

Asp Ser Leu Phe Phe Tyr Leu Arg Arg Glu Gln Met Phe Val Arg His
                245                 250                 255

Leu Phe Asn Arg Ala Gly Ala Val Gly Asp Asn Val Pro Asp Asp Leu
            260                 265                 270

Tyr Ile Lys Gly Ser Gly Ser Thr Ala Asn Leu Ala Ser Ser Asn Tyr
    275                 280                 285

Phe Pro Thr Pro Ser Gly Ser Met Val Thr Ser Asp Ala Gln Ile Phe
            290                 295                 300

Asn Lys Pro Tyr Trp Leu Gln Arg Ala Gln Gly His Asn Asn Gly Ile
305                 310                 315                 320

Cys Trp Ser Asn Gln Leu Phe Val Thr Val Val Asp Thr Thr Arg Ser
                325                 330                 335

Thr Asn Met Ser Leu Cys Ala Ala Val Ser Ser Ser Asp Ser Thr Tyr
            340                 345                 350

Lys Asn Asp Asn Phe Lys Glu Tyr Leu Arg His Gly Glu Glu Tyr Asp
            355                 360                 365

Leu Gln Phe Ile Phe Gln Leu Cys Lys Ile Thr Leu Thr Ala Asp Ile
    370                 375                 380

Met Thr Tyr Ile His Ser Met Asn Ser Thr Ile Leu Glu Asp Trp Asn
385                 390                 395                 400

Phe Gly Leu Gln Pro Pro Gly Gly Thr Leu Glu Asp Thr Tyr Arg
                405                 410                 415

Phe Val Thr Ser Gln Ala Ile Ala Cys Gln Lys His Thr Pro Pro Ala
```

```
                420             425             430
Pro Lys Glu Asp Pro Leu Lys Lys Tyr Thr Phe Trp Glu Val Asn Leu
            435                 440                 445

Lys Glu Lys Phe Ser Ala Asp Leu Asp Gln Phe Pro Leu Gly Arg Lys
        450                 455                 460

Phe Leu Leu Gln Ala Gly Leu Glu Ala Lys Pro Lys Phe Thr Leu Gly
465                 470                 475                 480

Lys Arg Lys Ala Thr Pro Thr Thr Ser Ser Thr Ser Thr Thr Ala Lys
            485                 490                 495

Arg Lys Lys Arg Lys Leu
            500

<210> SEQ ID NO 9
<211> LENGTH: 501
<212> TYPE: PRT
<213> ORGANISM: Artificial Sequence
<220> FEATURE:
<223> OTHER INFORMATION: H16N30-35T4-31S1

<400> SEQUENCE: 9

Met Leu Pro Ser Glu Ala Thr Val Tyr Leu Pro Pro Val Pro Val Ser
1               5                   10                  15

Lys Val Val Ser Thr Asp Glu Tyr Val Ala Arg Thr Asn Ile Tyr Tyr
            20                  25                  30

His Ala Gly Thr Ser Arg Leu Leu Ala Val Gly His Pro Tyr Tyr Ser
        35                  40                  45

Ile Pro Lys Ser Asp Asn Pro Lys Lys Ile Val Val Pro Lys Val Ser
50                  55                  60

Gly Leu Gln Tyr Arg Val Phe Arg Ile His Leu Pro Asp Pro Asn Lys
65                  70                  75                  80

Phe Gly Phe Pro Asp Thr Ser Phe Tyr Asn Pro Asp Thr Gln Arg Leu
                85                  90                  95

Val Trp Ala Cys Val Gly Val Glu Val Gly Arg Gly Gln Pro Leu Gly
            100                 105                 110

Val Gly Ile Ser Gly His Pro Leu Leu Asn Lys Leu Asp Asp Thr Glu
        115                 120                 125

Asn Ala Ser Ala Tyr Ala Ala Asn Ala Gly Val Asp Asn Arg Glu Cys
130                 135                 140

Ile Ser Met Asp Tyr Lys Gln Thr Gln Leu Cys Leu Ile Gly Cys Lys
145                 150                 155                 160

Pro Pro Ile Gly Glu His Trp Gly Lys Gly Ser Pro Cys Thr Asn Val
                165                 170                 175

Ala Val Asn Pro Gly Asp Cys Pro Pro Leu Glu Leu Ile Asn Thr Val
            180                 185                 190

Ile Gln Asp Gly Asp Met Val Asp Thr Gly Phe Gly Ala Met Asp Phe
        195                 200                 205

Thr Thr Leu Gln Ala Asn Lys Ser Glu Val Pro Leu Asp Ile Cys Thr
210                 215                 220

Ser Ile Cys Lys Tyr Pro Asp Tyr Ile Lys Met Val Ser Glu Pro Tyr
225                 230                 235                 240

Gly Asp Ser Leu Phe Phe Tyr Leu Arg Arg Glu Gln Met Phe Val Arg
                245                 250                 255

His Leu Phe Asn Arg Ala Gly Thr Val Gly Glu Thr Val Pro Ala Asp
            260                 265                 270

Leu Tyr Ile Lys Gly Thr Thr Gly Thr Leu Pro Ser Thr Ser Tyr Phe
```

275                 280                 285
Pro Thr Pro Ser Gly Ser Met Val Thr Ser Asp Ala Gln Ile Phe Asn
            290                 295                 300
Lys Pro Tyr Trp Leu Gln Arg Ala Gln Gly His Asn Asn Gly Ile Cys
305                 310                 315                 320
Trp Ser Asn Gln Leu Phe Val Thr Val Val Asp Thr Thr Arg Ser Thr
                325                 330                 335
Asn Met Ser Leu Cys Ala Ala Ile Ser Thr Ser Glu Thr Thr Tyr Lys
            340                 345                 350
Asn Thr Asn Phe Lys Glu Tyr Leu Arg His Gly Glu Glu Tyr Asp Leu
            355                 360                 365
Gln Phe Ile Phe Gln Leu Cys Lys Ile Thr Leu Thr Ala Asp Ile Met
            370                 375                 380
Thr Tyr Ile His Ser Met Asn Ser Thr Ile Leu Glu Asp Trp Asn Phe
385                 390                 395                 400
Gly Leu Gln Pro Pro Gly Gly Thr Leu Glu Asp Thr Tyr Arg Phe
                405                 410                 415
Val Thr Ser Gln Ala Ile Ala Cys Gln Lys His Thr Pro Pro Ala Pro
            420                 425                 430
Lys Glu Asp Pro Leu Lys Lys Tyr Thr Phe Trp Glu Val Asn Leu Lys
            435                 440                 445
Glu Lys Phe Ser Ala Asp Leu Asp Gln Phe Pro Leu Gly Arg Lys Phe
            450                 455                 460
Leu Leu Gln Ala Gly Leu Glu Ala Lys Pro Lys Phe Thr Leu Gly Lys
465                 470                 475                 480
Arg Lys Ala Thr Pro Thr Thr Ser Ser Thr Ser Thr Ala Lys Arg
                485                 490                 495
Lys Lys Arg Lys Leu
            500

<210> SEQ ID NO 10
<211> LENGTH: 500
<212> TYPE: PRT
<213> ORGANISM: Artificial Sequence
<220> FEATURE:
<223> OTHER INFORMATION: H16N30-35T4-31S2

<400> SEQUENCE: 10

Met Leu Pro Ser Glu Ala Thr Val Tyr Leu Pro Pro Val Pro Val Ser
1               5                   10                  15
Lys Val Val Ser Thr Asp Glu Tyr Val Ala Arg Thr Asn Ile Tyr Tyr
                20                  25                  30
His Ala Gly Thr Ser Arg Leu Leu Ala Val Gly His Pro Tyr Phe Pro
            35                  40                  45
Ile Lys Lys Pro Asn Asn Asn Lys Ile Leu Val Pro Lys Val Ser Gly
        50                  55                  60
Leu Gln Tyr Arg Val Phe Arg Ile His Leu Pro Asp Pro Asn Lys Phe
65                  70                  75                  80
Gly Phe Pro Asp Thr Ser Phe Tyr Asn Pro Asp Thr Gln Arg Leu Val
                85                  90                  95
Trp Ala Cys Val Gly Val Glu Val Gly Arg Gly Gln Pro Leu Gly Val
            100                 105                 110
Gly Ile Ser Gly His Pro Leu Leu Asn Lys Phe Asp Asp Thr Glu Asn
        115                 120                 125

Ser Asn Arg Tyr Ala Gly Gly Pro Gly Thr Asp Asn Arg Glu Cys Ile

```
                130             135             140
Ser Met Asp Tyr Lys Gln Thr Gln Leu Cys Leu Ile Gly Cys Lys Pro
145                 150                 155                 160

Pro Ile Gly Glu His Trp Gly Lys Gly Ser Pro Cys Thr Asn Val Ala
                165                 170                 175

Val Asn Pro Gly Asp Cys Pro Pro Leu Glu Leu Ile Asn Thr Val Ile
            180                 185                 190

Gln Asp Gly Asp Met Val Asp Thr Gly Phe Gly Ala Met Asp Phe Thr
        195                 200                 205

Thr Leu Gln Ala Asn Lys Ser Glu Val Pro Leu Asp Ile Cys Thr Ser
210                 215                 220

Ile Cys Lys Tyr Pro Asp Tyr Ile Lys Met Val Ser Glu Pro Tyr Gly
225                 230                 235                 240

Asp Ser Leu Phe Phe Tyr Leu Arg Arg Glu Gln Met Phe Val Arg His
                245                 250                 255

Leu Phe Asn Arg Ala Gly Thr Val Gly Glu Thr Val Pro Ala Asp Leu
            260                 265                 270

Tyr Ile Lys Gly Thr Thr Gly Thr Leu Pro Ser Thr Ser Tyr Phe Pro
        275                 280                 285

Thr Pro Ser Gly Ser Met Val Thr Ser Asp Ala Gln Ile Phe Asn Lys
    290                 295                 300

Pro Tyr Trp Leu Gln Arg Ala Gln Gly His Asn Asn Gly Ile Cys Trp
305                 310                 315                 320

Ser Asn Gln Leu Phe Val Thr Val Val Asp Thr Thr Arg Ser Thr Asn
                325                 330                 335

Met Ser Leu Cys Ala Ala Ile Ser Thr Ser Glu Thr Thr Tyr Lys Asn
            340                 345                 350

Thr Asn Phe Lys Glu Tyr Leu Arg His Gly Glu Glu Tyr Asp Leu Gln
        355                 360                 365

Phe Ile Phe Gln Leu Cys Lys Ile Thr Leu Thr Ala Asp Ile Met Thr
    370                 375                 380

Tyr Ile His Ser Met Asn Ser Thr Ile Leu Glu Asp Trp Asn Phe Gly
385                 390                 395                 400

Leu Gln Pro Pro Pro Gly Gly Thr Leu Glu Asp Thr Tyr Arg Phe Val
                405                 410                 415

Thr Ser Gln Ala Ile Ala Cys Gln Lys His Thr Pro Pro Ala Pro Lys
            420                 425                 430

Glu Asp Pro Leu Lys Lys Tyr Thr Phe Trp Glu Val Asn Leu Lys Glu
        435                 440                 445

Lys Phe Ser Ala Asp Leu Asp Gln Phe Pro Leu Gly Arg Lys Phe Leu
    450                 455                 460

Leu Gln Ala Gly Leu Glu Ala Lys Pro Lys Phe Thr Leu Gly Lys Arg
465                 470                 475                 480

Lys Ala Thr Pro Thr Thr Ser Ser Thr Ser Thr Thr Ala Lys Arg Lys
                485                 490                 495

Lys Arg Lys Leu
        500

<210> SEQ ID NO 11
<211> LENGTH: 500
<212> TYPE: PRT
<213> ORGANISM: Artificial Sequence
<220> FEATURE:
<223> OTHER INFORMATION: H16N30-35T4-31S3
```

<400> SEQUENCE: 11

```
Met Leu Pro Ser Glu Ala Thr Val Tyr Leu Pro Pro Val Pro Val Ser
1               5                   10                  15

Lys Val Val Ser Thr Asp Glu Tyr Val Ala Arg Thr Asn Ile Tyr Tyr
                20                  25                  30

His Ala Gly Thr Ser Arg Leu Leu Ala Val Gly His Pro Tyr Phe Pro
            35                  40                  45

Ile Lys Lys Pro Asn Asn Asn Lys Ile Leu Val Pro Lys Val Ser Gly
        50                  55                  60

Leu Gln Tyr Arg Val Phe Arg Ile His Leu Pro Asp Pro Asn Lys Phe
65                  70                  75                  80

Gly Phe Pro Asp Thr Ser Phe Tyr Asn Pro Asp Thr Gln Arg Leu Val
                85                  90                  95

Trp Ala Cys Val Gly Val Glu Val Gly Arg Gly Gln Pro Leu Gly Val
                100                 105                 110

Gly Ile Ser Gly His Pro Leu Leu Asn Lys Leu Asp Asp Thr Glu Asn
            115                 120                 125

Ala Ser Ala Tyr Ala Ala Asn Ala Gly Val Asp Asn Arg Glu Cys Ile
            130                 135                 140

Ser Met Asp Tyr Lys Gln Thr Gln Leu Cys Leu Ile Gly Cys Lys Pro
145                 150                 155                 160

Pro Ile Gly Glu His Trp Gly Lys Gly Ser Pro Cys Ser Asn Asn Ala
                165                 170                 175

Ile Thr Pro Gly Asp Cys Pro Pro Leu Glu Leu Ile Asn Thr Val Ile
                180                 185                 190

Gln Asp Gly Asp Met Val Asp Thr Gly Phe Gly Ala Met Asp Phe Thr
            195                 200                 205

Thr Leu Gln Ala Asn Lys Ser Glu Val Pro Leu Asp Ile Cys Thr Ser
            210                 215                 220

Ile Cys Lys Tyr Pro Asp Tyr Ile Lys Met Val Ser Glu Pro Tyr Gly
225                 230                 235                 240

Asp Ser Leu Phe Phe Tyr Leu Arg Arg Glu Gln Met Phe Val Arg His
                245                 250                 255

Leu Phe Asn Arg Ala Gly Thr Val Gly Glu Thr Val Pro Ala Asp Leu
                260                 265                 270

Tyr Ile Lys Gly Thr Thr Gly Thr Leu Pro Ser Thr Ser Tyr Phe Pro
            275                 280                 285

Thr Pro Ser Gly Ser Met Val Thr Ser Asp Ala Gln Ile Phe Asn Lys
            290                 295                 300

Pro Tyr Trp Leu Gln Arg Ala Gln Gly His Asn Asn Gly Ile Cys Trp
305                 310                 315                 320

Ser Asn Gln Leu Phe Val Thr Val Val Asp Thr Thr Arg Ser Thr Asn
                325                 330                 335

Met Ser Leu Cys Ala Ala Ile Ser Thr Ser Glu Thr Thr Tyr Lys Asn
            340                 345                 350

Thr Asn Phe Lys Glu Tyr Leu Arg His Gly Glu Glu Tyr Asp Leu Gln
            355                 360                 365

Phe Ile Phe Gln Leu Cys Lys Ile Thr Leu Thr Ala Asp Ile Met Thr
            370                 375                 380

Tyr Ile His Ser Met Asn Ser Thr Ile Leu Glu Asp Trp Asn Phe Gly
385                 390                 395                 400

Leu Gln Pro Pro Pro Gly Gly Thr Leu Glu Asp Thr Tyr Arg Phe Val
                405                 410                 415
```

```
Thr Ser Gln Ala Ile Ala Cys Gln Lys His Thr Pro Pro Ala Pro Lys
            420                 425                 430

Glu Asp Pro Leu Lys Lys Tyr Thr Phe Trp Glu Val Asn Leu Lys Glu
            435                 440                 445

Lys Phe Ser Ala Asp Leu Asp Gln Phe Pro Leu Gly Arg Lys Phe Leu
        450                 455                 460

Leu Gln Ala Gly Leu Glu Ala Lys Pro Lys Phe Thr Leu Gly Lys Arg
465                 470                 475                 480

Lys Ala Thr Pro Thr Thr Ser Ser Thr Ser Thr Thr Ala Lys Arg Lys
            485                 490                 495

Lys Arg Lys Leu
            500

<210> SEQ ID NO 12
<211> LENGTH: 500
<212> TYPE: PRT
<213> ORGANISM: Artificial Sequence
<220> FEATURE:
<223> OTHER INFORMATION: H16N30-35T4-31S5

<400> SEQUENCE: 12

Met Leu Pro Ser Glu Ala Thr Val Tyr Leu Pro Val Pro Val Ser
1               5                   10                  15

Lys Val Val Ser Thr Asp Glu Tyr Val Ala Arg Thr Asn Ile Tyr Tyr
            20                  25                  30

His Ala Gly Thr Ser Arg Leu Leu Ala Val Gly His Pro Tyr Phe Pro
            35                  40                  45

Ile Lys Lys Pro Asn Asn Asn Lys Ile Leu Val Pro Lys Val Ser Gly
        50                  55                  60

Leu Gln Tyr Arg Val Phe Arg Ile His Leu Pro Asp Pro Asn Lys Phe
65                  70                  75                  80

Gly Phe Pro Asp Thr Ser Phe Tyr Asn Pro Asp Thr Gln Arg Leu Val
                85                  90                  95

Trp Ala Cys Val Gly Val Glu Val Gly Arg Gly Gln Pro Leu Gly Val
            100                 105                 110

Gly Ile Ser Gly His Pro Leu Leu Asn Lys Leu Asp Asp Thr Glu Asn
        115                 120                 125

Ala Ser Ala Tyr Ala Ala Asn Ala Gly Val Asp Asn Arg Glu Cys Ile
130                 135                 140

Ser Met Asp Tyr Lys Gln Thr Gln Leu Cys Leu Ile Gly Cys Lys Pro
145                 150                 155                 160

Pro Ile Gly Glu His Trp Gly Lys Gly Ser Pro Cys Thr Asn Val Ala
                165                 170                 175

Val Asn Pro Gly Asp Cys Pro Pro Leu Glu Leu Ile Asn Thr Val Ile
            180                 185                 190

Gln Asp Gly Asp Met Val Asp Thr Gly Phe Gly Ala Met Asp Phe Thr
        195                 200                 205

Thr Leu Gln Ala Asn Lys Ser Glu Val Pro Leu Asp Ile Cys Thr Ser
    210                 215                 220

Ile Cys Lys Tyr Pro Asp Tyr Ile Lys Met Val Ser Glu Pro Tyr Gly
225                 230                 235                 240

Asp Ser Leu Phe Phe Tyr Leu Arg Arg Glu Gln Met Phe Val Arg His
                245                 250                 255

Leu Phe Asn Arg Ala Gly Thr Val Gly Glu Thr Val Pro Ala Asp Leu
            260                 265                 270
```

Tyr Ile Lys Gly Thr Thr Gly Thr Leu Pro Ser Thr Ser Tyr Phe Pro
            275                 280                 285

Thr Pro Ser Gly Ser Met Val Thr Ser Asp Ala Gln Ile Phe Asn Lys
        290                 295                 300

Pro Tyr Trp Leu Gln Arg Ala Gln Gly His Asn Asn Gly Ile Cys Trp
305                 310                 315                 320

Ser Asn Gln Leu Phe Val Thr Val Asp Thr Thr Arg Ser Thr Asn
            325                 330                 335

Met Ser Leu Cys Ala Ala Ile Ala Asn Ser Asp Thr Thr Phe Lys Ser
            340                 345                 350

Ser Asn Phe Lys Glu Tyr Leu Arg His Gly Glu Glu Tyr Asp Leu Gln
            355                 360                 365

Phe Ile Phe Gln Leu Cys Lys Ile Thr Leu Thr Ala Asp Ile Met Thr
        370                 375                 380

Tyr Ile His Ser Met Asn Ser Thr Ile Leu Glu Asp Trp Asn Phe Gly
385                 390                 395                 400

Leu Gln Pro Pro Pro Gly Gly Thr Leu Glu Asp Thr Tyr Arg Phe Val
            405                 410                 415

Thr Ser Gln Ala Ile Ala Cys Gln Lys His Thr Pro Pro Ala Pro Lys
            420                 425                 430

Glu Asp Pro Leu Lys Lys Tyr Thr Phe Trp Glu Val Asn Leu Lys Glu
            435                 440                 445

Lys Phe Ser Ala Asp Leu Asp Gln Phe Pro Leu Gly Arg Lys Phe Leu
        450                 455                 460

Leu Gln Ala Gly Leu Glu Ala Lys Pro Lys Phe Thr Leu Gly Lys Arg
465                 470                 475                 480

Lys Ala Thr Pro Thr Thr Ser Ser Thr Ser Thr Thr Ala Lys Arg Lys
            485                 490                 495

Lys Arg Lys Leu
            500

<210> SEQ ID NO 13
<211> LENGTH: 1596
<212> TYPE: DNA
<213> ORGANISM: Artificial Sequence
<220> FEATURE:
<223> OTHER INFORMATION: DNA sequence encoding SEQ ID NO:1

<400> SEQUENCE: 13
atgcaggtga cttttattta catcctagtt attacatgtt acgaaaacga cgtaaacgtt      60
taccatattt tttttcagat gtctctttgg cttcctagtg aggccactgt ctacttgcct     120
cctgtcccag tatctaaggt tgtaagcacg gatgaatatg ttgcacgcac aaacatatat     180
tatcatgcag gaacatccag actacttgca gttggacatc cctattttcc tattaaaaaa     240
cctaacaata caaaatatt agttcctaaa gtatcaggat acaatacag ggtatttaga      300 atacatttac ctgaccccaa taagtttggt tttcctgaca cctcattta taatccagat     360 acacagcggc tggtttgggc ctgtgtaggt gttgaggtag gtcgtggtca gccattaggt     420
gtgggcatta gtggccatcc tttattaaat aaattggatg acacagaaaa tgctagtgct     480
tatgcagcaa atgcaggtgt ggataataga gaatgtatat ctatggatta caaacaaaca     540
caattgtgtt taattggttg caaaccacct ataggggaac actggggcaa aggatcccca     600
tgtaccaatg ttgcagtaaa tccaggtgat tgtccaccat tagagttaat aaacacagtt     660
attcaggatg gtgatatggt tgatactggc tttggtgcta tggacttta cattacag     720

```
gctaacaaaa gtgaagttcc actggatatt tgtacatcta tttgcaaata tccagattat    780
attaaaatgg tgtcagaacc atatggcgac agcttatttt tttatctacg aagggaacaa    840
atgtttgtta gacatttatt taatagggct ggtgctgttg gtgataatgt accagacgat    900
ttatacatta aaggctctgg gtctactgca aatttagcca gttcaaatta ttttcctaca    960
cctagtggtt ctatggttac ctctgatgcc caaatattca ataaaccttA ctggttacaa   1020
cgagcacagg gccacaataa tggcatttgt tggggtaacc aactatttgt tactgttgtt   1080
gatactacac gcagtacaaa tatgtcatta tgtgctgcca tatctacttc agaaactaca   1140
tataaaaata ctaactttaa ggagtaccta cgacatgggg aggaatatga tttacagttt   1200 attttcaac tgtgcaaaat aaccttaact gcagacatta tgacatacat acattctatg    1260
aattccacta ttttggagga ctggaatttt ggtctacaac ctcccccagg aggcacacta   1320
gaagatactt ataggtttgt aacatcccag gcaattgctt gtcaaaaaca tacacctcca   1380
gcacctaaag aagatcccct taaaaaatac actttttggg aagtaaattt aaaggaaaag   1440
ttttctgcag acctagatca gtttccttta ggacgcaaat ttttactaca agcaggattg   1500
gaggccaaac caaaatttac attaggaaaa cgaaaagcta cacccaccac ctcatctacc   1560
tctacaactg ctaaacgcaa aaaacgtaag ctgtaa                             1596
```

<210> SEQ ID NO 14
<211> LENGTH: 1509
<212> TYPE: DNA
<213> ORGANISM: Artificial Sequence
<220> FEATURE:
<223> OTHER INFORMATION: DNA sequence encoding SEQ ID NO:2

<400> SEQUENCE: 14

```
atgagcctgt ggaggagcaa cgaggccacc gtgtacctgc cccccgtgag cgtgagcaag    60
gtggtgagca ccgacgagta cgtgaccagg accaacatct actaccacgc cggcagcagc   120
aggctgctgg ccgtgggcca cccctactac gccatcaaga agcaggacag caacaagatc   180
gccgtgccca aggtgagcgg cctgcagtac agggtgttca gggtgaagct gcccgacccc   240
aacaagttcg gcttccccga caccagcttc tacgaccccg ccagccagag gctggtgtgg   300
gcctgcaccg cgtggaggt gggcagggc cagcccctgg gcgtgggcat cagcggccac   360 ccctgctga caagctgga cgacaccgag aacagcaaca gtacgtggg caacagcggc   420 accgacaaca gggagtgcat cagcatggac tacaagcaga cccagctgtg cctgatcggc   480
tgcaggcccc ccatcggcga gcactgggc aagggcaccc cctgcaacgc caaccaggtg   540
aaggccggcg agtgcccccc cctggagctg ctgaacaccg tgctgcagga cggcgacatg   600
gtggacaccg gcttcggcgc catggacttc accaccctgc aggccaacaa gagcgacgtg   660
cccctggaca tctgcagcag catctgcaag taccccgact acctgaagat ggtgagcgag   720
ccctacggcg acatgctgtt cttctacctg aggagggagc agatgttcgt gaggcacctg   780
ttcaacaggg ccggcaccgt gggcgagacc gtgcccgccg acctgtacat caagggcacc   840
accggcaccc tgcccagcac cagctacttc cccacccccA gcggcagcat ggtgaccagc   900
gacgcccaga tcttcaacaa gccctactgg ctgcagaggg cccagggcca caacaacggc   960
atctgctgga gcaaccagct gttcgtgacc gtggtggaca ccaccaggag caccaacatg   1020
agcgtgtgca gcgccgtgag cagcagcgac agcacctaca gaacgacaa cttcaaggag   1080 tacctgaggc acggcgagga gtacgacctg cagttcatct tccagctgtg caagatcacc   1140
```

-continued

```
ctgaccgccg acgtgatgac ctacatccac agcatgaacc ccagcatcct ggaggactgg    1200
aacttcggcc tgaccccccc ccccagcggc accctggagg acacctacag gtacgtgacc    1260
agccaggccg tgacctgcca gaagcccagc gccccaagc caaggacga ccccctgaag      1320 aactacacct tctgggaggt ggacctgaag gagaagttca cgccgacct ggaccagttc     1380 cccctgggca ggaagttcct gctgcaggcc ggcctgaagg ccaggcccaa cttcaggctg    1440
ggcaagaggg ccgcccccgc cagcaccagc aagaagagca gcaccaagag gaggaaggtg    1500
aagagctga                                                           1509
```

<210> SEQ ID NO 15
<211> LENGTH: 1515
<212> TYPE: DNA
<213> ORGANISM: Artificial Sequence
<220> FEATURE:
<223> OTHER INFORMATION: DNA sequence encoding SEQ ID NO:3

<400> SEQUENCE: 15

```
atgagcctgt ggaggcccag cgaggccacc gtgtacctgc cccccgtgcc cgtgagcaag     60
gtggtgagca ccgacgagta cgtgaccagg accaacatct actaccacgc cggcagcgcc   120
aggctgctga ccgtgggcca cccctactac agcatcccca gagcgacaa ccccaagaag    180 atcgtggtgc ccaaggtgag cggcctgcag tacagggtgt tcagggtgag gctgcccgac   240
cccaacaagt tcggcttccc cgacaccagc ttctacaacc cgagaccca gaggctggtg    300 tgggcctgcg tgggcctgga ggtgggcagg ggccagcccc tgggcgtggg catcagcggc   360 cacccctgc tgaacaagtt cgacgacacc gagaacagca caggtacgc cggcggcccc    420 ggcaccgaca cagggagtg catcagcatg gactacaagc agacccagct gtgcctgctg    480
ggctgcaagc cccccatcgg cgagcactgg gcaagggca gccctgcag caacaacgcc    540 atcaccccg gcgactgccc ccctggag ctgaagaaca gcgtgatcca ggacggcgac    600 atggtgaca ccggcttcgg cgccatggac ttcaccgccc tgcaggacac caagagcaac    660 gtgccctgg acatctgcaa cagcatctgc aagtacccg actactgaa gatggtggcc    720 gagccctacg gcgacaccct gttcttctac ctgaggaggg agcagatgtt cgtgaggcac    780
ttcttcaaca ggagcggcac cgtgggcgag agcgtgccca ccgacctgta catcaaggc    840 agcggcagca ccgccaccct ggccaacagc acctactcc ccaccccag cggcagcatg     900 gtgaccagcg acgcccagat cttcaacaag ccctactgga tgcagagggc caggcccac    960 aacaacggca tctgctgggg caaccagctg ttcgtgaccg tggtggacac caccaggagc   1020
accaacatga gcgtgtgcgc cgccatcgcc aacagcgaca ccacccttca agagcagcaac   1080 ttcaaggagt acctgaggca cggcgaggag ttcgacctgc agttcatctt ccagctgtgc    1140
aagatcaccc tgagcgccga catcatgacc tacatccaca gcatgaaccc cgccatcctg    1200
gaggactgga cttcggcct gaccccccc cccagcggca gcctggagga cacctacagg    1260
ttcgtgacca gccaggccat cacctgccag aagaccgccc ccagaagcc caaggaggac    1320 ccctttaagg actacgtgtt ctgggaggtg aacctgaagg agaagttcag cgccgacctg    1380
gaccagttcc ccctgggcag gaagttcctg ctgcaggccg gctacagggc caggcccaag    1440
ttcaaggccg gcaagaggag ccgcccccagc gccagcacca ccacccccgc caagaggaag    1500
aagaccaaga agtaa                                                    1515
```

<210> SEQ ID NO 16
<211> LENGTH: 1509

| <212> TYPE: DNA
| <213> ORGANISM: Artificial Sequence
| <220> FEATURE:
| <223> OTHER INFORMATION: DNA sequence encoding SEQ ID NO:4

<400> SEQUENCE: 16

| atgcttccta gtgaggccac tgtctacttg cctcctgtcc cagtatctaa ggttgtaagc | 60 |
| acggatgaat atgttgcacg cacaaacata tattatcatg caggaacaag caggctgctg | 120 |
| gccgtgggcc acccctacta cgccatcaag aagcaggaca gcaacaagat cgccgtgccc | 180 |
| aaggtgagcg gcctgcagta cagggtgttc aggatacatt tacctgaccc caataagttt | 240 |
| ggttttcctg acacctcatt ttataatcca gatacacagc ggctggtttg ggcctgtgta | 300 |
| ggtgttgagg taggtcgtgg tcagccatta ggtgtgggca ttagtggcca tcctttatta | 360 |
| aataaattgg atgacacaga aaatgctagt gcttatgcag caaatgcagg tgtggataat | 420 |
| agagaatgta tatctatgga ttacaaacaa acacaattgt gtttaattgg ttgcaaacca | 480 |
| cctataggg aacactgggg caaaggatcc ccatgtacca atgttgcagt aaatccaggt | 540 |
| gattgtccac cattagagtt aataaacaca gttattcagg atggtgatat ggttgatact | 600 |
| ggctttggtg ctatggactt tactacatta caggctaaca aaagtgaagt tccactggat | 660 |
| atttgtacat ctatttgcaa atatccagat tatattaaaa tggtgtcaga accatacggc | 720 |
| gacagcttat tttttatct acgaagggaa caaatgtttg ttagacattt atttaatagg | 780 |
| gctggtgctg ttggtgataa tgtaccagac gatttataca ttaaaggctc tgggtctact | 840 |
| gcaaatttag ccagttcaaa ttattttcct acacctagtg gttctatggt tacctctgat | 900 |
| gcccaaatat tcaataaacc ttactggtta caacgagcac agggccacaa taatggcatt | 960 |
| tgttgggggta accaactatt tgttactgtt gttgatacta cacgcagtac aaatatgtca | 1020 |
| ttatgtgctg ccatatctac ttcagaaact acatataaaa atactaactt taaggagtac | 1080 |
| ctacgcatg gggaggaata tgatttacag tttatttttc aactgtgcaa ataaccttta | 1140 |
| actgcagaca ttatgacata catacattct atgaattcca ctatttttgga ggactggaat | 1200 |
| tttggtctac aacctccccc aggaggcaca ctagaagata cttataggtt tgtaacatcc | 1260 |
| caggcaattg cttgtcaaaa acatacacct ccagcaccta agaagatcc ccttaaaaaa | 1320 |
| tacactttt gggaagtaaa tttaaaggaa aagttttctg cagacctaga tcagtttcct | 1380 |
| ttaggacgca aatttttact acaagcagga ttggaggcca aaccaaaatt tacattagga | 1440 |
| aaacgaaaag ctacacccac cacctcatct acctctacaa ctgctaaacg caaaaaacgt | 1500 |
| aagctgtaa | 1509 |

<210> SEQ ID NO 17
<211> LENGTH: 1509
<212> TYPE: DNA
<213> ORGANISM: Artificial Sequence
<220> FEATURE:
<223> OTHER INFORMATION: DNA sequence encoding SEQ ID NO:5

<400> SEQUENCE: 17

| atgcttccta gtgaggccac tgtctacttg cctcctgtcc cagtatctaa ggttgtaagc | 60 |
| acggatgaat atgttgcacg cacaaacata tattatcatg caggaacatc cagactactt | 120 |
| gcagttggac atccctattt tcctattaaa aaacctaaca ataacaaaat attagttcct | 180 |
| aaagtatcag gattacaata cagggtattt agaatacatt tacctgaccc caataagttt | 240 |
| ggttttcctg acacctcatt ttataatcca gatacacagc ggctggtttg ggcctgtgta | 300 |

| | |
|---|---|
| ggcgtggagg tgggcagggg ccagccctg ggcgtgggca tcagcggcca cccctgctg | 360 |
| aacaagctgg acgacaccga gaacagcaac aagtacgtgg gcaacagcgg caccgacaac | 420 |
| agggagtgca tcagcatgga ctacaagcag acccagctgt gcctgatcgg ctgcaaacca | 480 |
| cctataggg aacactgggg caaaggatcc ccatgtacca atgttgcagt aaatccaggt | 540 |
| gattgtccac cattagagtt aataaacaca gttattcagg atggtgatat ggttgatact | 600 |
| ggctttggtg ctatggactt tactacatta caggctaaca aaagtgaagt tccactggat | 660 |
| atttgtacat ctatttgcaa atatccagat tatattaaaa tggtgtcaga accatacggc | 720 |
| gacagcttat ttttttatct acgaagggaa caaatgtttg ttagacattt atttaatagg | 780 |
| gctggtgctg ttggtgataa tgtaccagac gatttataca ttaaaggctc tgggtctact | 840 |
| gcaaatttag ccagttcaaa ttattttcct acacctagtg gttctatggt tacctctgat | 900 |
| gcccaaatat tcaataaacc ttactggtta caacgagcac agggccacaa taatggcatt | 960 |
| tgttggggta accaactatt tgttactgtt gttgatacta cacgcagtac aaatatgtca | 1020 |
| ttatgtgctg ccatatctac ttcagaaact acatataaaa atactaactt taaggagtac | 1080 |
| ctacgacatg gggaggaata tgatttacag tttatttttc aactgtgcaa ataaaccta | 1140 |
| actgcagaca ttatgacata catacattct atgaattcca ctatttggaa ggactggaat | 1200 |
| tttggtctac aacctccccc aggaggcaca ctagaagata cttataggtt tgtaacatcc | 1260 |
| caggcaattg cttgtcaaaa acatacacct ccagcaccta agaagatccc cttaaaaaaa | 1320 |
| tacactttt gggaagtaaa tttaaggaa aagttttctg cagacctaga tcagtttcct | 1380 |
| ttaggacgca aatttttact acaagcagga ttggaggcca aaccaaaatt tacattagga | 1440 |
| aaacgaaaag ctacacccac cacctcatct acctctacaa ctgctaaacg caaaaaacgt | 1500 |
| aagctgtaa | 1509 |

<210> SEQ ID NO 18
<211> LENGTH: 1509
<212> TYPE: DNA
<213> ORGANISM: Artificial Sequence
<220> FEATURE:
<223> OTHER INFORMATION: DNA sequence encoding SEQ ID NO:6

<400> SEQUENCE: 18

| | |
|---|---|
| atgcttccta gtgaggccac tgtctacttg cctcctgtcc cagtatctaa ggttgtaagc | 60 |
| acggatgaat atgttgcacg cacaaacata tattatcatg caggaacatc cagactactt | 120 |
| gcagttggac atccctattt tcctattaaa aaacctaaca ataacaaaat attagttcct | 180 |
| aaagtatcag gattacaata cagggtatt agaatacatt tacctgaccc caataagttt | 240 |
| ggttttcctg cacctcatt ttataatcca gatacacagc ggctggtttg gcctgtgta | 300 |
| ggtgttgagg taggtcgtgg tcagccatta ggtgtgggca ttagtggcca tcctttatta | 360 |
| aataaattgg atgacacaga aaatgctagt gcttatgcag caaatgcagg tgtggataat | 420 |
| agagaatgta tatctatgga ttacaaacaa acacaattgt gtttaattgg ttgcaaacca | 480 |
| cctataggg aacactgggg caaaggaacc ccatgtaacg ctaatcaagt aaaggcaggt | 540 |
| gagtgtccac cattagagtt aataaacaca gttattcagg atggtgatat ggttgatact | 600 |
| ggctttggtg ctatggactt tactacatta caggctaaca aaagtgaagt tccactggat | 660 |
| atttgtacat ctatttgcaa atatccagat tatattaaaa tggtgtcaga accatacggc | 720 |
| gacagcttat ttttttatct acgaagggaa caaatgtttg ttagacattt atttaatagg | 780 |
| gctggtgctg ttggtgataa tgtaccagac gatttataca ttaaaggctc tgggtctact | 840 |

```
gcaaatttag ccagttcaaa ttattttcct acacctagtg gttctatggt tacctctgat    900
gcccaaatat tcaataaacc ttactggtta caacgagcac agggccacaa taatggcatt    960
tgttggggta accaactatt tgttactgtt gttgatacta cacgcagtac aaatatgtca   1020
ttatgtgctg ccatatctac ttcagaaact acatataaaa atactaactt taaggagtac   1080
ctacgacatg ggaggaata tgatttacag tttattttc aactgtgcaa ataaaccttta    1140
actgcagaca ttatgacata catacattct atgaattcca ctattttgga ggactggaat   1200
tttggtctac aacctccccc aggaggcaca ctagaagata cttataggtt tgtaacatcc   1260
caggcaattg cttgtcaaaa acatacacct ccagcaccta agaagatcc ccttaaaaaa    1320
tacactttt gggaagtaaa tttaaaggaa aagttttctg cagacctaga tcagtttcct    1380
ttaggacgca aattttact acaagcagga ttggaggcca aaccaaaatt tacattagga    1440
aaacgaaaag ctacacccac cacctcatct acctctacaa ctgctaaacg caaaaaacgt   1500
aagctgtaa                                                           1509

<210> SEQ ID NO 19
<211> LENGTH: 1503
<212> TYPE: DNA
<213> ORGANISM: Artificial Sequence
<220> FEATURE:
<223> OTHER INFORMATION: DNA sequence encoding SEQ ID NO:7

<400> SEQUENCE: 19
atgcttccta gtgaggccac tgtctacttg cctcctgtcc cagtatctaa ggttgtaagc     60
acggatgaat atgttgcacg cacaaacata tattatcatg caggaacatc cagactactt    120
gcagttggac atccctattt tcctattaaa aaacctaaca ataacaaaat attagttcct    180
aaagtatcag gattacaata cagggtattt agaatacatt tacctgaccc caataagttt    240
ggttttcctg cacctcatt ttataatcca gatacacagc ggctggtttg gcctgtgta     300
ggtgttgagg taggtcgtgg tcagccatta ggtgtgggca ttagtggcca tcctttatta    360
aataaattgg atgacacaga aaatgctagt gcttatgcag caaatgcagg tgtggataat    420
agagaatgta tatctatgga ttacaaacaa acacaattgt gtttaattgg ttgcaaacca    480
cctataggg aacactgggg caaaggatcc ccatgtacca atgttgcagt aaatccaggt    540
gattgtccac cattagagtt aataaacaca gttattcagg atggtgatat ggttgatact    600
ggctttggtg ctatggactt tactacatta caggctaaca aagtgaagt tccactggat    660
atttgtacat ctatttgcaa atatccagat tatattaaaa tggtgtcaga accatatggc    720
gacagcttat tcttctacct gaggagggag cagatgttcg tgaggcacct gttcaacagg    780
gccggcaccg tgggcgagac cgtgcccgcc gacctgtaca tcaagggcac caccggcacc    840
ctgcccagca ccagctactt ccccaccccc agcggcagca tggtgaccag cgacgcccag    900
atcttcaaca gccctactg gctgcagagg gcccagggcc acaacaacgg catctgctgg    960
agtaaccaac tatttgttac tgttgttgat actacacgca gtacaaatat gtcattatgt   1020
gctgccatat ctacttcaga aactacatat aaaaatacta actttaagga gtacctacga   1080
catggggagg aatatgattt acagtttatt tttcaactgt gcaaataac cttaactgca    1140
gacattatga catacataca ttctatgaat tccactattt tggaggactg gaattttggt   1200
ctacaacctc ccccaggagg cacactagaa gatacttata ggtttgtaac atcccaggca   1260
attgcttgtc aaaaacatac acctccagca cctaagaag atccccttaa aaatacact    1320
```

-continued

| | |
|---|---|
| ttttgggaag taaatttaaa ggaaaagttt tctgcagacc tagatcagtt tcctttagga | 1380 |
| cgcaaatttt tactacaagc aggattggag gccaaaccaa aatttacatt aggaaaacga | 1440 |
| aaagctacac ccaccacctc atctacctct acaactgcta aacgcaaaaa acgtaagctg | 1500 |
| taa | 1503 |

<210> SEQ ID NO 20
<211> LENGTH: 1509
<212> TYPE: DNA
<213> ORGANISM: Artificial Sequence
<220> FEATURE:
<223> OTHER INFORMATION: DNA sequence encoding SEQ ID NO:8

<400> SEQUENCE: 20

| | |
|---|---|
| atgcttccta gtgaggccac tgtctacttg cctcctgtcc cagtatctaa ggttgtaagc | 60 |
| acggatgaat atgttgcacg cacaaacata tattatcatg caggaacatc cagactactt | 120 |
| gcagttggac atccctattt tcctattaaa aaacctaaca ataacaaaat attagttcct | 180 |
| aaagtatcag gattacaata caggtatttt agaatacatt tacctgaccc caataagttt | 240 |
| ggttttcctg acacctcatt ttataatcca gatacacagc ggctggtttg ggcctgtgta | 300 |
| ggtgttgagg taggtcgtgg tcagccatta ggtgtgggca ttagtggcca tcctttatta | 360 |
| aataaattgg atgacacaga aaatgctagt gcttatgcag caaatgcagg tgtggataat | 420 |
| agagaatgta tatctatgga ttacaaacaa acacaattgt gtttaattgg ttgcaaacca | 480 |
| cctatagggg aacactgggg caaaggatcc ccatgtacca atgttgcagt aaatccaggt | 540 |
| gattgtccac cattagagtt aataaacaca gttattcagg atggtgatat ggttgatact | 600 |
| ggctttggtg ctatggactt tactacatta caggctaaca aaagtgaagt tccactggat | 660 |
| atttgtacat ctatttgcaa atatccagat tatattaaaa tggtgtcaga accatacggc | 720 |
| gacagcttat ttttttatct acgaagggaa caaatgtttg ttagacattt atttaatagg | 780 |
| gctggtgctg ttggtgataa tgtaccagac gatttataca ttaaaggctc tgggtctact | 840 |
| gcaaatttag ccagttcaaa ttattttcct acacctagtg gttctatggt tacctctgat | 900 |
| gcccaaatat tcaataaacc ttactggtta caacgagcac agggccacaa taatggcatt | 960 |
| tgttggagca accaactatt tgttactgtt gttgatacta cacgcagtac aaatatgtca | 1020 |
| ttatgtgctg ccgtatctag ttcagacagt acatataaaa atgataactt taaggagtac | 1080 |
| ctacgacatg gggaggaata tgatttacag tttatttttc aactgtgcaa aataaccta | 1140 |
| actgcagaca ttatgacata catacattct atgaattcca ctattttgga ggactggaat | 1200 |
| tttggtctac aacctccccc aggaggcaca ctagaagata cttataggtt tgtaacatcc | 1260 |
| caggcaattg cttgtcaaaa acatacacct ccagcaccta agaagatccc cttaaaaaaa | 1320 |
| tacactttt gggaagtaaa tttaaaggaa agttttctg cagacctaga tcagtttcct | 1380 |
| ttaggacgca aattttact acaagcagga ttggaggcca aaccaaaatt tacattagga | 1440 |
| aaacgaaaag ctacacccac cacctcatct acctctacaa ctgctaaacg caaaaaacgt | 1500 |
| aagctgtaa | 1509 |

<210> SEQ ID NO 21
<211> LENGTH: 1506
<212> TYPE: DNA
<213> ORGANISM: Artificial Sequence
<220> FEATURE:
<223> OTHER INFORMATION: DNA sequence encoding SEQ ID NO:9

<400> SEQUENCE: 21

| | |
|---|---|
| atgcttccta gtgaggccac tgtctacttg cctcctgtcc cagtatctaa ggttgtaagc | 60 |
| acggatgaat atgttgcacg cacaaacata tattatcatg caggaacatc cagactactt | 120 |
| gcagtgggcc accoctacta cagcatcccc aagagcgaca ccccaagaa gatcgtggtg | 180 |
| cccaaggtga gcggcctgca gtacagggtg ttcaggatac atttacctga ccccaataag | 240 |
| tttggttttc ctgacacctc attttataat ccagatacac agcggctggt ttgggcctgt | 300 |
| gtaggtgttg aggtaggtcg tggtcagcca ttaggtgtgg gcattagtgg ccatcccttta | 360 |
| ttaaataaat tggatgacac agaaaatgct agtgcttatg cagcaaatgc aggtgtggat | 420 |
| aatagagaat gtatatctat ggattacaaa caaacacaat tgtgtttaat tggttgcaaa | 480 |
| ccacctatag gggaacactg gggcaaagga tccccatgta ccaatgttgc agtaaatcca | 540 |
| ggtgattgtc caccattaga gttaataaac acagttattc aggatggtga tatggttgat | 600 |
| actggctttg gtgctatgga ctttactaca ttacaggcta caaaagtga agttccactg | 660 |
| gatatttgta catctatttg caaatatcca gattatatta aaatggtgtc agaaccatat | 720 |
| ggcgacagct tattcttcta cctgaggagg gagcagatgt tcgtgaggca cctgttcaac | 780 |
| agggccggca ccgtgggcga gaccgtgccc gccgacctgt acatcaaggg caccaccggc | 840 |
| accctgccca gcaccagcta cttccccacc cccagcggca gcatggtgac cagcgacgcc | 900 |
| cagatcttca acaagcccta ctggctgcag agggcccagg gccacaacaa cggcatctgc | 960 |
| tggagtaacc aactatttgt tactgttgtt gatactacac gcagtacaaa tatgtcatta | 1020 |
| tgtgctgcca tatctacttc agaaactaca tataaaaata ctaactttaa ggagtaccta | 1080 |
| cgacatgggg aggaatatga tttacagttt atttttcaac tgtgcaaaat aaccttaact | 1140 |
| gcagacatta tgacatacat acattctatg aattccacta ttttggagga ctggaatttt | 1200 |
| ggtctacaac ctcccccagg aggcacacta gaagatactt ataggtttgt aacatcccag | 1260 |
| gcaattgctt gtcaaaaaca tacacctcca gcacctaaag aagatcccct taaaaaatac | 1320 |
| acttttggg aagtaaattt aaaggaaaag ttttctgcag acctagatca gtttcctta | 1380 |
| ggacgcaaat ttttactaca agcaggattg gaggccaaac caaaatttac attaggaaaa | 1440 |
| cgaaaagcta cacccaccac ctcatctacc tctacaactg ctaaacgcaa aaaacgtaag | 1500 |
| ctgtaa | 1506 |

<210> SEQ ID NO 22
<211> LENGTH: 1503
<212> TYPE: DNA
<213> ORGANISM: Artificial Sequence
<220> FEATURE:
<223> OTHER INFORMATION: DNA sequence encoding SEQ ID NO:10

<400> SEQUENCE: 22

| | |
|---|---|
| atgcttccta gtgaggccac tgtctacttg cctcctgtcc cagtatctaa ggttgtaagc | 60 |
| acggatgaat atgttgcacg cacaaacata tattatcatg caggaacatc cagactactt | 120 |
| gcagttggac atccctattt tcctattaaa aaacctaaca ataacaaaat attagttcct | 180 |
| aaagtatcag gattacaata cagggtattt agaatacatt tacctgaccc caataagttt | 240 |
| ggttttcctg acacctcatt ttataatcca gatacacagc ggctggtttg gcctgtgta | 300 |
| ggtgttgagg tggcaggggg ccagcccctg gccgtgggca tcagcggcca ccccctgctg | 360 |
| aacaagttcg acgacaccga gaacagcaac aggtacgccg cggccccgg caccgacaac | 420 |
| agggagtgca tcagcatgga ctacaagcag acccagctgt gcctgattgg ttgcaaacca | 480 |

```
cctataggggg aacactgggg caaaggatcc ccatgtacca atgttgcagt aaatccaggt      540
gattgtccac cattagagtt aataaacaca gttattcagg atggtgatat ggttgatact      600
ggctttggtg ctatggactt tactacatta caggctaaca aaagtgaagt tccactggat      660
atttgtacat ctatttgcaa atatccagat tatattaaaa tggtgtcaga accatatggc      720
gacagcttat tcttctacct gaggagggag cagatgttcg tgaggcacct gttcaacagg      780
gccggcaccg tgggcgagac cgtgcccgcc gacctgtaca tcaagggcac caccggcacc      840
ctgcccagca ccagctactt ccccaccccc agcggcagca tggtgaccag cgacgcccag      900
atcttcaaca gccctactg gctgcagagg gcccagggcc acaacaacgg catctgctgg      960
agtaaccaac tatttgttac tgttgttgat actacacgca gtacaaatat gtcattatgt     1020
gctgccatat ctacttcaga aactacatat aaaaatacta actttaagga gtacctacga     1080
catggggagg aatatgattt acagtttatt tttcaactgt gcaaaataac cttaactgca     1140
gacattatga catacataca ttctatgaat tccactattt tggaggactg gaattttggt     1200
ctacaacctc ccccaggagg cacactagaa gatacttata ggtttgtaac atcccaggca     1260
attgcttgtc aaaaacatac acctccagca cctaaagaag atcccttaa aaaatacact      1320 ttttgggaag taaatttaaa ggaaaagttt tctgcagacc tagatcagtt tcctttagga     1380 cgcaaattt tactacaagc aggattggag gccaaaccaa aatttacatt aggaaaacga     1440
aaagctacac ccaccacctc atctacctct acaactgcta acgcaaaaa acgtaagctg      1500 taa                                                                   1503
```

<210> SEQ ID NO 23
<211> LENGTH: 1503
<212> TYPE: DNA
<213> ORGANISM: Artificial Sequence
<220> FEATURE:
<223> OTHER INFORMATION: DNA sequence encoding SEQ ID NO:11

<400> SEQUENCE: 23

```
atgcttccta gtgaggccac tgtctacttg cctcctgtcc cagtatctaa ggttgtaagc       60
acggatgaat atgttgcacg cacaaacata tattatcatg caggaacatc cagactactt      120
gcagttggac atccctattt tcctattaaa aaacctaaca ataacaaaat attagttcct      180
aaagtatcag gattacaata cagggtattt agaatacatt tacctgaccc caataagttt      240
ggttttcctg acacctcatt ttataatcca gatacacagc ggctggtttg ggcctgtgta      300
ggtgttgagg taggtcgtgg tcagccatta ggtgtgggca ttagtggcca tcctttatta      360
aataaattgg atgacacaga aaatgctagt gcttatgcag caaatgcagg tgtggataat      420
agagaatgta tatctatgga ttacaaacaa acacaattgt gtttaattgg ctgcaagccc      480
cccatcggcg agcactgggg caagggcagc ccctgcagca caacgccat caccccggc      540 gactgccccc cctggagct gataaacaca gttattcagg atggtgatat ggttgatact      600
ggctttggtg ctatggactt tactacatta caggctaaca aaagtgaagt tccactggat      660
atttgtacat ctatttgcaa atatccagat tatattaaaa tggtgtcaga accatatggc      720
gacagcttat tcttctacct gaggagggag cagatgttcg tgaggcacct gttcaacagg      780
gccggcaccg tgggcgagac cgtgcccgcc gacctgtaca tcaagggcac caccggcacc      840
ctgcccagca ccagctactt ccccaccccc agcggcagca tggtgaccag cgacgcccag      900
atcttcaaca gccctactg gctgcagagg gcccagggcc acaacaacgg catctgctgg      960
agtaaccaac tatttgttac tgttgttgat actacacgca gtacaaatat gtcattatgt     1020
```

| | |
|---|---|
| gctgccatat ctacttcaga aactacatat aaaaatacta actttaagga gtacctacga | 1080 |
| catggggagg aatatgattt acagtttatt tttcaactgt gcaaaataac cttaactgca | 1140 |
| gacattatga catacataca ttctatgaat tccactattt tggaggactg gaattttggt | 1200 |
| ctacaacctc ccccaggagg cacactagaa gatacttata ggtttgtaac atcccaggca | 1260 |
| attgcttgtc aaaaacatac acctccagca cctaaagaag atccccttaa aaaatacact | 1320 |
| ttttgggaag taaatttaaa ggaaaagttt tctgcagacc tagatcagtt tcctttagga | 1380 |
| cgcaaatttt tactacaagc aggattggag gccaaaccaa aatttacatt aggaaaacga | 1440 |
| aaagctacac ccaccacctc atctacctct acaactgcta aacgcaaaaa acgtaagctg | 1500 |
| taa | 1503 |

<210> SEQ ID NO 24
<211> LENGTH: 1503
<212> TYPE: DNA
<213> ORGANISM: Artificial Sequence
<220> FEATURE:
<223> OTHER INFORMATION: DNA sequence encoding SEQ ID NO:12

<400> SEQUENCE: 24

| | |
|---|---|
| atgcttccta gtgaggccac tgtctacttg cctcctgtcc cagtatctaa ggttgtaagc | 60 |
| acggatgaat atgttgcacg cacaaacata tattatcatg caggaacatc cagactactt | 120 |
| gcagttggac atccctattt tcctattaaa aaacctaaca ataacaaaat attagttcct | 180 |
| aaagtatcag gattacaata cagggtattt agaatacatt tacctgaccc caataagttt | 240 |
| ggttttcctg cacctcatt ttataatcca gatacacagc ggctggtttg ggcctgtgta | 300 |
| ggtgttgagg taggtcgtgg tcagccatta ggtgtgggca ttagtggcca tcctttatta | 360 |
| aataaattgg atgacacaga aaatgctagt gcttatgcag caaatgcagg tgtggataat | 420 |
| agagaatgta tatctatgga ttacaaaacaa acacaattgt gtttaattgg ttgcaaacca | 480 |
| cctatagggg aacactgggg caaaggatcc ccatgtacca atgttgcagt aaatccaggt | 540 |
| gattgtccac cattagagtt aataaacaca gttattcagg atggtgatat ggttgatact | 600 |
| ggctttggtg ctatggactt tactacatta caggctaaca aaagtgaagt tccactggat | 660 |
| atttgtacat ctatttgcaa atatccagat tatattaaaa tggtgtcaga accatatggc | 720 |
| gacagcttat tcttctacct gaggagggag cagatgttcg tgaggcacct gttcaacagg | 780 |
| gccggcaccg tgggcgagac cgtgcccgcc gacctgtaca tcaagggcac caccggcacc | 840 |
| ctgcccagca ccagctactt ccccaccccc agcggcagca tggtgaccag cgacgcccag | 900 |
| atcttcaaca gcccctactg gctgcagagg gcccagggcc acaacaacgg catctgctgg | 960 |
| agtaaccaac tatttgttac tgttgttgat actacacgca gtacaaatat gtcattatgc | 1020 |
| gccgccatcg ccaacagcga caccaccttc aagagcagca acttcaagga gtacctgagg | 1080 |
| cacggcgagg agtatgattt acagtttatt tttcaactgt gcaaaataac cttaactgca | 1140 |
| gacattatga catacataca ttctatgaat tccactattt tggaggactg gaattttggt | 1200 |
| ctacaacctc ccccaggagg cacactagaa gatacttata ggtttgtaac atcccaggca | 1260 |
| attgcttgtc aaaaacatac acctccagca cctaaagaag atccccttaa aaaatacact | 1320 |
| ttttgggaag taaatttaaa ggaaaagttt tctgcagacc tagatcagtt tcctttagga | 1380 |
| cgcaaatttt tactacaagc aggattggag gccaaaccaa aatttacatt aggaaaacga | 1440 |
| aaagctacac ccaccacctc atctacctct acaactgcta aacgcaaaaa acgtaagctg | 1500 |

<210> SEQ ID NO 25
<211> LENGTH: 23
<212> TYPE: PRT
<213> ORGANISM: Artificial Sequence
<220> FEATURE:
<223> OTHER INFORMATION: Sequence of amino acid residues at positions
      266-288 of wild-type HPV35 L1 protein

<400> SEQUENCE: 25

Thr Val Gly Glu Thr Val Pro Ala Asp Leu Tyr Ile Lys Gly Thr Thr
1               5                   10                  15

Gly Thr Leu Pro Ser Thr Ser
            20

<210> SEQ ID NO 26
<211> LENGTH: 13
<212> TYPE: PRT
<213> ORGANISM: Artificial Sequence
<220> FEATURE:
<223> OTHER INFORMATION: Sequence of amino acid residues at positions
      50-62 of wild-type HPV31 L1 protein

<400> SEQUENCE: 26

Tyr Ser Ile Pro Lys Ser Asp Asn Pro Lys Lys Ile Val
1               5                   10

<210> SEQ ID NO 27
<211> LENGTH: 16
<212> TYPE: PRT
<213> ORGANISM: Artificial Sequence
<220> FEATURE:
<223> OTHER INFORMATION: Sequence of amino acid residues at positions
      127-142 of wild-type HPV31 L1 protein

<400> SEQUENCE: 27

Phe Asp Asp Thr Glu Asn Ser Asn Arg Tyr Ala Gly Gly Pro Gly Thr
1               5                   10                  15

<210> SEQ ID NO 28
<211> LENGTH: 6
<212> TYPE: PRT
<213> ORGANISM: Artificial Sequence
<220> FEATURE:
<223> OTHER INFORMATION: Sequence of amino acid residues at positions
      177-182 of wild-type HPV31 L1 protein

<400> SEQUENCE: 28

Ser Asn Asn Ala Ile Thr
1               5

<210> SEQ ID NO 29
<211> LENGTH: 24
<212> TYPE: DNA
<213> ORGANISM: Artificial Sequence
<220> FEATURE:
<223> OTHER INFORMATION: Primer

<400> SEQUENCE: 29
atacatttac ctgaccccaa taag                                          24

<210> SEQ ID NO 30
<211> LENGTH: 26
<212> TYPE: DNA
<213> ORGANISM: Artificial Sequence
<220> FEATURE:

<223> OTHER INFORMATION: Primer

<400> SEQUENCE: 30
tgttcctgca tgataatata tgtttg                                    26

<210> SEQ ID NO 31
<211> LENGTH: 45
<212> TYPE: DNA
<213> ORGANISM: Artificial Sequence
<220> FEATURE:
<223> OTHER INFORMATION: Primer

<400> SEQUENCE: 31
aacatatatt atcatgcagg aacaagcagg ctgctggccg tgggc               45

<210> SEQ ID NO 32
<211> LENGTH: 47
<212> TYPE: DNA
<213> ORGANISM: Artificial Sequence
<220> FEATURE:
<223> OTHER INFORMATION: Primer

<400> SEQUENCE: 32
cttattgggg tcaggtaaat gtatcctgaa caccctgtac tgcaggc             47

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
aaaccaccta tagggaaca ctg                                        23

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
tacacaggcc caaaccagcc gc                                        22

<210> SEQ ID NO 35
<211> LENGTH: 44
<212> TYPE: DNA
<213> ORGANISM: Artificial Sequence
<220> FEATURE:
<223> OTHER INFORMATION: Primer

<400> SEQUENCE: 35
gcggctggtt tgggcctgtg taggcgtgga ggtgggcagg ggcc                44

<210> SEQ ID NO 36
<211> LENGTH: 46
<212> TYPE: DNA
<213> ORGANISM: Artificial Sequence
<220> FEATURE:
<223> OTHER INFORMATION: Primer

<400> SEQUENCE: 36
cagtgttccc ctataggtgg tttgcagccg atcaggcaca gctggg              46

```
<210> SEQ ID NO 37
<211> LENGTH: 55
<212> TYPE: DNA
<213> ORGANISM: Artificial Sequence
<220> FEATURE:
<223> OTHER INFORMATION: Primer

<400> SEQUENCE: 37
ggcaaaggaa ccccatgtaa cgctaatcaa gtaaaggcag gtgagtgtcc accat          55

<210> SEQ ID NO 38
<211> LENGTH: 55
<212> TYPE: DNA
<213> ORGANISM: Artificial Sequence
<220> FEATURE:
<223> OTHER INFORMATION: Primer

<400> SEQUENCE: 38
atggtggaca ctcacctgcc tttacttgat tagcgttaca tggggttcct ttgcc          55

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39
tggggtaacc aactatttgt tactg                                           25

<210> SEQ ID NO 40
<211> LENGTH: 23
<212> TYPE: DNA
<213> ORGANISM: Artificial Sequence
<220> FEATURE:
<223> OTHER INFORMATION: Primer

<400> SEQUENCE: 40
taagctgtcg ccatatggtt ctg                                             23

<210> SEQ ID NO 41
<211> LENGTH: 45
<212> TYPE: DNA
<213> ORGANISM: Artificial Sequence
<220> FEATURE:
<223> OTHER INFORMATION: Primer

<400> SEQUENCE: 41
cagaaccata tggcgacagc ttattcttct acctgaggag ggagc                     45

<210> SEQ ID NO 42
<211> LENGTH: 44
<212> TYPE: DNA
<213> ORGANISM: Artificial Sequence
<220> FEATURE:
<223> OTHER INFORMATION: Primer

<400> SEQUENCE: 42
cagtaacaaa tagttggtta ccccagcaga tgccgttgtt gtgg                      44

<210> SEQ ID NO 43
<211> LENGTH: 55
<212> TYPE: DNA
<213> ORGANISM: Artificial Sequence
<220> FEATURE:
<223> OTHER INFORMATION: Primer
```

```
<400> SEQUENCE: 43
atgtgctgcc gtatctagtt cagacagtac atataaaaat gataacttta aggag    55

<210> SEQ ID NO 44
<211> LENGTH: 55
<212> TYPE: DNA
<213> ORGANISM: Artificial Sequence
<220> FEATURE:
<223> OTHER INFORMATION: Primer

<400> SEQUENCE: 44
ctccttaaag ttatcatttt tatatgtact gtctgaacta gatacggcag cacat    55

<210> SEQ ID NO 45
<211> LENGTH: 26
<212> TYPE: DNA
<213> ORGANISM: Artificial Sequence
<220> FEATURE:
<223> OTHER INFORMATION: Primer

<400> SEQUENCE: 45
atacatttac ctgaccccaa taagtt                                     26

<210> SEQ ID NO 46
<211> LENGTH: 24
<212> TYPE: DNA
<213> ORGANISM: Artificial Sequence
<220> FEATURE:
<223> OTHER INFORMATION: Primer

<400> SEQUENCE: 46
tgcaagtagt ctggatgttc ctgc                                       24

<210> SEQ ID NO 47
<211> LENGTH: 46
<212> TYPE: DNA
<213> ORGANISM: Artificial Sequence
<220> FEATURE:
<223> OTHER INFORMATION: Primer

<400> SEQUENCE: 47
caggaacatc cagactactt gcagtgggcc acccctacta cagcat               46

<210> SEQ ID NO 48
<211> LENGTH: 47
<212> TYPE: DNA
<213> ORGANISM: Artificial Sequence
<220> FEATURE:
<223> OTHER INFORMATION: Primer

<400> SEQUENCE: 48
cttattgggg tcaggtaaat gtatcctgaa caccctgtac tgcaggc              47

<210> SEQ ID NO 49
<211> LENGTH: 25
<212> TYPE: DNA
<213> ORGANISM: Artificial Sequence
<220> FEATURE:
<223> OTHER INFORMATION: Primer

<400> SEQUENCE: 49
attggttgca aaccacctat agggg                                      25

<210> SEQ ID NO 50
<211> LENGTH: 25
```

<212> TYPE: DNA
<213> ORGANISM: Artificial Sequence
<220> FEATURE:
<223> OTHER INFORMATION: Primer

<400> SEQUENCE: 50
aacacctaca caggcccaaa ccagc    25

<210> SEQ ID NO 51
<211> LENGTH: 43
<212> TYPE: DNA
<213> ORGANISM: Artificial Sequence
<220> FEATURE:
<223> OTHER INFORMATION: Primer

<400> SEQUENCE: 51
tggtttgggc ctgtgtaggt gttgaggtgg gcaggggcca gcc    43

<210> SEQ ID NO 52
<211> LENGTH: 45
<212> TYPE: DNA
<213> ORGANISM: Artificial Sequence
<220> FEATURE:
<223> OTHER INFORMATION: Primer

<400> SEQUENCE: 52
cctataggtg gtttgcaacc aatcaggcac agctgggtct gcttg    45

<210> SEQ ID NO 53
<211> LENGTH: 23
<212> TYPE: DNA
<213> ORGANISM: Artificial Sequence
<220> FEATURE:
<223> OTHER INFORMATION: Primer

<400> SEQUENCE: 53
ataaacacag ttattcagga tgg    23

<210> SEQ ID NO 54
<211> LENGTH: 26
<212> TYPE: DNA
<213> ORGANISM: Artificial Sequence
<220> FEATURE:
<223> OTHER INFORMATION: Primer

<400> SEQUENCE: 54
aattaaacac aattgtgttt gtttgt    26

<210> SEQ ID NO 55
<211> LENGTH: 45
<212> TYPE: DNA
<213> ORGANISM: Artificial Sequence
<220> FEATURE:
<223> OTHER INFORMATION: Primer

<400> SEQUENCE: 55
aacaaacaca attgtgttta attggctgca agcccccat cggcg    45

<210> SEQ ID NO 56
<211> LENGTH: 46
<212> TYPE: DNA
<213> ORGANISM: Artificial Sequence
<220> FEATURE:
<223> OTHER INFORMATION: Primer

<400> SEQUENCE: 56
ccatcctgaa taactgtgtt tatcagctcc agggggggc agtcgc    46

<210> SEQ ID NO 57
<211> LENGTH: 22
<212> TYPE: DNA
<213> ORGANISM: Artificial Sequence
<220> FEATURE:
<223> OTHER INFORMATION: Primer

<400> SEQUENCE: 57
tatgatttac agtttatttt tc    22

<210> SEQ ID NO 58
<211> LENGTH: 23
<212> TYPE: DNA
<213> ORGANISM: Artificial Sequence
<220> FEATURE:
<223> OTHER INFORMATION: Primer

<400> SEQUENCE: 58
taatgacata tttgtactgc gtg    23

<210> SEQ ID NO 59
<211> LENGTH: 45
<212> TYPE: DNA
<213> ORGANISM: Artificial Sequence
<220> FEATURE:
<223> OTHER INFORMATION: Primer

<400> SEQUENCE: 59
cacgcagtac aaatatgtca ttatgcgccg ccatcgccaa cagcg    45

<210> SEQ ID NO 60
<211> LENGTH: 46
<212> TYPE: DNA
<213> ORGANISM: Artificial Sequence
<220> FEATURE:
<223> OTHER INFORMATION: Primer

<400> SEQUENCE: 60
tgaaaaataa actgtaaatc atactcctcg ccgtgcctca ggtact    46